(12) United States Patent
Eshleman et al.

(10) Patent No.: US 8,679,788 B2
(45) Date of Patent: Mar. 25, 2014

(54) METHODS FOR THE DETECTION OF NUCLEIC ACID DIFFERENCES

(75) Inventors: James R. Eshleman, Lutherville, MD (US); Chanjuan Shi, Lutherville, MD (US); Susan Henrietta Eshleman, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 948 days.

(21) Appl. No.: 10/590,541

(22) PCT Filed: Mar. 22, 2005

(86) PCT No.: PCT/US2005/009391
§ 371 (c)(1),
(2), (4) Date: Aug. 25, 2006

(87) PCT Pub. No.: WO2005/092038
PCT Pub. Date: Oct. 6, 2005

(65) Prior Publication Data
US 2007/0178445 A1      Aug. 2, 2007

Related U.S. Application Data

(60) Provisional application No. 60/555,167, filed on Mar. 22, 2004, provisional application No. 60/619,817, filed on Oct. 18, 2004.

(51) Int. Cl.
*C12P 19/34* (2006.01)
*C12Q 1/68* (2006.01)
*C07H 21/02* (2006.01)

(52) U.S. Cl.
USPC .................. 435/91.2; 435/6.1; 536/24.33

(58) Field of Classification Search
None
See application file for complete search history.

(56) References Cited

U.S. PATENT DOCUMENTS

| | | | |
|---|---|---|---|
| 5,185,243 | A | 2/1993 | Ullman et al. |
| 5,210,015 | A | 5/1993 | Gelfand et al. |
| 2003/0219770 | A1 | 11/2003 | Eshleman et al. |
| 2006/0111312 | A1 | 5/2006 | Eshleman et al. |

FOREIGN PATENT DOCUMENTS

WO       WO-97/45559        5/1997

OTHER PUBLICATIONS

Hacker U.T. et al. Gut 1997 vol. 40, pp. 623-627.*
Juppner H. Bone (Aug. 1995) vol. 17 No. 2, Supplement, pp. 39S-42S.*
Maire F. et al. Brisitsh Journal of Cancer (2002) 87, 551-554.*
Lecomte T. et al. Int. J. Cancer (2002), vol. 100, pp. 542-548.*
Nazarenko I. et al. Nucleic Acids Research (2002) vol. 30 No. 9, printed pp. 1-7.*
Watanabe H. et al. Pancreas (1998) vol. 17, No. 4, pp. 341-347.*
Schouten et al., Nucleic Acids Research, 30(12):1-13 (e57) 2002).
Beck et al., NIH AIDS Research and Reference Reagent Program, pp. 1-24 (2003).
Kapala et al., Journal of Clinical Microbiology, pp. 2480-2483 (2000).
Whitcombe et al., Nature Biotechnology, 17:804-807 (1999).
Favis et al., Nature Biotechnology, 18:561-564 (2000).
Abravaya et al., Nucleic Acids Research, 23(4):675-682 (1995).

* cited by examiner

*Primary Examiner* — Stephen Kapushoc
(74) *Attorney, Agent, or Firm* — Johns Hopkins Technology Transfer

(57) ABSTRACT

The invention provides methods permitting the detection of small amounts of different nucleic acids in the presence of an excess amount of wild-type nucleic acids. Also provided herein are method so detecting infectious disease minority variants, methods of forensic identification, methods of diagnosing cancer and monitoring disease progress.

11 Claims, 31 Drawing Sheets a b

Figure 19

A. Standard curve for quantification

- STD
- Mixtures  200 pg/µl
                    20 pg/µl
                         2 pg/µl B. % heteroplasmy in the mixtures

| Sample # | Heteroplasmy (%) |
|---|---|
| A | 55.3 |
| B | 18.7 |
| C | 3.3 |
| D | 55.7 |
| E | 1.1 |
| F | 27.5 |
| G | 4.02 |
| H | 25.6 |

A.

B.

C.

D.

SEQUENCE LISTING

<160> NUMBER OF SEQ ID NOS: 67

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gtaaaacgac ggccagggag agaggcctgc tgaaaa                          36

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caggaaacag ctatgacttg gatcatattc gtccaca                         37

<210> SEQ ID NO 3
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
actgtaaaac gacggccagt gttcccctca aactggcaga tgcacgcttg tggtagttgg   60
agctgt                                                              66

<210> SEQ ID NO 4
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
actgtaaaac gacggccagt gttcccctca aactggcaga tgcacgcttg tggtagttgg   60
agctga                                                              66

<210> SEQ ID NO 5
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
actgtaaaac gacggccagt gttcccctca aactggcaga tgcacgaact tgtggtagtt   60
ggagttc                                                             67

<210> SEQ ID NO 6
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
actgtaaaac gacggccagt gtcgtattac cgcggctgct ggcaccttgt ggtagttgga   60
gctgg                                                               65

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
tggcgtaggc aagagtgcct ggtcatagct gtttcctgca                           40

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
gtggcgtagg caagagtgcc tggtcatagc tgtttcctgc a                         41

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ctgtaaaacg acggccagtg                                                 20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
tgcaggaaac agctatgacc a                                               21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic probe

<400> SEQUENCE: 11
tcccctcaaa ctggcagatg cacg                                            24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 12
cgtattaccg cggctgctgg cac                                             23

<210> SEQ ID NO 13
<211> LENGTH: 63

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
actgtaaaac gacggccagt gtcgtattac cgcggctgct ggcacgaaca gctttgaggt     60
aca                                                                   63

<210> SEQ ID NO 14
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgtttgtgcc tgtcctggga gtggtcatag ctgtttcctg ca                        42

<210> SEQ ID NO 15
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actgtaaaac gacggccagt gttcccctca aactggcaga tgcacgcgca gggttaaaaa     60
aggac                                                                 65

<210> SEQ ID NO 16
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
actgtaaaac gacggccagt gttcccctca aactggcaga tgcacgcgca gggttaaaaa     60
aggaa                                                                 65

<210> SEQ ID NO 17
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aaatcagtaa cagtactgga tgtgggtgtg gtcatagctg tttcctgca                 49

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggagagaggc ctgctgaaaa                                                 20

```
<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aatgattctg aattagctgt atcgtca                                          27

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aatataaact tgtggtagtt ggacct                                           26

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcaaagacaa ggcgatatgc t                                                21

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccctgacata ctcccaagga                                                  20

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaacctccga gatcgaaga                                                   19

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gcactgcctc tgttaattgt                                                  20
```

```
<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agacttctgg gaagttcaat                                                 20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tggagaaaat tagtagattt                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atccctgggt aaatctgact                                                 20

<210> SEQ ID NO 28
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
actgtaaaac gacggccagt gttcccctca aactggcaga tgcacgagga ataccacatc     60
cagcaggtct aaaaaaggac                                                 80

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaatcagtaa cagtactaga tgtgggggtg gtcatagctg tttcctgca                 49

<210> SEQ ID NO 30
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
actgtaaaac gacggccagt gttcccctca aactggcaga tgcacgagga ataccacatc     60
ctgcagggct aaaaaaggac                                                 80
```

<210> SEQ ID NO 31
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aaatcagtaa cagtactgga tgtgggtgtg gtcatagctg tttcctgca         49

<210> SEQ ID NO 32
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
cgcagggtta aaaagaaaa aatcagtaac agtactggat gtgggtg             47

<210> SEQ ID NO 33
<211> LENGTH: 47
<212> TYPE: DNA
<213> ORGANISM: Human immunodeficiency virus type 1

<400> SEQUENCE: 33
cgcagggtta aaaaggaaa aatcagtaac agtactggat gtgggtg             47

<210> SEQ ID NO 34
<211> LENGTH: 47
<212> TYPE: DNA
<213> ORGANISM: Human immunodeficiency virus type 1

<400> SEQUENCE: 34
cgcagggtta aaaagaaca agtcagtaac matactggat gtgggtg             47

<210> SEQ ID NO 35
<211> LENGTH: 47
<212> TYPE: DNA
<213> ORGANISM: Human immunodeficiency virus type 1

<400> SEQUENCE: 35
ygcagggttr aaaagaaaa aatcagtaac agtactrgat gtgggtg             47

<210> SEQ ID NO 36
<211> LENGTH: 47
<212> TYPE: DNA
<213> ORGANISM: Human immunodeficiency virus type 1

<400> SEQUENCE: 36
cgcagggtta aaraagaara artcagtaac agtwctggat gtgggtg            47

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cgatctctaa cgcgcaagcg                                          20

```
<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cgatttttaa cgcgtaagcg                                                      20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgcttacgcg ttaaaaatcg                                                      20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
tgatttttaa tgtgtaagtg                                                      20

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tagttggacc tgatggcgta ggca                                                 24

<210> SEQ ID NO 42
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aggaataccg catccagcag gtttaaaaaa gaacaaatca gtaacagtac tagatgtggg          60
gg                                                                         62

<210> SEQ ID NO 43
<211> LENGTH: 62
<212> TYPE: DNA
<213> ORGANISM: Human immunodeficiency virus type 1

<400> SEQUENCE: 43
aggaatacca catccagcag gtctaaaaaa ggacaaatca gtaacagtac tagatgtggg          60
gg                                                                         62
```

```
<210> SEQ ID NO 44
<211> LENGTH: 62
<212> TYPE: DNA
<213> ORGANISM: Human immunodeficiency virus type 1

<400> SEQUENCE: 44
aggaatacca catccagcag gtctaaaaaa gaacaaatca gtaacagtac tagatgtggg      60
gg                                                                    62

<210> SEQ ID NO 45
<211> LENGTH: 62
<212> TYPE: DNA
<213> ORGANISM: Human immunodeficiency virus type 1

<400> SEQUENCE: 45
aggaataccg caccctgcag gtttaaaaaa gaacaaatca gtaacagtac tagatgtggg      60
gg                                                                    62

<210> SEQ ID NO 46
<211> LENGTH: 62
<212> TYPE: DNA
<213> ORGANISM: Human immunodeficiency virus type 1

<400> SEQUENCE: 46
aggaataccg catccagcgg gcctaaaaaa gaacaaatca gtaacagtac tagatgtggg      60
gg                                                                    62

<210> SEQ ID NO 47
<211> LENGTH: 62
<212> TYPE: DNA
<213> ORGANISM: Human immunodeficiency virus type 1

<400> SEQUENCE: 47
aggaatacca catccagcgg gcttaaaaaa gaacaaatca gtaacagtac tagatgtggg      60
gg                                                                    62

<210> SEQ ID NO 48
<211> LENGTH: 62
<212> TYPE: DNA
<213> ORGANISM: Human immunodeficiency virus type 1

<400> SEQUENCE: 48
aggaatacca catcctgcag ggctaaaaaa gaacaaatca gtaacagtac tggatgtggg      60
gg                                                                    62

<210> SEQ ID NO 49
<211> LENGTH: 62
<212> TYPE: DNA
<213> ORGANISM: Human immunodeficiency virus type 1

<400> SEQUENCE: 49
aggaataccg catccagcgg gcctaaaaaa gaamaaatca gtaacagtac tagatgtggg      60
gg                                                                    62

<210> SEQ ID NO 50
<211> LENGTH: 62
<212> TYPE: DNA
<213> ORGANISM: Human immunodeficiency virus type 1

<400> SEQUENCE: 50
aggaataccg catcccgcag gtttaaaaaa gaamaaatca gtaacagtac tggatgtggg      60
```

```
gg                                                              62

<210> SEQ ID NO 51
<211> LENGTH: 62
<212> TYPE: DNA
<213> ORGANISM: Human immunodeficiency virus type 1

<400> SEQUENCE: 51
aggaataccg catccagcgg gcttaaaaaa gaamaaatca gtaacagtac tagatgtagg      60
gg                                                              62

<210> SEQ ID NO 52
<211> LENGTH: 62
<212> TYPE: DNA
<213> ORGANISM: Human immunodeficiency virus type 1

<400> SEQUENCE: 52
aggaataccg catcccgcag gtttaaaaaa gaaaaaatca gtaacagtac tagatgtggg      60
gg                                                              62

<210> SEQ ID NO 53
<211> LENGTH: 62
<212> TYPE: DNA
<213> ORGANISM: Human immunodeficiency virus type 1

<400> SEQUENCE: 53
aggaataccg catcccgcag gtttaaaaaa gaacaaatca gtaacagtgc tagatgtggg      60
gg                                                              62

<210> SEQ ID NO 54
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
aggaatacca catcctgcag ggctaaaaaa gaacaaatca gtaacagtac tggatgtggg      60
tg                                                              62

<210> SEQ ID NO 55
<211> LENGTH: 62
<212> TYPE: DNA
<213> ORGANISM: Human immunodeficiency virus type 1

<400> SEQUENCE: 55
aggaatacca catcctgcag ggctaaaaaa ggacaaatca gtaacagtac tggatgtggg      60
tg                                                              62

<210> SEQ ID NO 56
<211> LENGTH: 62
<212> TYPE: DNA
<213> ORGANISM: Human immunodeficiency virus type 1

<400> SEQUENCE: 56
aggaatacca catcctgcag ggctaaaaaa gaacaaatca gtaacagtac tggatgtggg      60
tg                                                              62

<210> SEQ ID NO 57
```

```
<211> LENGTH: 62
<212> TYPE: DNA
<213> ORGANISM: Human immunodeficiency virus type 1

<400> SEQUENCE: 57
aggaatacca catcctgcag ggctaaaaaa gaacaaatca gtaacagtac tagatgtggg    60
tg                                                                   62

<210> SEQ ID NO 58
<211> LENGTH: 62
<212> TYPE: DNA
<213> ORGANISM: Human immunodeficiency virus type 1

<400> SEQUENCE: 58
agggatacca catccagcag ggctaaaaaa gaacaaatca gtaacagtac tggatgtggg    60
tg                                                                   62

<210> SEQ ID NO 59
<211> LENGTH: 62
<212> TYPE: DNA
<213> ORGANISM: Human immunodeficiency virus type 1

<400> SEQUENCE: 59
aggaataccr catcctgcag ggctaaaaaa gaamaaatca gtaacagtac tggatgtggg    60
tg                                                                   62

<210> SEQ ID NO 60
<211> LENGTH: 62
<212> TYPE: DNA
<213> ORGANISM: Human immunodeficiency virus type 1

<400> SEQUENCE: 60
agggataccg catcctgcag ggctaaaaaa gaahaaatca gtaacagtac tggatgtggg    60
tg                                                                   62

<210> SEQ ID NO 61
<211> LENGTH: 62
<212> TYPE: DNA
<213> ORGANISM: Human immunodeficiency virus type 1

<400> SEQUENCE: 61
aggaatacca catcctgcag ggctaaaaaa gaamaaatca gtaacagtac tggatgtggg    60
tg                                                                   62

<210> SEQ ID NO 62
<211> LENGTH: 62
<212> TYPE: DNA
<213> ORGANISM: Human immunodeficiency virus type 1

<400> SEQUENCE: 62
aggaatacca catcctgcag gactaaaaaa gaamaaatca gtaacagtac tggatgtggg    60
tg                                                                   62

<210> SEQ ID NO 63
<211> LENGTH: 62
<212> TYPE: DNA
<213> ORGANISM: Human immunodeficiency virus type 1

<400> SEQUENCE: 63
aggaatacca catcctgcag ggytaaaaaa gaahaaatca gtaacagtwc tggatgtggg    60
```

```
tg                                                              62

<210> SEQ ID NO 64
<211> LENGTH: 62
<212> TYPE: DNA
<213> ORGANISM: Human immunodeficiency virus type 1

<400> SEQUENCE: 64
aggaatacca catcctgcag ggctgaaaaa gaaaaaatca gtaacartac tggatgtggg    60
tg                                                              62

<210> SEQ ID NO 65
<211> LENGTH: 62
<212> TYPE: DNA
<213> ORGANISM: Human immunodeficiency virus type 1

<400> SEQUENCE: 65
aggaatacca catcctgcag ggctaaaaaa gaaaaaatca gtaacagtac tggatgtggg    60
tg                                                              62

<210> SEQ ID NO 66
<211> LENGTH: 62
<212> TYPE: DNA
<213> ORGANISM: Human immunodeficiency virus type 1

<400> SEQUENCE: 66
aggaataccg catcctgcag ggctaaaaaa gaawaaatca gtaacagtac tggatgtggg    60
tg                                                              62

<210> SEQ ID NO 67
<211> LENGTH: 62
<212> TYPE: DNA
<213> ORGANISM: Human immunodeficiency virus type 1

<400> SEQUENCE: 67
aggaatacca catcctgcag ggctaaaaaa gaaaaaatca gtaacagtac tggatgtggg    60
tg                                                              62
```

METHODS FOR THE DETECTION OF NUCLEIC ACID DIFFERENCES

PRIORITY

This application claims priority to U.S. Provisional Application Nos. 60/555,167 filed Mar. 22, 2004 and 60/619,817 filed Oct. 18, 2004, both of which are incorporated herein by reference in their entirety.

GOVERNMENT SUPPORT

This work was supported by the National Institutes of Health under grant numbers: R01 CA81439, U01-AI-46745; U01-AI-48054; U01-AI-38858), R01-HD042965-01; N01-AI-35173; and N01-CO-12400.

BACKGROUND OF THE INVENTION

Single base mutations play a role in cancer and other human diseases, and can be useful markers for diagnostic tests. Mutations in viral genomes can cause resistance to antiviral drugs. Unfortunately, clinical samples often contain low-levels of mutant cells and viruses mixed with a vast excess of wild-type cells or viruses. Development of sensitive and accurate methods for detection of point mutations is an important challenge.

Single base mutations can be detected with restriction fragment length polymorphism/Southern blot assays (Vary, C. P. et al. *Genet Anal* 13, 59-65 (1996); Chen, J. & Viola, M. V. *Anal Biochem* 195, 51-6 (1991).), oligonucleotide ligation assays (Redston, M. S., Papadopoulos, N., Caldas, C., Kinzler, K. W. & Kern, S. E. *Gastroenterology* 108, 383-92 (1995); and Rothschild, C. B., Brewer, C. S., Loggie, B., Beard, G. A. & Triscott, M. X. *J Immunol Methods* 206, 11-9 (1997)), and allele-specific PCR (AS-PCR) assays or the amplification refractory mutation system (Clayton, S. J. et al. K, *Clin Chem* 46, 1929-38 (2000); Takeda, S., Ichii, S. & Nakamura, Y. *Hum Mutat* 2, 112-7 (1993); Germer, S., Holland, M. J. & Higuchi, R. *Genome Res* 10, 258-66 (2000); and Kwok, S. et al. *Nucleic Acids Res* 18, 999-1005 (1990)). The limit of detection of those assays is often limited to 0.1-1% (mutant/wild-type ratio of 1/1,000-1/100). Other assays can detect single base mutations in unique sequence contexts at lower levels (McKinzie, P. B. & Parsons, B. L. *Mutat Res* 517, 209-20 (2002); Lichtenstein, A. V., Serdjuk, O. I., Sukhova, T. I., Melkonyan, H. S. & Umansky, S. R. *Nucleic Acids Res* 29, E90-0 (2001); Schimanski, C. C., Linnemann, U. & Berger, M. R. *Cancer Res* 59, 5169-75 (1999); and Kaur, M. et al. *Mutagenesis* 17, 365-74 (2002)), but cannot be generally applied. Detection of point mutations with real-time quantitative PCR (Q-PCR) assays is often hampered by cross-hybridization of probes to wild-type templates (Oliver, D. H., Thompson, R. E., Griffin, C. A. & Eshleman, J. R. *J Mol Diagn* 2, 202-8 (2000)).

New initiatives support development of assays for early diagnosis of common cancers, for families at increased risk and population screening (Srivastava, S. & Rossi, S. C. *Int J Cancer* 69, 35-7 (1996); Sidransky, D. et al. *Science* 256, 102-5 (1992); and Traverso, G. et al. *N Engl J Med* 346, 311-20 (2002)). Such assays may also help monitor bone marrow transplant engraftment, and disease recurrence in cancer patients after treatment. Pancreatic cancer is usually diagnosed at an advanced stage, and early diagnosis is critical for improving survival rates. KRAS2 mutations are present in most pancreatic cancers and can be detected in pancreatic duct juice, as well as plasma and stool (Wilentz, R. E. et al. *Cancer* 82, 96-103 (1998); and Mulcahy, H. & Farthing, M. J. *Ann Oncol* 10 Suppl 4, 114-7 (1999)). However, KRAS2 mutations can also be detected in pancreatic duct juice and stool from patients with chronic pancreatitis or pancreatic intraepithelial neoplasias (PanINs) (Hruban, R. H., Wilentz, R. E. & Kern, S. E. *Am J Pathol* 156, 1821-5 (2000) and Caldas, C. et al. *Cancer Res* 54, 3568-73 (1994)). Qualitative detection of mutant KRAS2 alone is not an accurate predictor of pancreatic cancer (Watanabe, H. et al. *Pancreas* 17, 341-7 (1998)), but there is a need in the art for quantitative assays for KRAS2 mutations in biological fluids might be able to distinguish between pancreatic cancer and other conditions (Tada, M. et al. *Dig Dis Sci* 43, 15-20 (1998)).

In the management of patients with viral infections, for example, HIV, antiretroviral drugs can select for HIV-1 with drug-resistance mutations in protease and reverse transcriptase. Most HIV-1 genotyping assays are relatively insensitive for detection of minority variants with resistance mutations. A recent study suggests that the presence of such variants can influence treatment response (Mellors J., et al, Antiviral Therapy., 8: S150, 2003). A multicenter study used different assays to detect the K103N drug resistance mutation (Halvas E., et al, Antiviral Therapy, 8, S102, 2003). Thus, there is also a need in the art for assays to detect point mutations to aid in the management of patients viral infections, for example, HIV infections.

Several assays can detect single base substitutions, but their limit of detection is generally 0.1-10% (ratio of mutant/wild-type, equivalent to 1/10-1/1,000). DNA sequencing typically can detect mutant molecules only at a 10-25% level, depending in part on sequence context [Larder, 1993 #40]. Restriction fragment length polymorphism (RFLP)/Southern blot assays typically have a limit of detection of 0.5-5% [Vary, 1996 #3][Chen, 1991 #19]. The oligonucleotide ligation assay (OLA), even with sensitive capillary electrophoresis detection, can only detect minor species at about 0.1-1% [Redston, 1995 #4][Rothschild, 1997 #5]. Ligation chain reaction uses four oligonucleotides and ligase as an alternative to polymerase, but its limit of detection is approximately 0.1 to 1% [Barany, 1991 #49]. Allele-specific PCR (AS-PCR) or the amplification refractory mutation system (ARMS) can only detect approximately 1% of mutant DNA [Germer, 2000 #44; Kwok, 1990 #28] since the Taq polymerase still extends to some degree from a mispaired primer. In addition, most of these techniques lack of accurate quantification. Real-time quantitative PCR (Q-PCR) is remarkably quantitative over a wide dynamic range, but has been difficult to apply to the detection of point mutations because mutant probes that differ by a single base often cross-hybridize with the wild-type template [Oliver, 2000 #43]. Thus, there is a need in the art for assays with increased sensitivity to detect, for example, a single copy of a virus in a sample.

BRIEF SUMMARY OF THE INVENTION

The invention provides a new strategy that permits detection of small amounts of point mutation containing DNA in the presence of an excess amount of wild-type DNA (e.g. 1:10,000 to 1:100,000). This is accomplished by first performing selective oligonucleotide ligation on the mutation containing DNA using two unique DNA primers. The DNA primers contain regions that are target specific, but also contain tails (e.g. M13) that permit subsequent amplification of the ligated product. Since the strategy involves a ligation step followed by a real-time PCR amplification step, designated as "LigAmp". One of the ligation primers also contains a region of completely foreign DNA (e.g. lac-Z) that is used as probe site during the subsequent RQ-PCR (real time quantitative PCR) step. High selectivity is achieved since probe cleavage cannot occur without prior ligation. The ligation step can be multiplexed to simultaneously detect multiple point mutations.

Provided herein are methods of detecting infectious disease minority variants. The methods, in one aspect comprise contacting a nucleic acid sample from a subject or a cell with at least one oligonucleotide pair to form a reaction mixture, wherein a pair comprises a first (P1) and a second (P2) oligonucleotide, wherein P1 comprises a first gene specific region and a first primer region, P2 comprises a second gene specific region and a second primer region; either P1 or P2 comprise a detection region; either P1 or P2 comprise a nucleotide difference in the gene specific region; and P1 and P2 are suitable for ligation to one another; subjecting the reaction mixture to a ligation reaction; and amplifying a ligation product to form a reaction product.

In one embodiment, the minority variant is viral or microbial. In a related embodiment, the viral minority variant is HIV, HBV, HCV, CMV, influenza, HSV, RSV, or VZV. In another related embodiment, the viral minority variant is a viral drug-resistant minority variant.

According to certain embodiments, the nucleotide difference detected encodes one or more of the amino acid changes K103N, Y181C, K103E, K103R, K103T, G190A, P236L, or a substitution in the viral genome associated with altered susceptibility to one or more antiviral drugs.

According to one aspect, the invention provides, method of differentiating pancreatic cancer from chronic pancreatitis comprising, contacting a nucleic acid sample from a subject or a cell with at least one oligonucleotide pair to form a reaction mixture, wherein a pair comprises a first (P1) and a second (P2) oligonucleotide, wherein P1 comprises a first gene specific region and a first primer region, P2 comprises a second gene specific region and a second primer region; either P1 or P2 comprise a detection region; either P1 or P2 comprise a nucleotide difference in the gene specific region; and P1 and P2 are suitable for ligation to one another; subjecting the reaction mixture to a ligation reaction; and amplifying a ligation product to form a reaction product.

In one embodiment, the nucleotide difference is in KRAS2. In another embodiment, the KRAS2 nucleotide difference is one or more of G35A, G35T, G35C, G34A, G34T, G38A, or A182T.

The aspect may further comprising analyzing the reaction product, determining the KRAS mutation level, and/or further comprising monitoring the KRAS mutation levels.

According to certain embodiments, a mutation level of less than 0.6% indicates chronic pancreatitis. In related embodiment, a mutation level of less than 0.5% indicates chronic pancreatitis. In another related embodiment, a mutation level of greater than 0.6% indicates pancreatic cancer. In a further related embodiment, a mutation level of from between about 0.5% to about 80% indicates pancreatic cancer.

In one aspect, the invention provides a method of diagnosing a disease in a subject comprising, obtaining a biological sample from a subject; contacting the biological sample with at least one oligonucleotide pair to form a reaction mixture, wherein a pair comprises a first (P1) and a second (P2) oligonucleotide, wherein P1 comprises a first gene specific region and a first primer region, P2 comprises a second gene specific region and a second primer region; either P1 or P2 comprise a detection region; either P1 or P2 comprise a nucleotide difference in the gene specific region; and P1 and P2 are suitable for ligation to one another; subjecting the reaction mixture to a ligation reaction; and amplifying a ligation product to form a reaction product.

In one embodiment, the disease is a disease caused by, induced by or related to a nucleotide difference in at least one gene.

In one embodiment, the disease is Parkinson's disease, Duchenne muscular dystrophy, Niemann-Pick disease, polyposis, neurofibromatosis, polycystic kidney disease, Tay-Sachs disease, xeroderma pigmentosa, ataxia-telangiectasia, Huntington disease, Li-Fraumeni syndrome, beta-thalassemia, sickle cell anemia, hemoglobin C disease, hemophilia, acute intermittent porphyria, cystic fibrosis, diabetes, obesity, cardiovascular disease, cancer, chronic pancreatitis, cerebrovascular disease, respiratory disease, influenza, pneumonia, Alzheimer's, infectious disease, septicemia, liver disease, or hypertension. In a related aspect, the cancer is leukemia, lymphoma, melanoma, neuroblastoma, retinoblastoma, rhabdomyosarcoma, Ewing sarcoma, head and neck cancer, skin cancer, melanoma, brain cancer, esophageal cancer, stomach cancer, lung cancer, breast cancer, colon cancer, ovarian cancer, testicular cancer, pancreatic cancer, prostate cancer, rectal cancer, bladder cancer, renal cancer, uterine cancer, thyroid cancer, liver cancer, biliary cancer, bronchial cancer, laryngeal cancer or testicular cancer.

In one embodiment, the disease is a residual disease. In a related embodiment, the diagnosis is for early detection. In another related embodiment, the diagnosis is molecular relapse. In a further related embodiment, the determination is to predict chemosensitivity or chemoresistance.

In another embodiment, the subject is a fetus and the diagnosis is a prenatal diagnosis. In a related embodiment, the subject is a fetus and the sample is maternal in origin, such as peripheral blood.

Provided herein, according to one aspect, are methods of forensic identification, comprising, obtaining a nucleic acid forensic sample; contacting a nucleic acid forensic sample with at least one oligonucleotide pair to form a reaction mixture, wherein a pair comprises a first (P1) and a second (P2) oligonucleotide, wherein P1 comprises a first gene specific region and a first primer region, P2 comprises a second gene specific region and a second primer region; either P1 or P2 comprise a detection region; either P1 or P2 comprise a nucleotide difference in the gene specific region; and P1 and P2 are suitable for ligation to one another; subjecting the reaction mixture to a ligation reaction; and amplifying a ligation product to form a reaction product.

In one embodiment, the forensic sample is from a crime scene. In another embodiment, the forensic nucleic acid sample is derived from a biological sample.

In one embodiment, the method further comprises comparing the reaction product to a reference nucleic acid sequence.

In one embodiment, the reference nucleic acid sequence is from a family member, a suspect, a person of interest, or a standard.

Further provided herein are methods of identifying a sample containing an uncommon genetic change, comprising, obtaining a pooled nucleic acid sample; contacting the pooled sample with at least one oligonucleotide pair to form a reaction mixture, wherein a pair comprises a first (P1) and a second (P2) oligonucleotide, wherein P1 comprises a first gene specific region and a first primer region, P2 comprises a second gene specific region and a second primer region; either P1 or P2 comprise a detection region; either P1 or P2 comprise a nucleotide difference in the gene specific region; and P1 and P2 are suitable for ligation to one another; subjecting the reaction mixture to a ligation reaction; and amplifying a ligation product to form a reaction product.

In one embodiment, the pooled nucleic acid sample is a pool of samples.

In one embodiment, the mutated gene specific region is at the 3' end of P1 and/or the 5' end of P2. In a related embodiment, the mutated gene specific region is the 3' nucleotide of P1 or the 5' nucleotide of P2. In another related embodiment, the mutated gene specific region is within the 3' five nucleotides of P1 or the 5' five nucleotides of P2. In a related embodiment, the mutated gene specific region is between about 1 and about 5 nucleotides in length. In a further related embodiment, the mutated gene specific region is between about 5 and about 30 nucleotides in length In one embodiment, P1 and P2 ligate only if the nucleotide difference is present in the nucleic acid sample.

In another embodiment, the contacting the nucleic acid sample with a third (P3) and a fourth (P4) oligonucleotide wherein P3 comprises a third gene specific region and a third primer binding region and P4 comprises a probe binding region, a fourth primer binding region, a fourth gene specific region and a second mutated gene specific region.

In another embodiment, the contacting the nucleic acid sample with a third (P3) wherein P3 comprises a probe binding region unique from P2, a primer binding region, a third gene specific region that targets the wild-type version of the gene. In a related embodiment, the contacting the nucleic acid sample is with a fifth (P5) and a sixth (P6) oligonucleotide wherein P5 comprises a fifth gene specific region and a fifth primer binding region and P6 comprises a probe binding region, a sixth primer binding region, a sixth gene specific region, and a third mutated gene specific region. In another embodiment, the contacting the nucleic acid sample is with 4 to 1000 oligonucleotide pairs wherein one of each pair comprises a gene specific region and a primer binding region, while the other in the pair comprises a probe binding region, a primer binding region, a gene specific region, and a mutated gene specific region.

In one aspect, the invention provides methods of detecting a nucleic acid sequence difference, comprising, contacting a nucleic acid sample with at least one oligonucleotide pair, wherein a pair comprises a first (P1) and a second (P2) oligonucleotide, wherein P1 and P2 bind to a nucleic acid to form a reaction mixture, and wherein P1 comprises a first gene specific region and a first primer binding region and P2 comprises a probe binding region, a second primer binding region and a second gene specific region, wherein there a nucleotide gap between the first and second gene specific regions contains the nucleic acid difference; providing the reaction mixture with a nucleotide complementary to the nucleotide difference; subjecting P1, P2, and the nucleotide to ligation conditions to form a ligation product; and amplifying the ligation product to form a reaction product. In one embodiment, the nucleic acid difference is one or more of KRAS2 nucleotide difference, K103N HIV-1 drug-resistance nucleotide difference, CFTR nucleotide difference, p53 nucleotide difference, or Braf nucleotide difference.

In another embodiment, the nucleotide ligates to one or more of P1 or P2 if the nucleotide difference is present.

According to certain embodiments, the nucleic acid difference is a base substitution, single nucleotide polymorphism, microsatellite, transversion, transition, missense mutation, nonsense mutation, insertion, deletion, frameshift mutation, internal tandem repeat, amplification, translocation, germline mutation, somatic mutation or altered methylation.

According to certain embodiments, P1 and P2 are between about 10 and about 140 nucleotides in length.

According to certain embodiments, the first and second gene specific regions are between about 10 and about 100 nucleotides in length.

According to certain embodiments, the first or the second primer regions comprise one or more of an M13 forward, M13 reverse, T7, SP6, T3, lambda gt10 forward, lambda gt10 reverse, lambda gt11 forward, lambda gt11reverse, DNA zipcode, address code, DNA barcodes, DNA tags or DNA anti-tag sequences.

According to certain embodiments, wherein analyzing is by bead hybridization, microarray, rolling circle amplification, hyperbranching rolling circle amplification, ligase chain reaction, strand displacement amplification, transcription mediated amplification, or nucleic acid sequence base amplification.

In one embodiment, the analyzing is by real time quantitative PCR, Taqman probing, molecular beacons, FRET hybridization probes, scorpion probes, Sybr green, or melting curve analysis.

According to certain embodiments, the detection region is a probe binding region.

According to certain embodiments, the probe binding region is a known DNA sequence that is not complementary to the sequence up-stream and down-stream of the gene specific regions and the mutated gene specific region.

In one embodiment, the analyzing is with a probe complementary to the probe binding region.

In another embodiment, the detection region is a known nucleotide sequence that is not complementary to the sequence up-stream and down-stream of the gene specific regions and the mutated gene specific region.

According to certain embodiments, the detection region is one or more of a lacZ sequence, 16S rDNA sequence, M13 forward, M13 reverse, T7, SP6, T3, lambda gt10 forward, lambda gt10 reverse, lambda gt11 forward, lambda gt11reverse, DNA zipcode, address code, DNA barcodes, DNA tags or DNA anti-tag sequences.

In another embodiment, the detection region contains a labeled nucleotide. In a related embodiment, the labeled nucleotide is fluorescent, radioactively, chemical moiety or colorimetricly labeled.

According to certain embodiments, the nucleic acid sample is plasmid DNA, genomic DNA, PCR product, mitochondria DNA, RNA, DNA virus, RNA virus or a cell.

In one embodiment, the amplifying is by PCR, quantitative PCR, real time PCR, or real time quantitative PCR. In a related embodiment, the amplifying is quantitative.

According to certain embodiments, the methods may further comprise one or more of removing unbound P1 and P2 prior to amplifying, providing a nucleic acid sample, amplifying genomic DNA to produce a nucleic acid sample, analyzing the reaction product, Q-PCR probe cleavage after the amplification of the ligation product, and/or providing one or more of a DNA, RNA, LNA, PNA probe complementary and overlapping with the wild-type allele to the ligation reaction.

In one embodiment, the nucleic acid sample contains from between about a 1:1 to about a 1:100,000 ratio of mutated nucleic acid to wild type nucleic acid. In a related embodiment, the nucleic acid sample contains from between about a 1:1000 to about a 1:10,000 ratio of mutated nucleic acid to wild tupe nucleic acid.

In another embodiment, the amplifying is by PCR, real-time PCR, rt-PCR, real time rt-PCR, Q-PCR, Taqman probing, molecular beacons, FRET hybridization probes, scorpion probes, Sybr green, and/or melting curve analysis.

In one embodiment, wherein analyzing is by performing chromatography, capillary electrophoresis, microfluidic analysis, slab gel electrophoresis, intercalating agent, Southern blot real-time PCR, surface plasmon resonance, flow cytometry, fluorescence polarization, hybridization, microarray detection, or radiography.

According to one embodiment, the intercalating agent is ethidium bromide or an unsymmetrical cyanin dye.

In one embodiment, the amplifying is bottom strand synthesis.

According to certain embodiments, the subject is a mammal, e.g., a human.

According to certain embodiments, the biological sample is one or more of pancreatic duct juice, peripheral blood, serum, plasma, red cells, white cells, platelets, skin, urine, feces, tears, mucus, sputum, bile, sweat, or fine needle aspirate.

According to certain embodiments, the methods are operable to detects infectious disease minority variants, differentiates pancreatic cancer from chromic pancreatitis, diagnoses a disease, or forensically identifies samples.

In one embodiment, a target nucleic acid or sample nucleic acid has two strands and wherein a pair of oliginuclietides is directed to both nucleic acid strands. The signal of the output of the assay depends on there being a mutation detected on both strands.

In one embodiment, the methods may further comprise providing a blocking probe complementary to the wild-type nucleic acid. The sequence of the blocking probe overlaps P1 and P2, thereby straddling the ligation site of the oligonucleotides.

In one aspect, provided herein are kits for one of more of detecting infectious disease minority variants, differentiating pancreatic cancer from chromic pancreatitis, diagnosing a disease, forensic identification, comprising, at least one first (P1) and at least one second (P2) oligonucleotide to form a reaction mixture, wherein P1 comprises a first gene specific region and a first primer region, P2 comprises a second gene specific region and a second primer region; either P1 or P2 comprise a detection region; either P1 or P2 comprise a nucleotide difference in the gene specific region; and P1 and P2 are suitable for ligation to one another; and instructions for use.

In another aspect, provided herein are kits for one of more of detecting infectious disease minority variants, differentiating pancreatic cancer from chromic pancreatitis, diagnosing a disease, forensic identification, or detecting a nucleic acid sequence difference, comprising, at least one first (P1) and at least one second (P2) oligonucleotide, wherein P1 and P2 bind to a nucleic acid to form a reaction mixture, and wherein P1 comprises a first gene specific region and a first primer binding region and P2 comprises a probe binding region, a second primer binding region and a second gene specific region, wherein there a nucleotide gap between the first and second gene specific regions contains the nucleic acid difference; and instructions for use.

Other embodiments of the invention are disclosed infra.

To further increase specificity, a Gap was included, similar to that included in Gap-LCR to improve specificity in that reaction. In standard LigAmp, upstream and downstream oligonucleotides bind adjacently to each other upon hybridization to the target. In GAP-LigAmp, after hybridization to the target, a gap of one or several bases is present between these two oligonucleotides. Taq DNA polymerase and the specific nucleotide corresponding to the mutant base were added into the ligation reaction to fill the gap, and the resultant oligonucleotides can be joined by DNA ligase (Figure A and B). When using wild-type DNA as a template, the corresponding wild-type base is not included in the reaction, therefore, no extension should occur. In the event that extension still does occur, no ligation should take place. There are then two steps that must both occur for ligation to occur and therefore two independent layers of specificity.

To determine the sensitivity of GAP-LigAmp, a KRAS2 mutant SW480 DNA (G12T) was serially diluted into wild-type HeLa DNA (GGT). The compositions in the ligation reaction are similar to that in LigAmp, except that GAP upstream oligonucleotide, Taq DNA polymerase (1 U) and dTTP (20 mmol). The extension/ligation condition are: 95° C. for 4 min followed by 99 cycles of 95° C. for 30 seconds and 60° C. for 4 mins. As shown in the panel C below, GAP-LigAmp is able detect mutant KRAS2 at a level of 0.001% (1:100,000). Wild-type signal is undetectable (does not cross threshold). This result suggests that introduction of a GAP into the reaction further improves the specificity of LigAmp.

Figure 15:
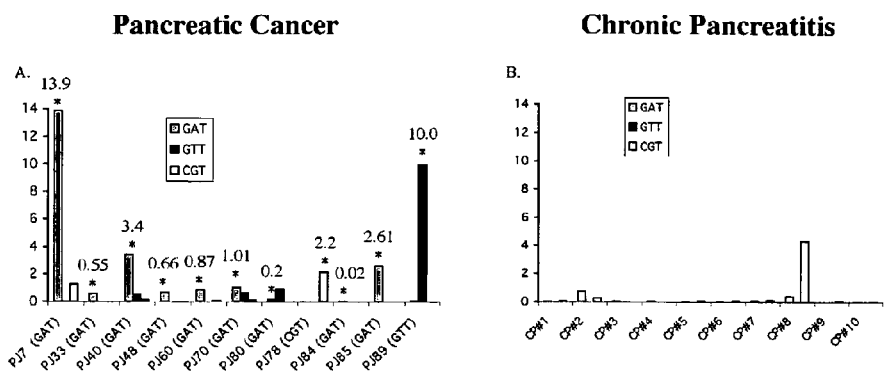

FIG. 15 depicts the results of LigAmp for early detection of Pancreas Cancer. It has now been demonstrated that LigAmp can be applied to early detection of cancers.

Figure 16:
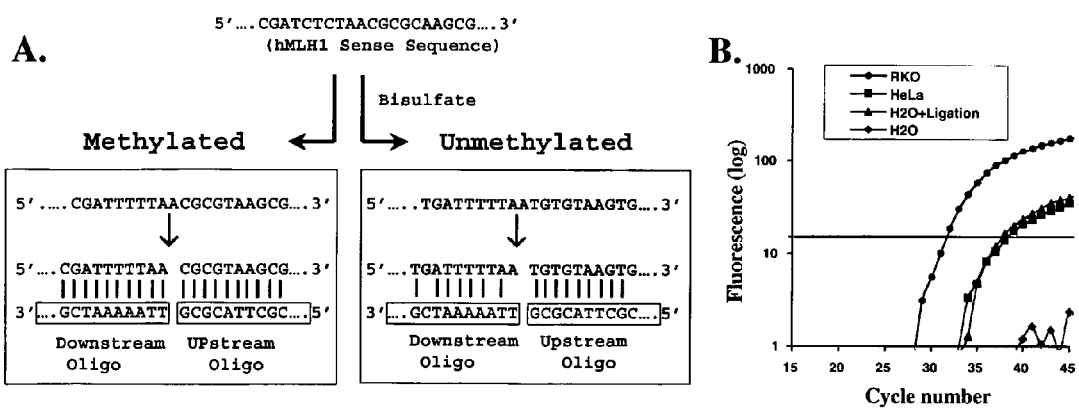

FIG. 16 depicts the results of LigAmp in the detection of methylated DNA. DNA methylation has been used as a biomarker to distinguished tumors from normal tissues. The most widely used assay for detection of methylation levels is methylation-specific PCR (MS-PCR). In MS-PCR, unmethylated cytosines are first converted into thymine by sodium bisulfate treatment, while methylated cytosines in CpG islands are refractory to the treatment, thereby converting methylation information into sequence difference. The DNA is then amplified using primers designed specifically for methylated or unmethylated DNA. LigAmp was designed to detect point mutations. Single base differences between methylated and unmethylated DNA are created after bisulfate modification. FIG. 16A discloses SEQ ID NOS 37-38, 38, 39, 40, 40 and 39, respectively, in order of appearance.

In colon cancer, methylation of hMLH1 promoter region accounts for some MSI tumors. Analysis of hMLH1 methylation might be helpful for colon cancer and other cancer detection. HMLH1 was used as a model to test our hypothesis. Methylation of a small proximal region (−248 to −178 relative to transcription start site) in the promoter was associated with loss of hMLH1 expression. The oligonucleotides were designed to hybridize to the methylated sequence following bisulfate treatment. The 3'-end of the upstream oligonucleotide pairs with the cytosine base of a methylated CpG island (Figure A). Multiple CpG islands in the upstream target site, might enhance the specificity, but are not required for the assay.

Figure 17:
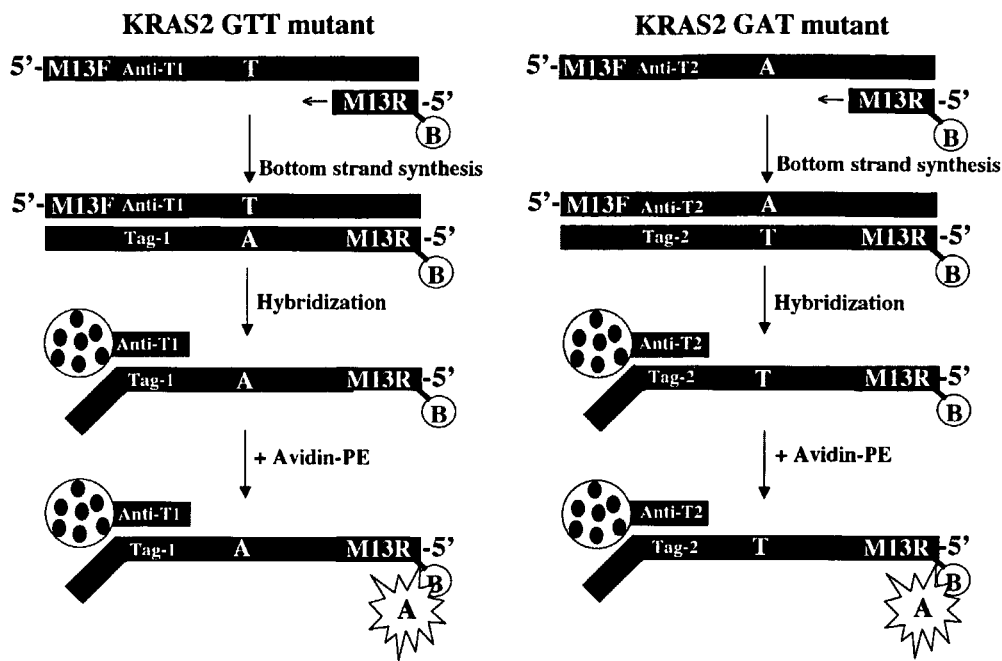

Genomic DNA was extracted from an hMLH1 methylated colon cell line, RKO, and an hMLH1 unmethylated cell line, HeLa (as a negative control). One microgram genomic DNA was first subjected to sodium bisulfate treatment and subsequently column purification. The modified DNA (200 ng) was used as ligation template. The Q-PCR Amplification signal for RKO appears earlier than Hela (shown in the Figure B). The difference in Ct values between RKO and HeLa is 7 cycles. The signal from Hela DNA overlaps with that from H2O LigAmp control. This data demonstrate that LigAmp can be used to detect methylation FIG. 17 depicts the results of multiplex LigAmp with simultaneous Bead Detection. It has now been demonstrated that the LigAmp reaction can be multiplexed using real-time PCR as the detection system. However real-time PCR can only be multiplexed to a certain degree before all of the fluorescent channels are exhausted (typically about 4 channels currently). Using the Luminex system, 100 beads can be distinguished from each other using 10 different levels of 2 independent fluorophors. Each of these beads also contains a DNA tag (Flexmap system). Therefore instead of using LacZ or 16SrDNA as probes, one can substitute the tags present on the beads. Such a system is illustrated below. In this system, 2 different KRAS2 mutations are detected, each on one of the uniquely colored beads. A third bead can be used to detect wildtype KRAS. Other beads can be used to detect p53 mutations, Braf mutations, etc. Other systems similarly can be used to detect DNA via DNA tags, zipcodes, address codes and the like.

Figure 18:
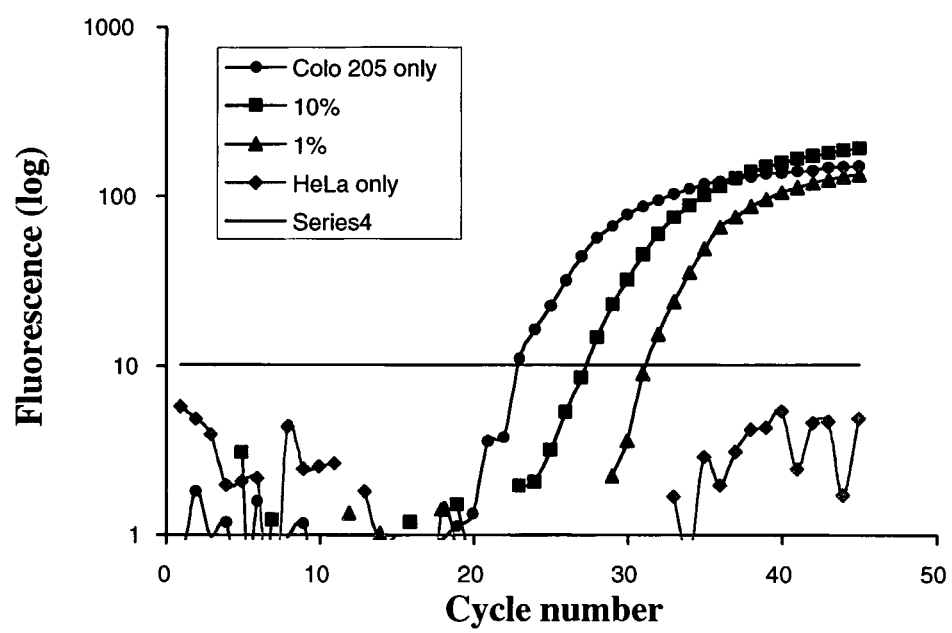

FIG. 18 depicts the detection of Braf mutation using LigAmp. Point mutations of the BRAF protooncogene were recently found in a wide variety of tumors, and most notably in melanoma, papillary thyroid cancer and colon cancer. A V599E (T1796A) hotspot mutation within the BRAF gene was reported in these tumors. Therefore, BRAF can be a promising tumor marker for these malignancies.

To demonstrate the capability of LigAmp to detect BRAF mutations, BRAF mutant genomic DNA was serially diluted into (from 1.2 μg to 12 ng) isolated from a colon cancer cell line, Colo205, and mixed with wild-type DNA (1.2 μg) from HeLa cells. The 3'-terminal base of the upstream ligation oligonucleotide for the mutant was designed to perfectly pair with the mutated base as usual. The result shows that LigAmp is able to detect and quantify the BRAF mutation in the DNA mixtures.

FIG. 19 depicts mitochondrial mutation detection with LigAmp. Heteroplasmic mutations of mitochondrial DNA are sources of human diseases. Detection of low levels of heteroplasmy is essential for both the diagnosis of some medial disorders, as well as for forensic identify determinations. The mutant (C6371T) mitochondrial DNA was diluted into the wild-type mitchondrial DNA ranging from 1% to 50%. Then, the mixtures were subjected to PCR amplification. Two hundred pg PCR product was used as template for LigAmp. The result is shown in the Figure. The data demonstrate the ability of LigAmp to detect hepteroplasmy in mitochondria at a low level.

Figure 20:
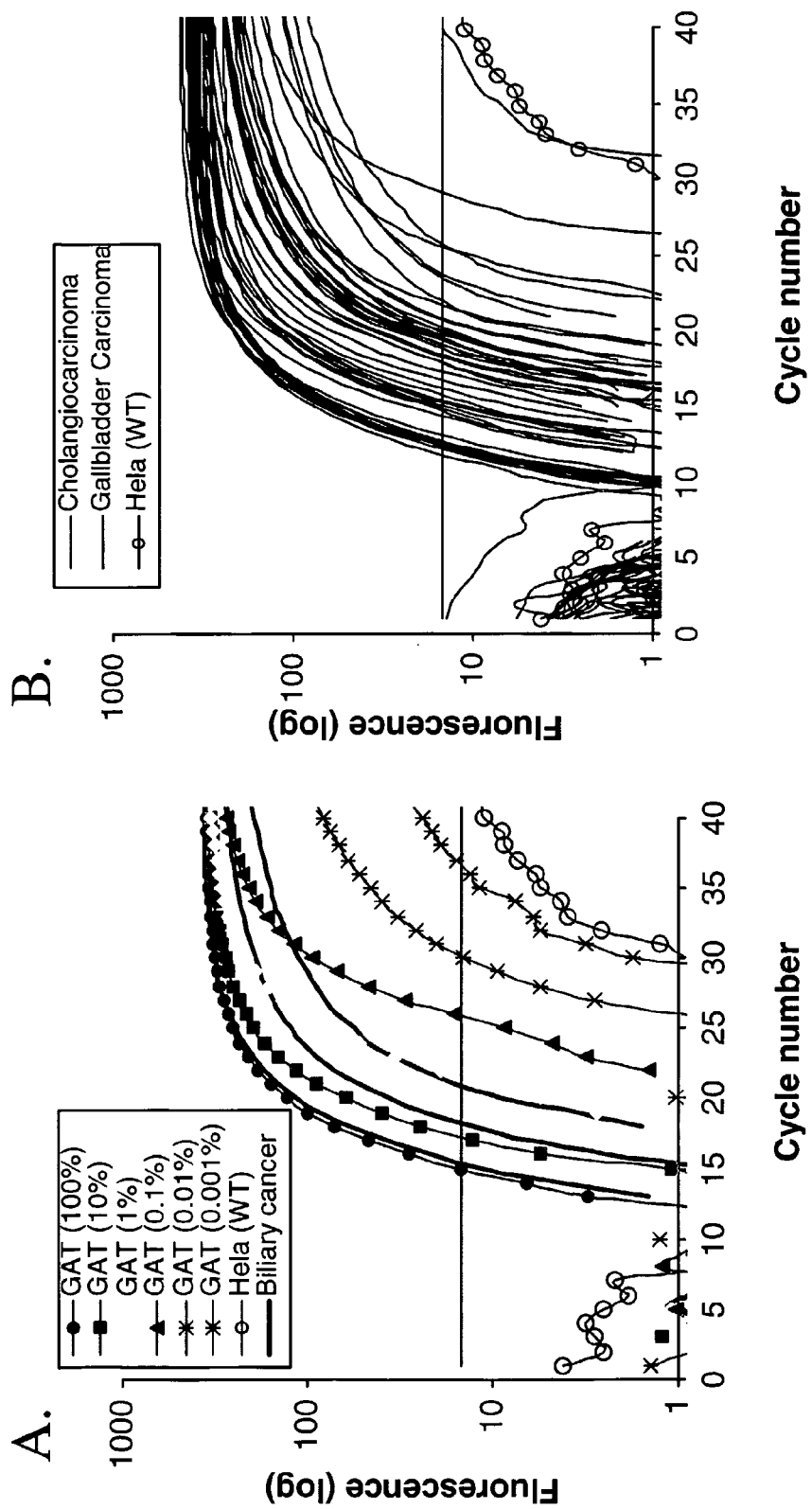

FIG. 20 depicts LigAmp analysis of GAT KRAS2 mutations in biliary tract cancers. A. Representative amplification curves for mutant DNA mixtures and three cancer samples (blue lines). Mutant DNA mixtures were made by serial dilution of mutant GAT KRAS2 into the wild type DNA. B. Amplification curves for primary tumors including 23 intrahepatic and extrahepatic cholangiocarcimas (blue lines) and 31 gallbladder carcinomas (red lines). PCR amplified DNA (600 pg) was used for LigAmp. One sample from a gallbladder cancer patient overlapped with the wild type signal. No amplification curves were obtained from three additional gallbladder cancer patient samples.

Figure 21:
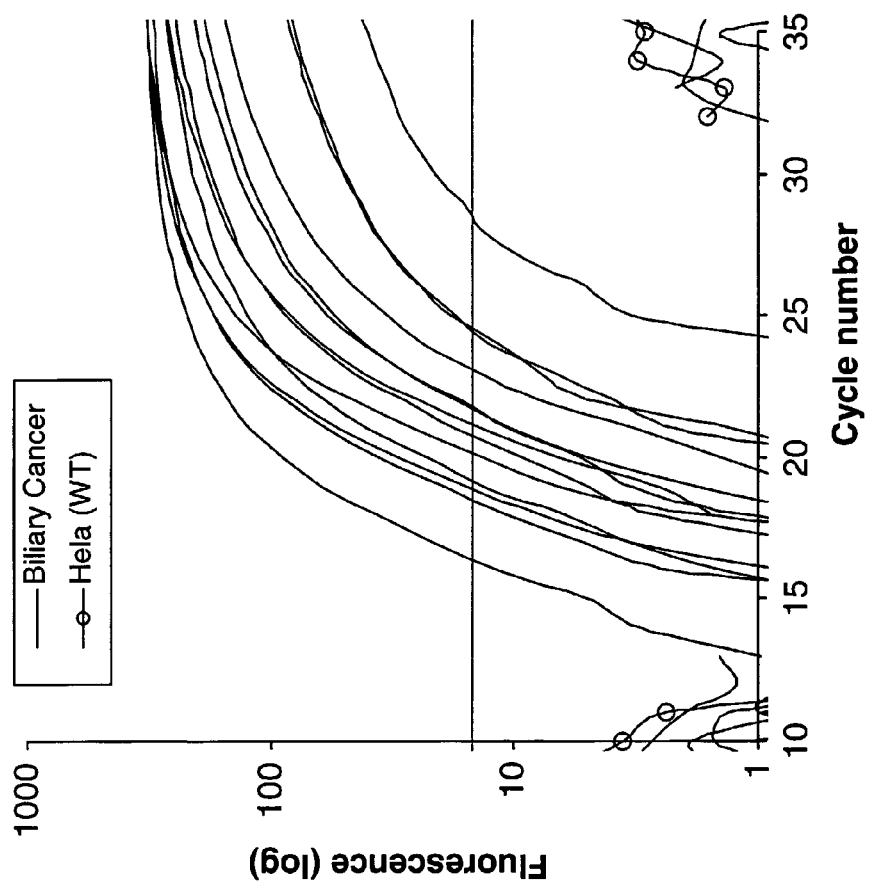

FIG. 21 depicts LigAmp analysis of GAT KRAS2 mutations in bile from biliary tract cancer patients (n=16). Amplification curves were obtained in 13 of 16 bile samples.

Figure 22:
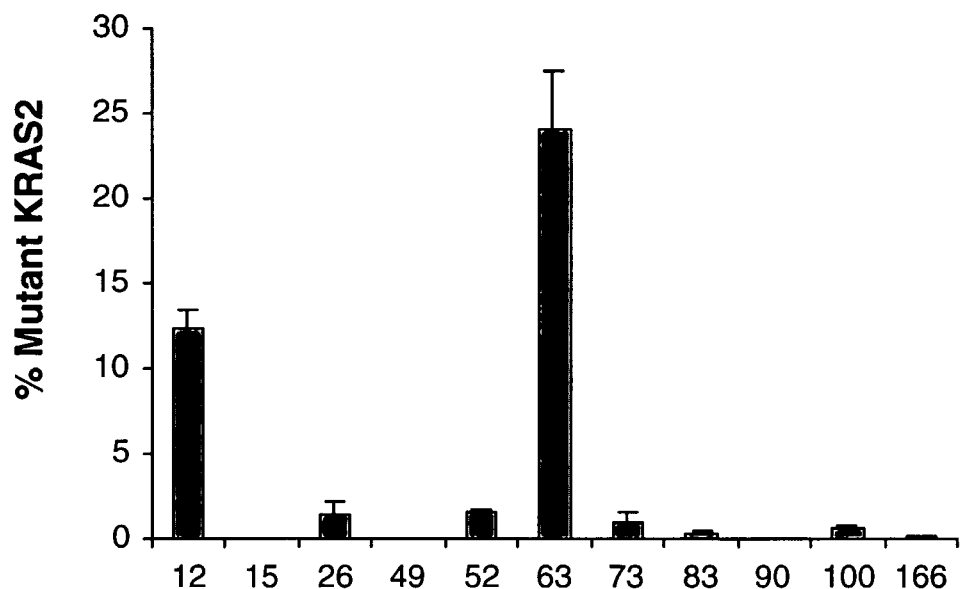
Figure 22:
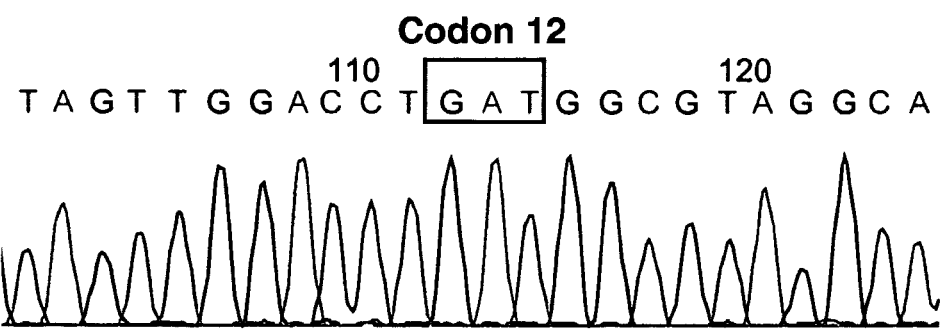

FIG. 22 depicts detection of the GAT KRAS2 mutation in serum from biliary tract cancer patients. A. The relative amount of the mutant to wild-type KRAS2 DNA in serum detected by LigAmp. Error bars are 1 standard deviation from 3 independent LigAmp assays. B. DNA sequence (SEQ ID NO: 41) of the cloned BstN1 refractory PCR product from sample 166, confirming the existence of a low level GAT mutation.

Figure 23:
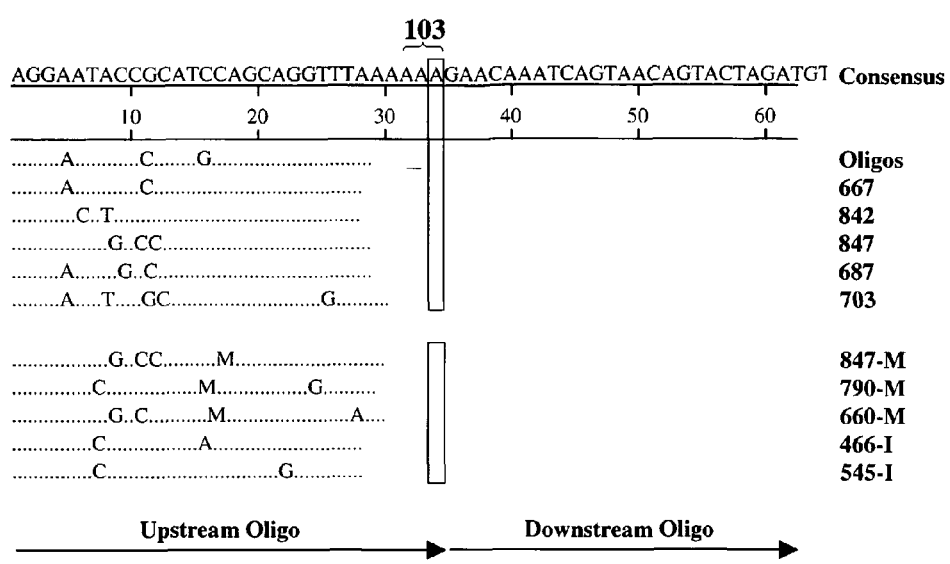
Figure 23:
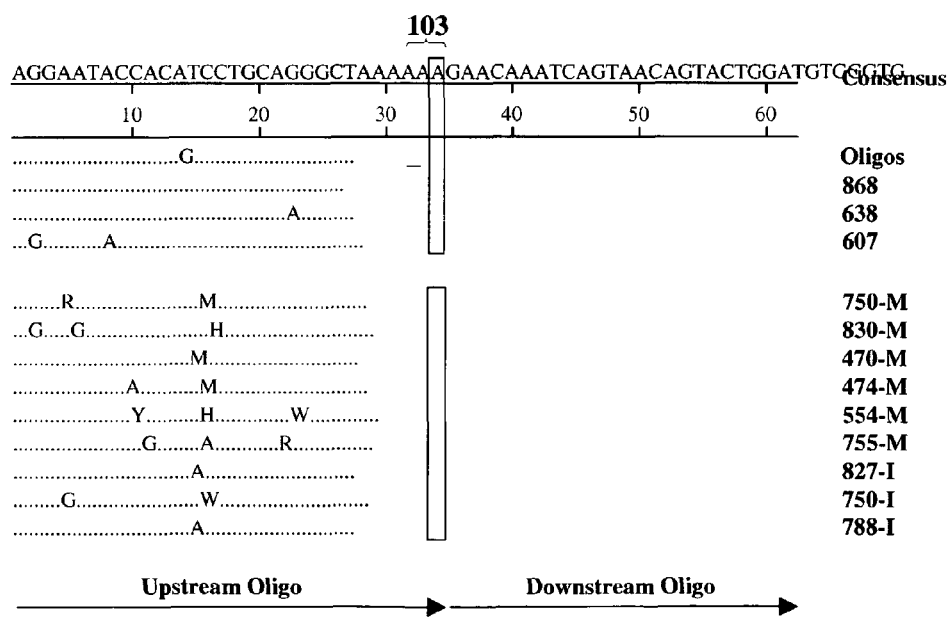

FIG. 23. Depicts HIV-1 sequences (SEQ ID NOS 43-53 and 55-67, respectively, in order of appearance) from Ugandan women and infants. Paired plasmids with and without the K103N mutation were used as reference reagents to optimize the LigAmp assay for detection of K103N in subtype A and D HIV-1. The sequences of five subtype A plasmids (Panel A, 667, 842, 847, 687 and 703) and three subtype D plasmids (Panel B, 868, 638, 607) are shown (control plasmids with K103N).

Nucleotides at the third position of codon 103 (bracket) are boxed. The sequences of the binding regions of the ligation oligonucleotides used in the first step of the LigAmp assay are shown at the top of each alignment (Oligos). An A→G substitution at the first base of codon 103 in the upstream oligonucleotide (underlined) enhances specificity of the ligation reaction. The lower section of each alignment shows sequences obtained using the ViroSeq system (population sequences) from Ugandan women (M) and infants (I) 6-8 weeks after single dose NVP. A consensus sequence (SEQ ID NOS 42 and 54, respectively, in order of appearance) is shown above each alignment. Dots indicate nucleotides that match the consensus sequence. Nucleotide mixtures are indicated using IUB codes: M=A+C, R=A+G, Y=C+T, H=A+C+T, W=A+T.

Figure 24:
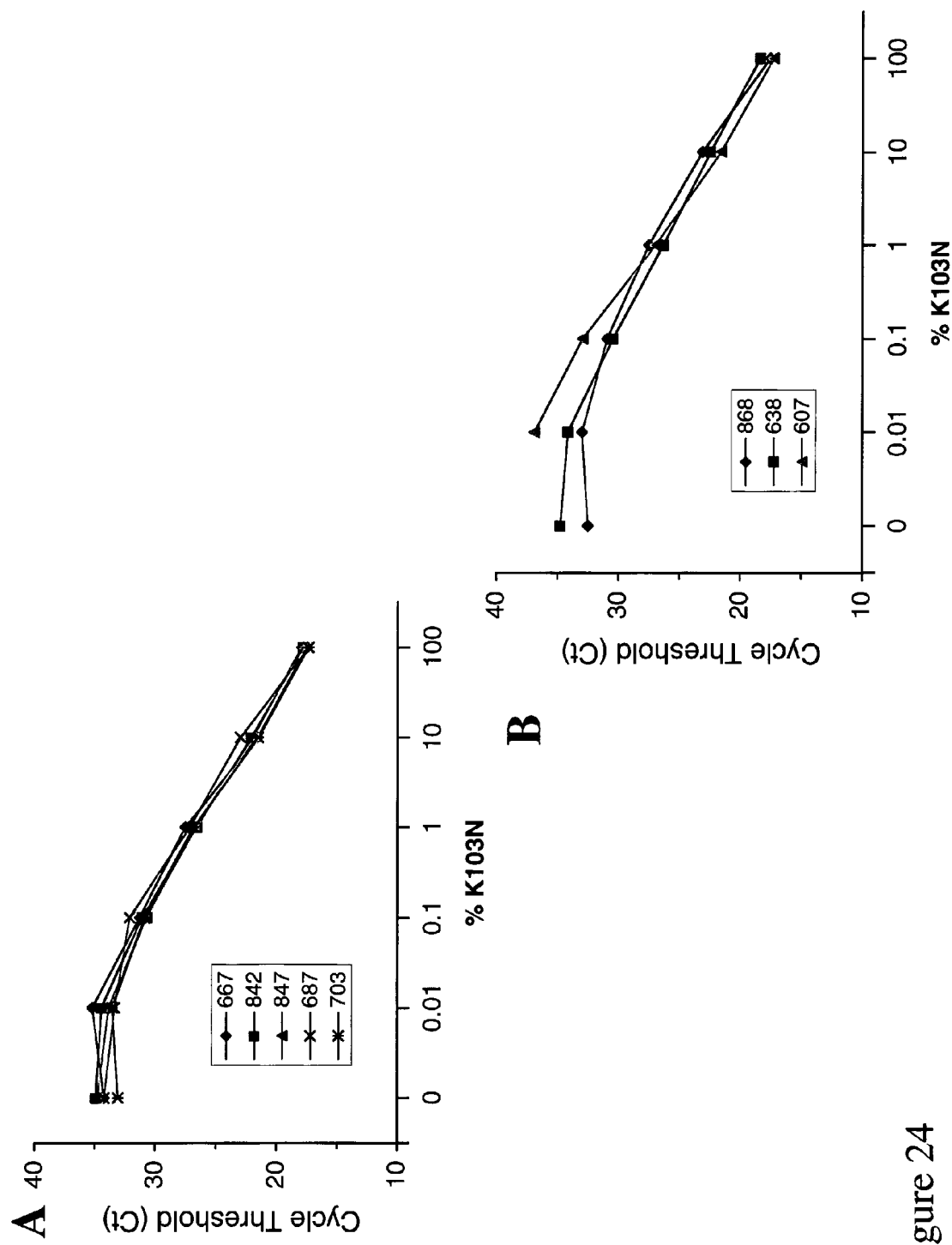
Figure 24:
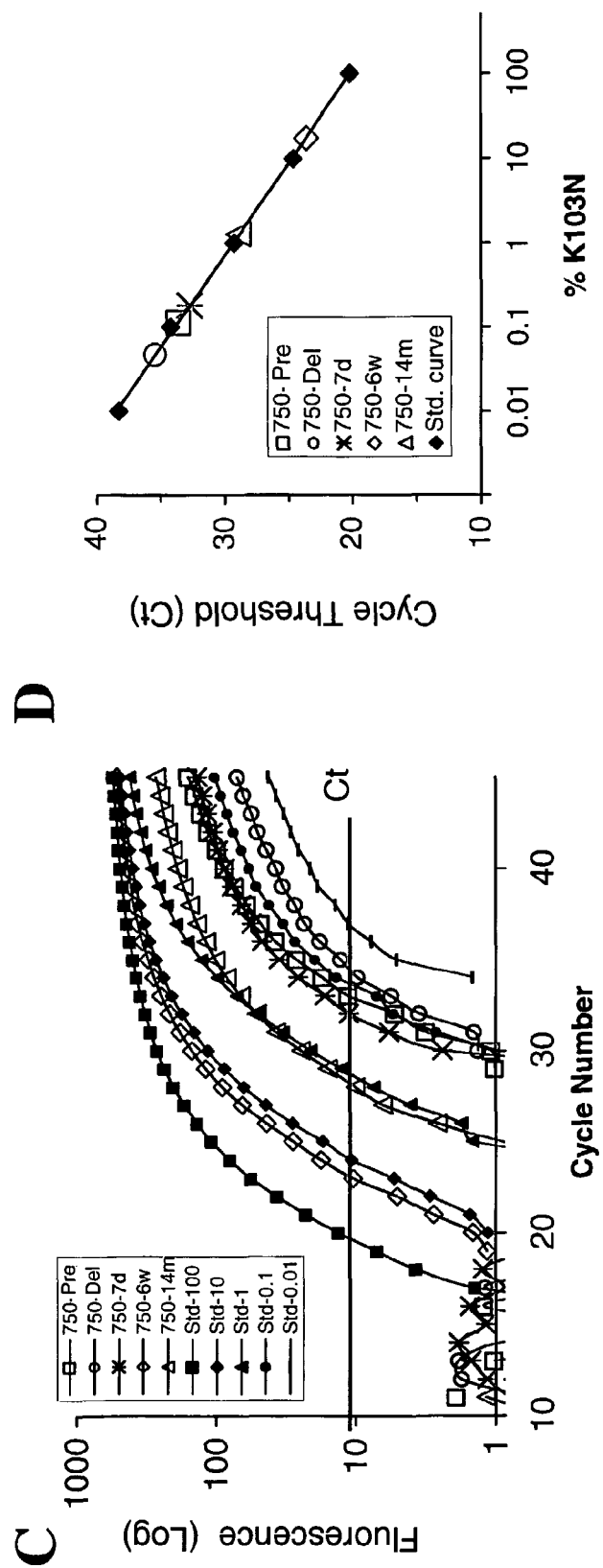

FIG. 24 depicts the analysis of control plasmids and a representative plasma sample using the LigAmp assay, and demonstrate that the LigAmp reaction is sensitive to the level of mutation present, but insensitive to "private" mutations near the ligation site within a given patient. Panels A and B illustrate performance of the LigAmp assay for detection of K103N in subtype A and D HIV-1 using control plasmids. Paired plasmids with and without the K103N mutation were used as reference reagents. The pol region of each plasmid was amplified and mixtures of mutant and wild-type DNA were prepared at mutant DNA concentrations of 100%, 10%, 1%, 0.1%, 0.01% and 0%. Standard curve dilution panels were generated using paired plasmids from five women with subtype A and three women with subtype D (see FIG. 23). Each standard curve was analyzed using the LigAmp assay and the % K103N in each sample was plotted against the cycle threshold (Ct) achieved in the real-time PCR detection step of the LigAmp assay (Panel A: subtype A controls, Panel B: subtype D controls). Standard curves generated for the dilution panels for each subtype were nearly identical, despite differences in the HIV-1 sequences of the templates at the ligation oligonucleotide binding regions. Results obtained for the wild type control (0% K103N) were similar for those obtained with the 0.01% K103N controls. In some experiments, either the 0% control sample or the 0.01% control sample failed to achieve threshold.

Panels C and D show representative results from one experiment (analysis of the K103N mutation in woman M-750). The plot in Panel C shows fluorescent detection of the K103N mutation in the real-time PCR detection step of the LigAmp assay. The cycle threshold is indicated (horizontal line). Results from the analysis of an internal standard curve (10-fold dilutions of DNA containing the K103N mutation) are shown in blue (Std. 0.01-100). None of the three negative controls included in the experiment achieved cycle threshold (the 0% K103N control sample, the ligation control (no template), and the real-time PCR control (no template), data not shown). Results from analysis of samples from one woman (M-750) are shown in red (Pre: pre-NVP; Del: delivery; 7 d: 7 days after single dose NVP; 6 w: 6 weeks after single dose NVP, 14 mo: 14 months after single dose NVP). Panel D shows results from panel C plotted as the percentage of HIV-1 variants with the K103N mutation (% K103N) vs. cycle threshold. The standard curve (Std. curve, blue) was used to determine the % K103N in each plasma sample. Note that the highest % K103N was seen in the 6-week visit (open diamond), but that the % K103N was also elevated above baseline 14 months after single dose NVP (open triangle). The experiment shown in Panels C and D was performed in triplicate, and results from those experiments were included in the data presented in FIG. 4 (data from M-750).

Figure 25:
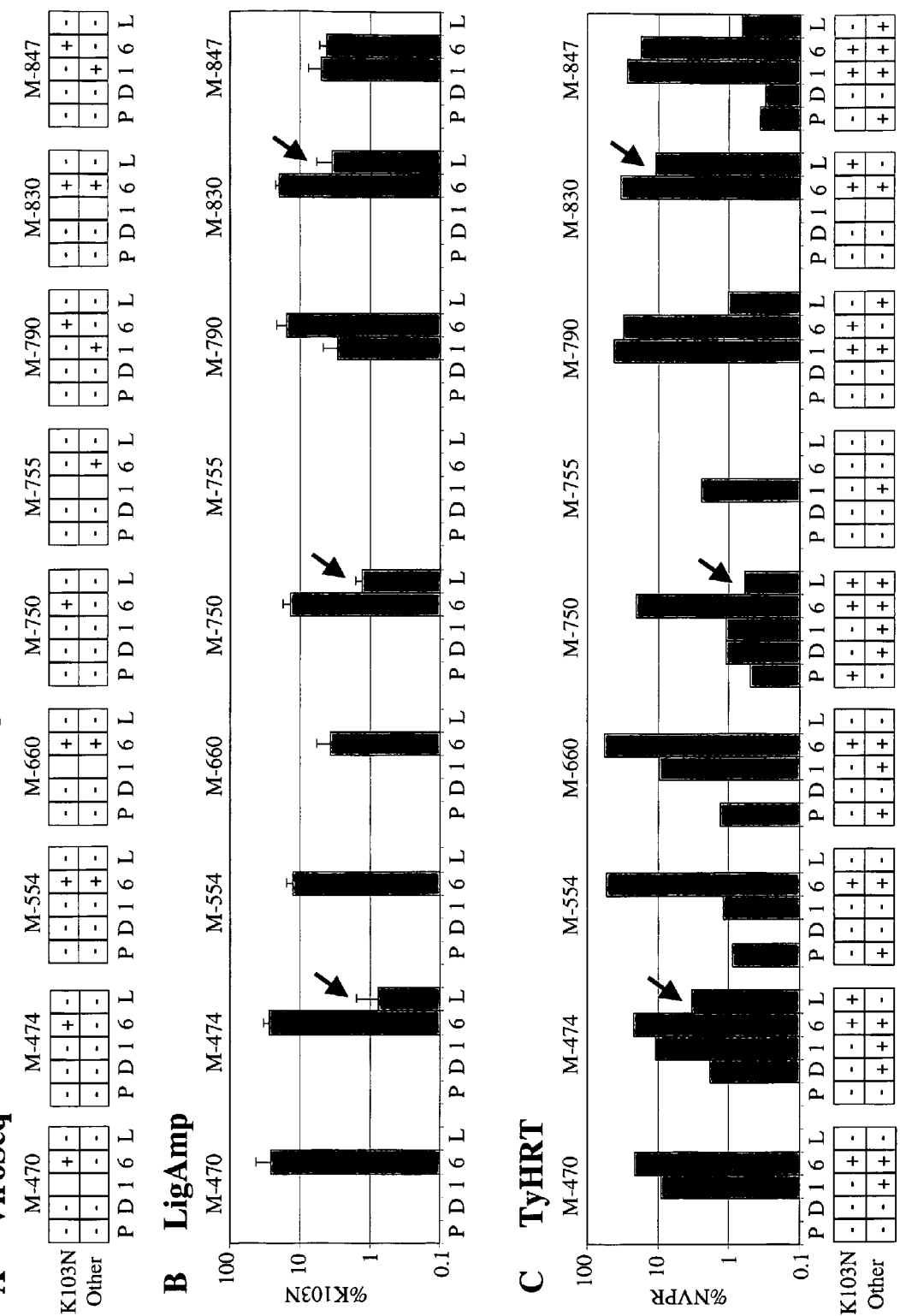

FIG. 25 depicts the analysis of HIV-1 in maternal samples. Samples from women (M) were collected prior to NVP (P), at delivery (D), and at 7 days (1 week, 1), 6-8 weeks (6) and 12, 14 or 24 months (long-term follow-up, L) after delivery. The 7-day samples from three women failed to amplify sufficiently for genotyping (M-470, M-660 and M-755) and one woman (M-830) did not have a 7-day sample available for analysis. Three women had subtype A HIV-1 (M-847, M-790, M-660 and three women had subtype D HIV-1 (M-470, M-554, M-755). Panel A: Analysis of samples with the ViroSeq assay. The presence (+) or absence (−) of K103N or other NVPR mutations in each sample is indicated. All of the NVPR mutations detected in women were detected as mixtures with wild type viruses. When K103N was detected, it was exclusively or predominantly encoded by the codon, AAC. The alternative codon, AAT, was present at a low level along with AAC in some samples. Panel B: Analysis of samples with the LigAmp assay. The percentage of variants with the K103N mutation was determined in triplicate for each sample using the LigAmp assay (% K103N). The mean and standard deviation from the three experiments are shown. Arrows indicate persistence of K103N above pre-NVP levels. Panel C: Analysis of samples using the TyHRT assay. In the TyHRT assay, HIV-1 pol region DNA from each sample is introduced into a yeast element by homologous recombination. Each yeast isolate carries a unique HIV-1 RT domain and the library of isolates is representative of the RT domains present in the original viral sample. Yeast are cultured in the presence of NVP to isolate NVPR colonies. The percentage of yeast colonies (HIV-1 variants) with NVPR is plotted for each sample (% NVPR). DNA was isolated from individual NVPR colonies and sequenced to identify NVPR mutations in the HIV-1 RT domain. The presence (+) or absence (−) of K103N or other NVPR mutations in clones isolated from each sample is indicated below the graph. A more detailed description of this analysis can be found on-line (insert web address here).

Figure 26:
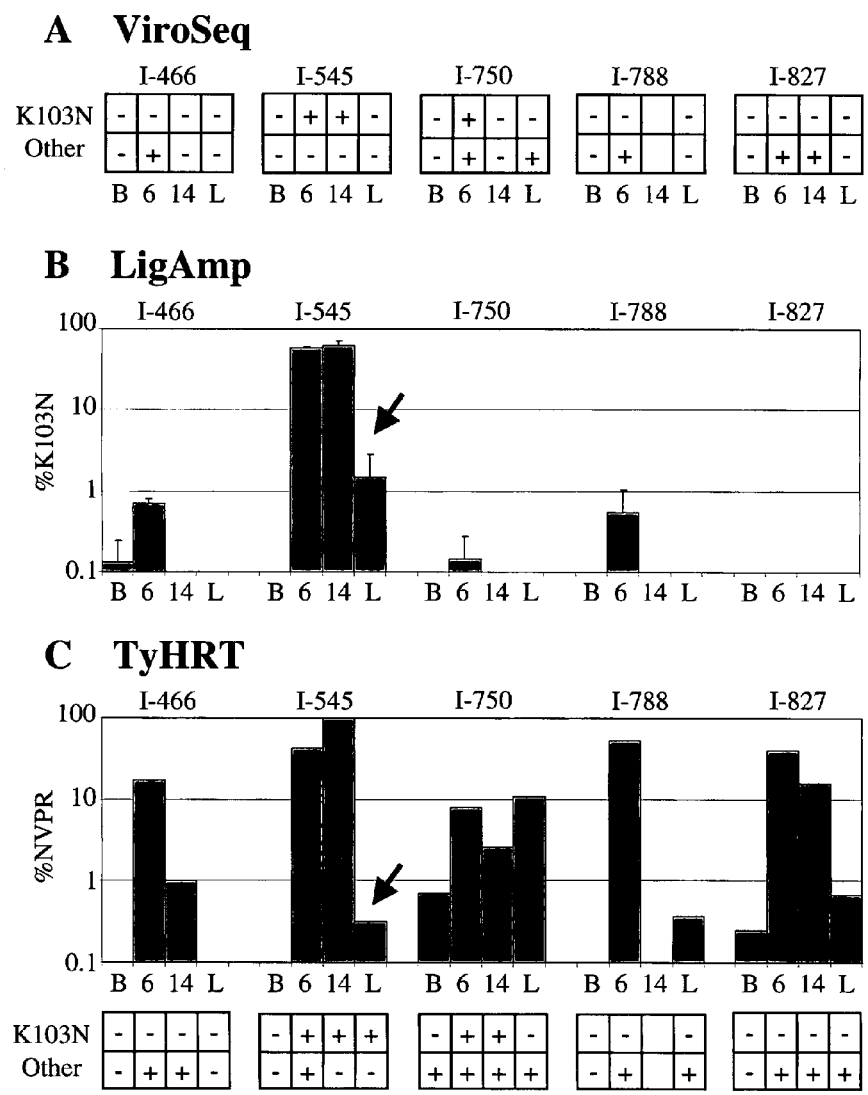

FIG. 26 depicts the analysis of HIV-1 in samples from infants. Samples from infants (I) were collected at birth (B), and at 6-8 weeks (6), 14-16 weeks (14) and 12 months (long-term follow-up, L) after delivery. One infant (I-788) did not have a 14-16-week sample available for analysis. One infant had subtype A HIV-1 (I-466) and three infants had subtype D HIV-1 (I-827, I-750, I-788). Panel A: Analysis of samples with the ViroSeq assay. The presence (+) or absence (−) of K103N or other NVPR mutations in each sample is indicated. All of the NVPR mutations detected in infants were detected as mixtures with wild type viruses with the exception of the K103N mutation in the 6-8 week and 14 week samples from infant I-545. When K103N was detected, it was exclusively or predominantly encoded by the codon, AAC, with one exception: K103N was encoded predominantly by AAT in the 6-8 week sample from infant I-750. Panel B: Analysis of samples with the LigAmp assay (see legend for FIG. 25, Panel B). Panel C: Analysis of samples using the TyHRT assay (see legend for FIG. 25, Panel C).

Figure 27:
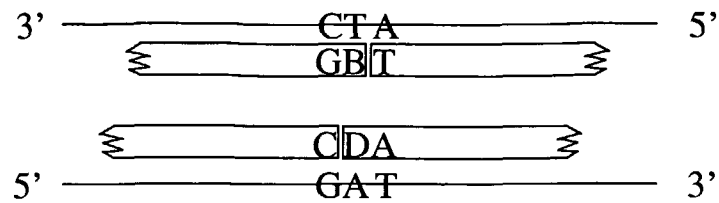
Figure 27:
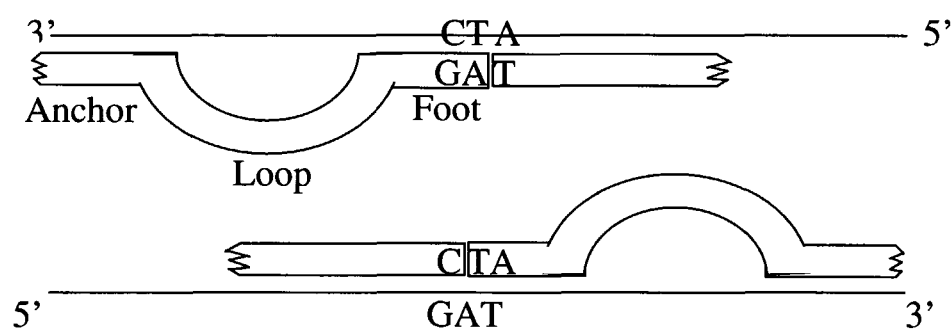
Figure 27:
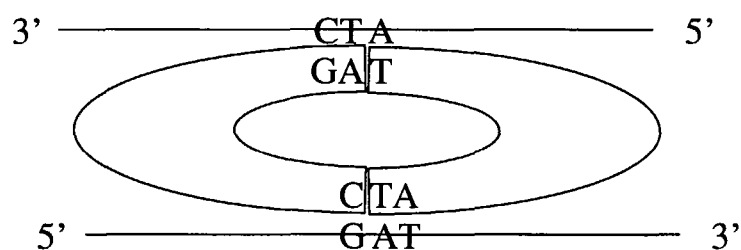
Figure 27:
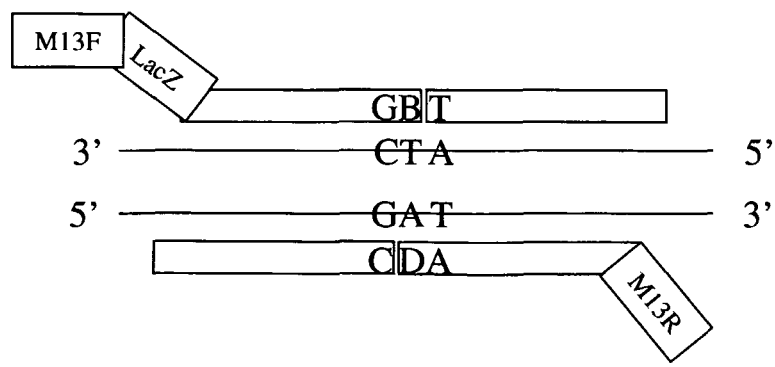

FIG. 27 depicts double LigAmp assays. A. Pseudocomplementary or Aegis bases. Two separate LigAmp reactions are shown on both strands using the model of a KRAS2 codon 12 mutation (GGT-->GAT). The 3' end of the upstream oligonucleotide is placed on the mutant base in both cases. In the top reaction, the symbol B in the upstream oligonucleotide represents an artificial base (instead of native Adenine), which retains its ability to pair with thymidine and its ability to be ligated to the thymidine in the downstream oligonucleotide. In the bottom reaction the D represents a modified base that retains its ability to bind to native adenine and be ligated to the downstream oligonucleotide. Bases B and D however are unable to interact with one another thereby preventing the 4 primers from participating in a ligase chain reaction. The zigzag line represents an interrupted end of the oligonucleotide. B. Loops preventing Ligase chain reactions. In this modification, loops are used in two of the oligonucleotides to prevent ligase chain reactions from occurring. See text. Symbols as in A. C. Circularization requires two different ligation events. The oligonucleotides now contain regions complementary to both targets. To produce a closed circle would require ligation on both strands of target DNA. Detection could then proceed using standard Q-PCR, via rolling circle amplification or via hyper-branched (bi-directional) rolling circle amplification. D. In this modification, the probe is only in the upstream ligation pair. Neither pair of oligonucleotides contains both the M13 forward and reverse primers. Therefore during the realtime PCR reaction using these primers, both ligation events had to have occurred (and extension from them) to produce a molecule capable of being amplified.

DETAILED DESCRIPTION OF THE INVENTION

Provided herein are simple, universal strategies for sensitive detection and quantification of nucleotide differences, e.g., single base differences, single nucleotide polymorphisms (SNP), and minority disease variants. The methods provided herein, for the first time, allow simple, quick, accurate, and sensitive methods for determining the nucleotide differences.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

Certain Definitions

The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR$_2$ or halogen groups, where each R is independently H, $C_1$-$C_6$ alkyl or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14) aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-.alpha.-anomeric nucleotides, 1'-.alpha.-anomeric nucleotides, 2'-4'- and 3'-4'-linked and other "locked" or "LNA," bicyclic sugar modifications (see, e.g., PCT published application nos. WO 98/22489, WO 98/39352; and WO 99/14226).

As used herein, the terms "polynucleotide," "oligonucleotide," and "nucleic acid" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., H$^+$, NH$_4^+$, trialkylammonium, Mg$^{2+}$, Na$^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotide analogs. nucleic acids typically range in size from a few monomeric units, e.g. 5-40 when they are sometimes referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, and "T" denotes thymidine or an analog thereof, unless otherwise noted.

Nucleic acids include, but are not limited to, genomic DNA, cDNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample.

Nucleic acids may be composed of a single type of sugar moiety, e.g., as in the case of RNA and DNA, or mixtures of different sugar moieties, e.g., as in the case of RNA/DNA chimeras.

The terms "nucleic acid," "polynucleotide," and "oligonucleotide" may also include nucleic acid analogs, polynucleotide analogs, and oligonucleotide analogs. The terms "nucleic acid analog," "polynucleotide analog" and "oligonucleotide analog" are used interchangeably and, as used herein, refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, Science 254:1497-1500; WO 92/20702; U.S. Pat. Nos. 5,719,262; 5,698,685;); morpholinos (see, e.g., U.S. Pat. Nos. 5,698,685; 5,378,841; 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'-thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254:1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

An "enzymatically active mutant or variant thereof," when used in reference to an enzyme such as a polymerase or a ligase, means a protein with appropriate enzymatic activity. Thus, for example, but without limitation, an enzymatically active mutant or variant of a DNA polymerase is a protein that is able to catalyze the stepwise addition of appropriate deoxynucleoside triphosphates into a nascent DNA strand in a template-dependent manner. An enzymatically active mutant or variant differs from the "generally-accepted" or consensus sequence for that enzyme by at least one amino acid, including, but not limited to, substitutions of one or more amino acids, addition of one or more amino acids, deletion of one or more amino acids, and alterations to the amino acids themselves. With the change, however, at least some catalytic activity is retained. In certain embodiments, the changes involve conservative amino acid substitutions. Conservative amino acid substitution may involve replacing one amino acid with another that has, e.g., similar hydorphobicity, hydrophilicity, charge, or aromaticity. In certain embodiments, conservative amino acid substitutions may be made on the basis of similar hydropathic indices. A hydropathic index takes into account the hydrophobicity and charge characteristics of an amino acid, and in certain embodiments, may be used as a guide for selecting conservative amino acid substitutions. The hydropathic index is discussed, e.g., in Kyte et al., J. Mol. Biol., 157:105-131 (1982). It is understood in the art that conservative amino acid substitutions may be made on the basis of any of the aforementioned characteristics.

Alterations to the amino acids may include, but are not limited to, glycosylation, methylation, phosphorylation, biotinylation, and any covalent and noncovalent additions to a protein that do not result in a change in amino acid sequence. "Amino acid" as used herein refers to any amino acid, natural or non-natural, that may be incorporated, either enzymatically or synthetically, into a polypeptide or protein.

Fragments, for example, but without limitation, proteolytic cleavage products, are also encompassed by this term, provided that at least some enzyme catalytic activity is retained.

Protocols for polymerase and ligase activity assays may be found, among other places, in Sambrook et al., Molecular Cloning, A Laboratory Manual, Cold Spring Harbor Press (1989) (hereinafter "Sambrook et al."), Sambrook and Russell, Molecular Cloning, Third Edition, Cold Spring Harbor Press (2000) (hereinafter "Sambrook and Russell"), Ausbel et al., Current Protocols in Molecular Biology (1993) including supplements through April 2001, John Wiley & Sons (hereinafter "Ausbel et al.").

A "nucleic acid sample" or "nucleic acid sample" according to the present invention comprises a specific nucleic acid sequence that can be distinguished by a probe. Nucleic acid samples may include both naturally occurring and synthetic molecules.

As used herein, "plurality" in reference to oligonucleotide probes includes sets of two or more oligonucleotide probes where there may be a single "common" oligonucleotide probe that is usually specific for a non-variable region of a target polynucleotide and one or more "wild-type" and/or "mutant" oligonucleotide probes that are usually specific for a region of a target polynucleotide that contains allelic or mutational variants in sequence.

As used herein, "nucleoside" includes the natural nucleosides, including 2'-deoxy and 2'-hydroxyl forms, e.g. as described in Komberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990); or the like. Such analogs include synthetic nucleosides designed to enhance binding properties, reduce degeneracy, increase specificity, and the like. The term "amplification primer," as used herein, refers to an oligonucleotide which either (i) acts to initiate synthesis of a complementary DNA strand when placed under conditions in which synthesis of a primer extension product is induced, i.e., in the presence of nucleotides and a polymerization-inducing agent such as a DNA-dependent DNA polymerase and at suitable temperature, pH, metal concentration, and salt concentration, or (ii) is ligated to another amplification primer in a ligation-based amplification scheme. Amplification primers are from 30 to 50 nucleotide long and have Tm's between 80° C. and 120° C. Preferably, such amplification primers are employed with a first annealing temperature of between about 72° C. to about 84° C. More preferably, the first annealing temperature is between about 72° C. to about 75° C. Preferably, the oligonucleotide probes used in the OLA are from 8 to 30 nucleotides long and have Tm's between 40° C. and 70° C. Such oligonucleotide probes are preferably used with a second annealing temperature between about 30° C. to about 55° C., and more preferably, between about 40° C. to about 55° C. Preferably, annealing temperatures are selected to ensure specificity in amplification and detection. Typically, annealing temperatures are selected in the range of from 1-2° C. above or below the melting temperature of an amplification primer or oligonucleotide probe to about 5-10° C. below such temperature. Guidance for selecting appropriate primers or oligonucleotides given these design constraints and the nature of the polynucleotide targets can be found in many references, including Rychlik et al. (1989) Nucl. Acids. Res. 17:8453-8551; Lowe et al. (1990) Nucl. Acids Res. 18:1757-1761, Hiller et al. (1991) PCR Methods and Applications 1:124-128; Wetmur, Critical Reviews in Biochemistry and Molecular Biology, 26: 227-259 (1991); Breslauer et al, Proc. Natl. Acad. Sci. 83: 3746-3750 (1986); Innis et al, editors, PCR Protocols (Academic Press, New York, 1990); and the like.

"Pooled nucleic acid sample" refers to a pool of samples, a pool of a pool of samples, a pool of a pool of a pool of samples, and the like. For example, a small portion of ten blood donations are mixed together forming a pool.

CFTR mutations that may be identified by methods described herein, include, for example, G542X, G551D, .DELTA.F508, W1282X, N1303, 3905insT and 3849+10kbCT, or 3849+4AG, 3659delC, R117H, R1162X 117-1GT, 621+1GT R553X and 2789+5GA.

"Detecting infectious disease minority variants," as used herein refers to the substitution in the viral genome associated with altered susceptibility to one or more antiviral drugs such as those cited in Johnson et al, "Update of the drug resistance mutations in HIV-1: 2004. Topics in HIV Medicine, Vol 12, pp 119-124, 2004. Any variation identified may be identified with the methods described herein.

"Probes," according to the present invention, comprise oligonucleotides that comprise a specific portion that is designed to hybridize in a sequence-specific manner with a complementary region on a specific nucleic acid sequence, e.g., a nucleic acid sample. In certain embodiments, the specific portion of the probe may be specific for a particular sequence, or alternatively, may be degenerate, e.g., specific for a set of sequences.

The oligonucleotides of the invention may also be considered "oligonucleotide sets." Oligonucleotides, e.g., P1 and P2, according to the present invention are probes designed to detect at least one nucleic acid sample or target. As a non-limiting example, an oligonucleotide set may comprise two nucleic acid probes designed to hybridize to a target such that, when the two probes are hybridized to the target adjacent to one another, they are suitable for ligation together.

When used in the context of the present invention, "suitable for ligation" refers to at least one first gene specific region probe and at least one second gene specific region probe, each comprising an appropriately reactive group. Exemplary reactive groups include, but are not limited to, a free hydroxyl group on the 3' end of the first probe region and a free phosphate group on the 5' end of the second probe region. Exemplary pairs of reactive groups include, but are not limited to: phosphorothioate and tosylate or iodide; esters and hydrazide; RC(O)S—, haloalkyl, or RCH$_2$S and alpha-haloacyl; thiophosphoryl and bromoacetoamido groups. Exemplary reactive groups include, but are not limited to, S-pivaloyloxymethyl-4-thiothymidine. Additionally, in certain embodiments, first and second gene specific region probes are hybridized to the target sequence such that the 3' end of the first gene specific region probe and the 5' end of the second gene specific region probe are immediately adjacent to allow ligation.

The term "signal moiety" as used herein refers to any tag, label, or identifiable moiety. "Detectably different signal" means that detectable signals from different signal moieties are distinguishable from one another by at least one detection method.

The term "detectable signal value" refers to a value of the signal that is detected from a label. In certain embodiments, the detectable signal value is the amount or intensity of signal that is detected from a label. Thus, if there is no detectable signal value from a label, its detectable signal value is zero (0). In certain embodiments, the detectable signal value is a characteristic of the signal other than the amount or intensity of the signal, such as the spectra, wavelength, color, or lifetime of the signal.

"Detectably different signal value" means that one or more detectable signal values are distinguishable from one another by at least one detection method.

The term "labeled probe" refers to a probe that provides a detectably different signal value depending upon whether a given nucleic acid sequence is present or absent. In certain embodiments, a labeled probe provides a detectably different signal value when the intact labeled probe is hybridized to a given nucleic acid sequence than when the intact labeled probe is not hybridized to a given nucleic acid sequence. Thus, if a given nucleic acid sequence is present, the labeled probe provides a detectably different signal value than when the given nucleic acid sequence is absent. In certain embodiments, a labeled probe provides a detectably different signal value when the probe is intact than when the probe is not intact. In certain such embodiments, a labeled probe remains intact unless a given nucleic acid sequence is present. In certain such embodiments, if a given nucleic acid sequence is present, the labeled probe is cleaved, which results in a detectably different signal value than when the probe is intact.

In certain embodiments, the labeled probe is an "interaction probe." The term "interaction probe" refers to a probe that comprises at least two moieties that can interact with one another to provide a detectably different signal value depending upon whether a given nucleic acid sequence is present or absent. The signal value that is detected from the interaction probe is different depending on whether the two moieties are sufficiently close to one another or are spaced apart from one another. During the methods described herein, the proximity of the two moieties to one another is different depending upon whether the given nucleic acid is present or absent.

The term "quantitating," when used in reference to an amplification product, refers to determining the quantity or amount of a particular sequence that is representative of a nucleic acid sample in the sample. For example, but without limitation, one may measure the intensity of the signal from a labeled probe. The intensity or quantity of the signal is typically related to the amount of amplification product. The amount of amplification product generated correlates with the amount of nucleic acid sample present prior to ligation and amplification, and thus, in certain embodiments, may indicate the level of expression for a particular gene.

Nucleic acid samples of the invention may contain from between about a 1:1 to about a 1:100,000 ratio of mutated nucleic acid to wild type nucleic acid. For some applications, for example, routine genotyping, there is expected to be a 1:1 molar ratio, i.e. a heterozygote. For the detection of infectious disease minority variant detection, there may be a ratio of from between about 1:3 to about a 1:100,000 ratio of mutated to wild-type nucleic acid. Other ratios and ranges of ratios will vary considerably depending on the specific application and specimen at hand. For example, for early detection of pancreas cancer in pancreatic duct juice, percentages of mutant DNA may vary from 0.5% to 80% of total KRAS2 DNA. When detected in peripheral blood, the levels will likely be considerably smaller ranging from 1:1,000 to 1:1,000,000. The term "amplification product" as used herein refers to the product of an amplification reaction including, but not limited to, primer extension, the polymerase chain reaction, RNA transcription, and the like. Thus, exemplary amplification products may comprise at least one of primer extension products, PCR amplicons, RNA transcription products, and the like.

"Primers" according to the present invention refer to oligonucleotides that are designed to hybridize with the primer region of probes, ligation products, or amplification products in a sequence-specific manner, and serve as primers for amplification reactions.

A "universal primer" is capable of hybridizing to the primer region of more than one species of probe, ligation product, or amplification product, as appropriate. A "universal primer set" comprises a first primer and a second primer that hybridize with a plurality of species of probes, ligation products, or amplification products, as appropriate.

A "ligation agent" according to the present invention may comprise any number of enzymatic or chemical (i.e., non-enzymatic) agents that can effect ligation of nucleic acids to one another.

"Blocking probe," as used herein refers to a nucleic acid probe that is complementary to the nucleic acid target sequence and contains the nucleic acid difference. For example, the probe may contain the wild-type sequence complementary to the nucleic acid difference being detected and overlap with both the sequence of P1 and P2.

In this application, a statement that one sequence is the same as or is complementary to another sequence encompasses situations where both of the sequences are completely the same or complementary to one another, and situations where only a portion of one of the sequences is the same as, or is complementary to, a portion or the entire other sequence. Here, the term "sequence" encompasses, but is not limited to, nucleic acid sequences, polynucleotides, oligonucleotides, probes, primers, primer regions, gene specific regions, addressable portions, and oligonucleotide link elements.

In this application, a statement that one sequence is complementary to another sequence encompasses situations in which the two sequences have mismatches. Here, the term "sequence" encompasses, but is not limited to, nucleic acid sequences, polynucleotides, oligonucleotides, probes, primers, primer regions, gene specific regions, addressable portions, and oligonucleotide link elements. Despite the mismatches, the two sequences should selectively hybridize to one another under appropriate conditions.

The term "selectively hybridize" means that, for particular identical sequences, a substantial portion of the particular identical sequences hybridize to a given desired sequence or sequences, and a substantial portion of the particular identical sequences do not hybridize to other undesired sequences. A "substantial portion of the particular identical sequences" in each instance refers to a portion of the total number of the particular identical sequences, and it does not refer to a portion of an individual particular identical sequence. In certain embodiments, "a substantial portion of the particular identical sequences" means at least 90% of the particular identical sequences. In certain embodiments, "a substantial portion of the particular identical sequences" means at least 95% of the particular identical sequences.

In certain embodiments, the number of mismatches that may be present may vary in view of the complexity of the composition. Thus, in certain embodiments, fewer mismatches may be tolerated in a composition comprising DNA from an entire genome than a composition in which fewer DNA sequences are present. For example, in certain embodiments, with a given number of mismatches, a probe may more likely hybridize to undesired sequences in a composition with the entire genomic DNA than in a composition with fewer DNA sequences, when the same hybridization conditions are employed for both compositions. Thus, that given number of mismatches may be appropriate for the composition with fewer DNA sequences, but fewer mismatches may be more optimal for the composition with the entire genomic DNA.

In certain embodiments, sequences are complementary if they have no more than 20% mismatched nucleotides. In certain embodiments, sequences are complementary if they have no more than 15% mismatched nucleotides. In certain embodiments, sequences are complementary if they have no more than 10% mismatched nucleotides. In certain embodiments, sequences are complementary if they have no more than 5% mismatched nucleotides. A portion of the sequences may be complementary while another portion is not. For example, the gene specific region may be complementary to the nucleic acid sample while the primer region is not complementary to the nucleic acid sample.

In this application, a statement that one sequence hybridizes or binds to another sequence encompasses situations where the entirety of both of the sequences hybridize or bind to one another, and situations where only a portion of one or both of the sequences hybridizes or binds to the entire other sequence or to a portion of the other sequence. Here, the term "sequence" encompasses, but is not limited to, nucleic acid sequences, polynucleotides, oligonucleotides, probes, primers, primer regions, gene specific regions, addressable portions, and oligonucleotide link elements.

In certain embodiments, the term "to a measurably lesser extent" encompasses situations in which the event in question is reduced at least 10 fold. In certain embodiments, the term "to a measurably lesser extent" encompasses situations in which the event in question is reduced at least 100 fold.

In certain embodiments, a statement that a component may be, is, or has been "substantially removed" means that at least 90% of the component may be, is, or has been removed. In certain embodiments, a statement that a component may be, is, or has been "substantially removed" means that at least 95% of the component may be, is, or has been removed.

In certain embodiments, nucleic acid samples may include RNA and DNA. Exemplary RNA target sequences include, but are not limited to, mRNA, rRNA, tRNA, viral RNA, and variants of RNA, such as splicing variants. Exemplary DNA target sequences include, but are not limited to, genomic DNA, viral DNA, plasmid DNA, phage DNA, nucleolar DNA, mitochondrial DNA, and chloroplast DNA.

In certain embodiments, nucleic acid samples include, but are not limited to, cDNA, yeast artificial chromosomes (YAC's), bacterial artificial chromosomes (BAC's), other extra chromosomal DNA, and nucleic acid analogs. Exemplary nucleic acid analogs include, but are not limited to, LNAs, PNAs, PPG's, Aegis bases and other nucleic acid analogs.

A variety of methods are available for obtaining a nucleic acid sample for use with the compositions and methods of the present invention. When the nucleic acid sample is obtained through isolation from a biological matrix, certain isolation techniques include, but are not limited to, (1) organic extraction followed by ethanol precipitation, e.g., using a phenol/chloroform organic reagent (e.g., Ausubel et al., eds., Current Protocols in Molecular Biology Volume 1, Chapter 2, Section I, John Wiley & Sons, New York (1993)), in certain embodiments, using an automated DNA extractor, e.g., the Model 341 DNA Extractor available from Applied Biosystems (Foster City, Calif.); (2) stationary phase adsorption methods (e.g., Boom et al., U.S. Pat. No. 5,234,809; Walsh et al., Biotechniques 10(4): 506-513 (1991)); and (3) salt-induced DNA precipitation methods (e.g., Miller et al., Nucleic Acids Research, 16(3): 9-10 (1988)), such precipitation methods being typically referred to as "salting-out" methods. In certain embodiments, the above isolation methods may be preceded by an enzyme digestion step to help eliminate unwanted protein from the sample, e.g., digestion with proteinase K, or other like proteases. See, e.g., U.S. patent application Ser. No. 09/724,613.

In certain embodiments, a nucleic acid sample may be derived from any living, or once living, organism, including but not limited to prokaryote, eukaryote, plant, animal, and virus. In certain embodiments, the nucleic acid sample may originate from a nucleus of a cell, e.g., genomic DNA, or may be extranuclear nucleic acid, e.g., plasmid, mitochondrial nucleic acid, various RNAs, and the like. In certain embodiments, if the sequence from the organism is RNA, it may be reverse-transcribed into a cDNA nucleic acid sample. Furthermore, in certain embodiments, the nucleic acid sample may be present in a double stranded or single stranded form.

Exemplary nucleic acid samples include, but are not limited to, amplification products, ligation products, transcription products, reverse transcription products, primer extension products, methylated DNA, and cleavage products. Exemplary amplification products include, but are not limited to, PCR and isothermal products.

In certain embodiments, nucleic acids in a sample may be subjected to a cleavage procedure. In certain embodiments, such cleavage products may be targets.

Different nucleic acid samples may target regions that are different portions of a single contiguous nucleic acid or may be on different nucleic acids. Different portions of a single contiguous nucleic acid may or may not overlap.

In certain embodiments, a nucleic acid sample comprises target region with an upstream or 5' region, a downstream or 3' region, and a "nucleotide difference" or a "pivotal nucleotide" located, for example, in the upstream region or the downstream region. In certain embodiments, the nucleotide difference may be the nucleotide being detected by the oligonucleotide set and may represent, for example, without limitation, a single polymorphic nucleotide in a multiallelic target locus, a disease minority variant, an SNP, and/or a mutation. In certain embodiments, more than one nucleotide difference are present. In certain embodiments, one or more nucleotide differences are located in the upstream region, and one or more nucleotide difference are located in the downstream region. In certain embodiments, more than one nucleotide difference is located in the upstream region or the downstream region.

The person of ordinary skill will appreciate that while a nucleic acid sample is typically described as a single-stranded molecule, the opposing strand of a double-stranded molecule comprises a complementary sequence that may also be used as a target sequence.

An oligonucleotide set, according to certain embodiments, comprises two or more oligonucleotides that comprise a gene specific region that is designed to hybridize in a sequence-specific manner with a complementary region on a specific nucleic acid sample. A gene specific region of an oligonucleotide of a set may further comprise a primer region, an addressable portion, all or part of a promoter or its complement, or a combination of these additional components. In certain embodiments, any of the oligonucleotide's components may overlap any other oligonuleotide component(s). For example, but without limitation, the gene specific region may overlap the primer region, the promoter or its complement, or both. Also, without limitation, the addressable portion may overlap with the gene specific region or the primer specific-portion, or both.

In certain embodiments, at least one oligonucleotide of a oligonucleotide set comprises the addressable portion located between the gene specific region and the primer region. In certain embodiments, the oligonucleotide addressable portion may comprise a sequence that is the same as, or is complementary to, at least a portion of a labeled probe. In certain embodiments, the oligonucleotide's primer region may comprise a sequence that is the same as, or is complementary to, at least a portion of a labeled probe. In certain embodiments, the oligonucleotide's addressable portion is not complementary with target sequences, primer sequences, or probe sequences other than complementary portions of labeled oligonucleotides.

The gene specific regions of oligonucleotides are of sufficient length to permit specific annealing to complementary sequences in primers, addressable portions, and targets as appropriate. In certain embodiments, the length of the addressable portions and gene specific region are any number of nucleotides from 6 to 35. Detailed descriptions of oligonucleotides design that provide for sequence-specific annealing can be found, among other places, in Diffenbach and Dveksler, PCR Primer, A Laboratory Manual, Cold Spring Harbor Press, 1995, and Kwok et al., Nucl. Acid Res. 18:999-1005 (1990).

An oligonucleotide set according to certain embodiments comprises at least one first probe region and at least one second probe region that adjacently hybridize to the same nucleic acid sample. According to certain embodiments, an oligonucleotide set is designed so that the gene specific region of the first probe region will hybridize with the downstream target region and the gene specific region of the second probe region will hybridize with the upstream target region. The gene specific regions of the oligonucleotides are of sufficient length to permit specific annealing with complementary sequences in targets and primers, as appropriate. In certain embodiments, one of the at least one first probe region and the at least one second probe region in a probe set further comprises an addressable portion.

Under appropriate conditions, adjacently hybridized oligonucleotides may be ligated together to form a ligation product, provided that they comprise appropriate reactive groups, for example, without limitation, a free 3'-hydroxyl and 5'-phosphate group.

"Diagnostic portion" and "nucleotide difference" refer to that portion of the target sequence which contains the nucleotide modification, the presence or absence of which is to be detected. "Contiguous portion" refers to a sequence of DNA which is a continuation of the nucleotide sequence of that portion of the sequence chosen as diagnostic. The continuation can be in either direction.

Oligonucleotide Preparation

In those cases where the oligonucleotides and probes are not already available, they must be synthesized. Apparatus for such synthesis is presently available commercially, such as the Applied Biosystems 380A DNA synthesizer and techniques for synthesis of various nucleic acids are available in the literature.

In one embodiment, the oligonucleotides are prepared for ligation, e.g., if ligase is to be used, the probe which will have its 5' end adjacent the 3' end of the other probe when hybridized to the sample nucleic acid is phosphorylated in order to later be able to form a phosphodiester bond between the two oligonucleotides. One of the oligonucleotides may then be labeled. This labeling can be done as part of the phosphorylation process above using radioactive phosphorus, or can be accomplished as a separate operation by covalently attaching chromophores, fluorescent moieties, enzymes, antigens, chemiluminescent moieties, groups with specific binding activity, or electrochemically detectable moieties, etc. (Appendix B provides a detailed description for 5' end labeling with $^{32}$P using $T_4$ polynucleotide kinase.)

According to certain embodiments, some oligonucleotides sets may comprise more than one first probe regions or more than one second probe regions to allow sequence discrimination between target sequences that differ by one or more nucleotides. According to certain embodiments of the invention, a oligonucleotide set is designed so that the gene specific region of the first probe region will hybridize with the downstream target region and the gene specific region of the second probe region will hybridize with the upstream target region. In certain embodiments, a nucleotide base complementary to the nucleotide difference, the "pivotal complement" or "pivotal complement nucleotide," is present on the proximal end of the second probe region of the gene specific region probe set. In certain embodiments, the first probe region may comprise the pivotal complement and addressable portion rather than the second probe region. The skilled artisan will appreciate that, in various embodiments, the nucleotide difference(s) may be located anywhere in the target sequence and that likewise, the pivotal complement(s) may be located anywhere within the gene specific region of the probe(s). For example, according to various embodiments, the pivotal complement may be located at the 3' end of a probe, at the 5' end of a probe, or anywhere between the 3' end and the 5' end of a probe. The nucleotide difference may be between the two oligonucleotides such that there is a gap when the two oligonucleotides anneal to the nucleic acid sample. As used herein, "pivotal complement," "nucleotide difference," and "nucleic acid difference" are used interchangeably.

In certain embodiments, when the first and second probe regions of the oligonucleotides are hybridized to the appropriate upstream and downstream target regions, and when the pivotal complement is at the 5' end of one probe or the 3' end of the other probe, and the pivotal complement is base-paired with the nucleotide difference on the target sequence, the hybridized first and second probe regions may be ligated together to form a ligation product.

In certain embodiments, other mechanisms may be employed to avoid ligation of oligonucleotides that do not include the correct complementary nucleotide at the pivotal complement. For example, in certain embodiments, conditions may be employed such that a probe of an oligonucleotide set will hybridize to the target sequence to a measurably lesser extent if there is a mismatch at the nucleotide difference. Thus, in such embodiments, such non-hybridized oligonucleotides will not be ligated to the other probe in the probe set. If a gap is present, they will not ligate unless the correct complement nucleotide is provided.

In certain embodiments, the first probe regions and second probe regions in an oligonucleotide set are designed with similar melting temperatures ($T_m$). Where a probe includes a pivotal complement, in certain embodiments, the $T_m$ for the probe(s) comprising the pivotal complement(s) of the target nucleotide difference sought will be approximately 4-15° C. lower than the other probe(s) that do not contain the pivotal complement in the probe set. In certain such embodiments, the probe comprising the pivotal complement(s) will also be designed with a $T_m$ near the ligation temperature. Thus, a probe with a mismatched nucleotide will more readily dissociate from the target at the ligation temperature. The ligation temperature, therefore, in certain embodiments provides another way to discriminate between, for example, multiple potential alleles in the target.

Further, in certain embodiments, oligonucleotides do not comprise a pivotal complement at the terminus of the first or the second probe region (e.g., at the 3' end or the 5' end of the first or second probe region). Rather, the pivotal complement is located somewhere between the 5' end and the 3' end of the first or second probe region. In certain such embodiments, oligonucleotides with gene specific regions that are fully complementary with their respective target regions will hybridize under high stringency conditions. Oligonucleotides with one or more mismatched bases in the gene specific region, by contrast, will hybridize to their respective target region to a measurably lesser extent. Both the first probe region and the second probe region must be hybridized to the target for a ligation product to be generated.

In certain embodiments, highly related sequences that differ by as little as a single nucleotide can be distinguished. For example, according to certain embodiments, one can distinguish the two potential alleles in a biallelic locus as follows. One can combine a oligonucleotides comprising two first probe regions, differing in their addressable portions and their pivotal complement, one second probe region, and the sample containing the target. All three oligonucleotides will hybridize with the target sequence under appropriate conditions. Only the first probe region with the hybridized pivotal complement, however, will be ligated with the hybridized second probe region. Thus, if only one allele is present in the sample, only one ligation product for that target will be generated. Both ligation products would be formed in a sample from a heterozygous individual. In certain embodiments, ligation of oligonucleotides with a pivotal complement that is not complementary to the nucleotide difference may occur, but such ligation occurs to a measurably lesser extent than ligation of oligonucleotides with a pivotal complement that is complementary to the nucleotide difference.

Many different signal moieties may be used in various embodiments of the present invention. For example, signal moieties include, but are not limited to, fluorophores, radioisotopes, chromogens, enzymes, antigens, heavy metals, dyes, phosphorescence groups, chemiluminescent groups, and electrochemical detection moieties. Exemplary fluorophores that may be used as signal moieties include, but are not limited to, rhodamine, cyanine 3 (Cy 3), cyanine 5 (Cy 5), fluorescein, Vic™, Liz™, Tamra™, 5-Fam™, 6-Fam™, and Texas Red (Molecular Probes). (Vic™, Liz™, Tamra™, 5-Fam™, and 6-Fam™ (all available from Applied Biosystems, Foster City, Calif.) Exemplary radioisotopes include, but are not limited to, $^{32}P$, $^{33}P$, and $^{35}S$. Signal moieties also include elements of multi-element indirect reporter systems, e.g., biotin/avidin, antibody/antigen, ligand/receptor, enzyme/substrate, and the like, in which the element interacts with other elements of the system in order to effect a detectable signal. Certain exemplary multi-element systems include a biotin reporter group attached to a probe and an avidin conjugated with a fluorescent label. Detailed protocols for methods of attaching signal moieties to oligonucleotides can be found in, among other places, G. T. Hermanson, Bioconjugate Techniques, Academic Press, San Diego, Calif. (1996) and S. L. Beaucage et al., Current Protocols in Nucleic Acid Chemistry, John Wiley & Sons, New York, N.Y. (2000).

Probes

As discussed above, the term "interaction probe" refers to a probe that comprises at least two moieties that can interact with one another to provide a detectably different signal value depending upon whether a given nucleic acid sequence is present or absent. In certain embodiments, one of the moieties is a signal moiety and the other moiety is a quencher moiety. The signal value that is detected from the signal moiety is different depending on whether the quencher moiety is sufficiently close to the signal moiety or is spaced apart from the signal moiety. In certain embodiments, the quencher moiety decreases the detectable signal value from the signal moiety when the quencher moiety is sufficiently close to the signal moiety. In certain embodiments, the quencher moiety decreases the detectable signal value to zero or close to zero when the quencher moiety is sufficiently close to the signal moiety.

In certain embodiments, one of the moieties of the interaction probe is a signal moiety and the other moiety is a donor moiety. The signal value that is detected from the signal moiety is different depending on whether the donor moiety is sufficiently close to the signal moiety or is spaced apart from the signal moiety. In certain embodiments, the donor moiety increases the detectable signal value from the signal moiety when the donor moiety is sufficiently close to the signal moiety. In certain embodiments, the detectable signal value is zero or close to zero when the donor moiety is not sufficiently close to the signal moiety.

In certain embodiments employing a donor moiety and signal moiety, one may use certain energy-transfer fluorescent dyes. Certain nonlimiting exemplary pairs of donors (donor moieties) and acceptors (signal moieties) are illustrated, e.g., in U.S. Pat. Nos. 5,863,727; 5,800,996; and 5,945,526. Use of certain such combinations of a donor and an acceptor have also been called FRET (Fluorescent Resonance Energy Transfer).

In certain embodiments, the moieties of the interaction probe are linked to one another by a link element such as, but not limited to, an oligonucleotide. In certain such embodiments, the presence of a sequence that hybridizes to a interaction probe impacts the proximity of the moieties to one another during the methods described herein. In various embodiments, the moieties may be attached to the link element in various ways known in the art. For example, certain nonlimiting protocols for attaching moieties to oligonucleotides are found in, among other places, G. T. Hermanson, Bioconjugate Techniques, Academic Press, San Diego, Calif. (1996) and S. L. Beaucage et al., Current Protocols in Nucleic Acid Chemistry, John Wiley & Sons, New York, N.Y. (2000). In certain embodiments, an interaction probe comprises more than one signal moiety. In certain embodiments, an interaction probe comprises more than one quencher moiety. In certain embodiments, an interaction probe comprises more than one donor moiety.

According to certain embodiments, the interaction probe may be a "5'-nuclease probe," which comprises a signal moiety linked to a quencher moiety or a donor moiety through a short oligonucleotide link element. When the 5'-nuclease probe is intact, the quencher moiety or the donor moiety influences the detectable signal from the signal moiety. According to certain embodiments, the 5'-nuclease probe binds to a specific nucleic acid sequence, and is cleaved by the 5' nuclease activity of at least one of a polymerase and another enzymatic construct when the probe is replaced by a newly polymerized strand during an amplification reaction such as PCR or some other strand displacement protocol.

When the oligonucleotide link element of the 5'-nuclease probe is cleaved, the detectable signal from the signal moiety changes when the signal moiety becomes further separated from the quencher moiety or the donor moiety. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

In certain embodiments, the 5'-nuclease probe is a 5'-nuclease fluorescent probe, in which the signal moiety is a fluorescent moiety and the quencher moiety is a fluorescence quencher moiety. When the probe is cleaved during a strand displacement protocol, the fluorescent moiety emits a detectable fluorescent signal. In certain embodiments, a 5'-nuclease fluorescent probe may emit a given level of signal when it is hybridized to a complementary sequence prior to cleavage, and the level of the signal is increased with cleavage. Certain exemplary embodiments of 5'-nuclease fluorescent probes are described, e.g., in U.S. Pat. No. 5,538,848, and exemplified by the TaqMan™ probe molecule, which is part of the TaqMan™ assay system (available from Applied Biosystems, Foster City, Calif.).

According to certain embodiments, the interaction probe may be a "hybridization dependent probe," which comprises a signal moiety linked to a quencher moiety or a donor moiety through an oligonucleotide link element. When the hybridization dependent probe is not bound to a given nucleic acid sequence, and is thus single stranded, the oligonucleotide link element can bend flexibly, and the quencher moiety or the donor moiety is sufficiently close to the signal moiety to influence the detectable signal from the signal moiety. In certain embodiments, the oligonucleotide link element of a hybridization dependent probe is designed such that when it is not hybridized to a given nucleic acid sequence, it folds back and hybridizes to itself, e.g., a molecular beacon probe. See, e.g., U.S. Pat. Nos. 5,118,801; 5,312,728; and 5,925,517. In certain embodiments, the oligonucleotide link element of a hybridization dependent probe does not hybridize to itself when it is not hybridized to the given nucleic acid sequence. Certain exemplary embodiments of hybridization dependent probes are described, e.g., in U.S. Pat. No. 5,723,591.

In certain embodiments, one employs nucleic acids in the hybridization dependent probes such that a substantial portion of the hybridization dependent probes are not cleaved by an enzyme during an amplification reaction. A "substantial portion of the hybridization dependent probes are not cleaved" refers to a portion of the total number of hybridization dependent probes that are designed to hybridize to a given nucleic sequence that is being amplified, and it does not refer to a portion of an individual probe. In certain embodiments, "a substantial portion of hybridization dependent probes that are not cleaved" means that at least 90% of the hybridization dependent probes are not cleaved. In certain embodiments, at least 95% of the hybridization dependent probes are not cleaved. In certain embodiments, one employs PNA for some or all of the nucleic acids of a hybridization dependent probe.

In certain embodiments, one employs hybridization dependent probes in which a substantial portion of the hybridization dependent probes do not hybridize to an addressable portion or a complement of the addressable portion during an extension reaction. A "substantial portion of the hybridization dependent probes do not hybridize" here refers to a portion of the total number of hybridization dependent probes that are designed to hybridize to a given nucleic sequence that is being amplified, and it does not refer to a portion of an individual probe. In certain embodiments, "a substantial portion of hybridization dependent probes that do not hybridize" means that at least 90% of the hybridization dependent probes do not hybridize. In certain embodiments, at least 95% of the hybridization dependent probes do not hybridize.

According to certain embodiments, the interaction probe may be a "cleavable RNA probe," which comprises a signal moiety linked to a quencher moiety or a donor moiety through a short RNA link element. When the cleavable RNA probe is intact, the quencher moiety or the donor moiety influences the detectable signal from the signal moiety. According to certain embodiments, the cleavable RNA probe binds to a specific DNA sequence, and is cleaved by RNase H, or an agent with similar activity.

When the RNA link element of the cleavable RNA probe is cleaved, the detectable signal from the signal moiety changes when the signal moiety becomes further separated from the quencher moiety or the donor moiety. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

In certain embodiments, if a particular nucleic acid sequence that is to be detected is present in a sample, a nucleic acid amplification procedure results in more DNA comprising the specific DNA sequence to which a cleavable RNA probe binds than if the particular nucleic acid sequence is not present in the sample. In such embodiments, one may determine the presence of the particular nucleic acid in the sample in view of the signal generated from the cleavable RNA probe during and/or after the amplification procedure. In certain embodiments, one may quantitate the amount of a particular nucleic acid in a sample in view of the signal generated from a cleavable RNA probe during and/or after the amplification procedure.

In certain embodiments, the cleavable RNA probe is a cleavable RNA fluorescent probe, in which the signal moiety is a fluorescent moiety and the quencher moiety is a fluorescence quencher moiety. When the probe is cleaved, the fluorescent moiety emits a detectable fluorescent signal. In certain embodiments, a cleavable RNA probe may emit a given level of signal when it is hybridized to a complementary sequence prior to cleavage, and the level of the signal is increased with cleavage.

According to certain embodiments, the interaction probe may be a "structure-specific nuclease probe," which comprises a signal moiety linked to a quencher moiety or a donor moiety through a short oligonucleotide link element. When the structure-specific nuclease probe is intact, the quencher moiety or the donor moiety influences the detectable signal from the signal moiety. According to certain embodiments, the structure-specific nuclease probe binds to a specific nucleic acid sequence, and is cleaved by a structure-specific nuclease if it is appropriately hybridized to the specific nucleic acid sequence.

When the oligonucleotide link element of the structure-specific nuclease probe is cleaved, the detectable signal from the signal moiety changes when the signal moiety becomes further separated from the quencher moiety or the donor moiety. In certain such embodiments that employ a quencher moiety, the signal value increases when the signal moiety becomes further separated from the quencher moiety. In certain such embodiments that employ a donor moiety, the signal value decreases when the signal moiety becomes further separated from the donor moiety.

In certain embodiments, the structure-specific nuclease probe is a structure-specific nuclease fluorescent probe, in which the signal moiety is a fluorescent moiety and the quencher moiety is a fluorescence quencher moiety. When the probe is cleaved, the fluorescent moiety emits a detectable fluorescent signal. In certain embodiments, a structure-specific nuclease probe may emit a given level of signal when it is hybridized to a complementary sequence prior to cleavage, and the level of the signal is increased with cleavage.

Other examples of suitable labeled probes according to certain embodiments are i-probes, scorpion probes, eclipse probes, and others. Exemplary, but nonlimiting, probes are discussed, for example, in Whitcombe et al., Nat. Biotechnol., 17(8): 804-807 (1999) (includes scorpion probes); Thelwell et al., Nucleic Acids Res., 28(19): 3752-3761 (2000) (includes scorpion probes); Afonina et al., Biotechniques, 32(4): (2002) (includes eclipse probes); Li et al., "A new class of homogeneous nucleic acid probes based on specific displacement hybridization," Nucleic Acids Res., 30(2):E5 (2002); Kandimall et al., Bioorg. Med. Chem., 8(8):1911-1916 (2000); Isacsson et al., Mol. Cell. Probes, 14(5):321-328 (2000); French et al, Mol. Cell. Probes, 15(6):363-374 (2001); and Nurmi et al., "A new label technology for the detection of specific polymerase chain reaction products in a closed tube," Nucleic Acids Res., 28(8), E28 (2000). Exemplary quencher moieties according to certain embodiments may be those available from Epoch Biosciences, Bothell, Wash.

In certain embodiments, one may use a labeled probe and a threshold difference between first and second detectable signal values to detect the presence or absence of a target nucleic acid in a sample. In such embodiments, if the difference between the first and second detectable signal values is the same as or greater than the threshold difference, i.e., there is a threshold difference, one concludes that the target nucleic acid is present. If the difference between the first and second detectable signal values is less than the threshold difference, i.e., there is no threshold difference, one concludes that the target nucleic acid is absent.

The skilled artisan will appreciate that while the probes and oligonucleotides of the invention may be described in the singular form, a plurality of probes or primers may be encompassed by the singular term, as will be apparent from the context. Thus, for example, in certain embodiments, oligonucleotides typically comprises a plurality of first probe regions and a plurality of second probe regions.

The criteria for designing sequence-specific oligonucleotides and probes are well known to persons of ordinary skill in the art. Detailed descriptions of primer design that provide for sequence-specific annealing can be found, among other places, in Diffenbach and Dveksler, PCR Primer, A Laboratory Manual, Cold Spring Harbor Press, 1995, and Kwok et al. (Nucl. Acid Res. 18:999-1005,1990). The gene specific regions of the oligonuleotides are of sufficient length to permit specific annealing to complementary sequences in ligation products and amplification products, as appropriate.

In embodiments that employ a promoter sequence, the promoter sequence or its complement will be of sufficient length to permit an appropriate polymerase to interact with it. Detailed descriptions of sequences that are sufficiently long for polymerase interaction can be found in, among other places, Sambrook and Russell.

According to certain embodiments, a primer set of the present invention comprises at least one second primer. In certain embodiments, the second primer in that primer set is designed to hybridize with a 3' primer region of a ligation or amplification product in a sequence-specific manner. In certain embodiments, the primer set further comprises at least one first primer. In certain embodiments, the first primer of a primer set is designed to hybridize with the complement of the 5' primer region of that same ligation or amplification product in a sequence-specific manner. In certain embodiments, at least one primer of the primer set comprises a promoter sequence or its complement or a portion of a promoter sequence or its complement. For a discussion of oligonuleotides comprising promoter sequences, see, e.g., Sambrook and Russell.

A universal primer or primer set may be employed according to certain embodiments. In certain embodiments, a universal primer or a universal primer set hybridizes with two or more of the probes, ligation products, or amplification products in a reaction, as appropriate. When universal primer sets are used in certain amplification reactions, such as, but not limited to, PCR, qualitative or quantitative results may be obtained for a broad range of template concentrations.

In certain embodiments involving a ligation reaction and an amplification reaction, one may employ at least one probe and/or at least one primer that includes a minor groove binder attached to it. Certain exemplary minor groove binders and certain exemplary methods of attaching minor groove binders to oligonucleotides are discussed, e.g., in U.S. Pat. Nos. 5,801,155 and 6,084,102. Certain exemplary minor groove binders are those available from Epoch Biosciences, Bothell, Wash. According to certain embodiments, a minor groove binder may be attached to at least one of the following: at least one probe of an oligonucleotide set; at least one primer of a primer set; and at least one labeled probe.

The skilled artisan will appreciate that the complement of the disclosed probe, target, and primer sequences, or combinations thereof, may be employed in certain embodiments of the invention. For example, without limitation, a genomic DNA sample may comprise both the target sequence and its complement. Thus, in certain embodiments, when a genomic sample is denatured, both the target sequence and its complement are present in the sample as single-stranded sequences. In certain embodiments, ligation probes may be designed to specifically hybridize to an appropriate sequence, either the target sequence or its complement.

Ligation

Certain embodiments include a ligation agent. For example, ligase is an enzymatic ligation agent that, under appropriate conditions, forms phosphodiester bonds between the 3'-OH and the 5'-phosphate of adjacent nucleotides in DNA or RNA molecules, or hybrids. Exemplary ligases include, but are not limited to, Tth K294R ligase and Tsp AK16D ligase. See, e.g., Luo et al., Nucleic Acids Res., 24(14):3071-3078 (1996); Tong et al., Nucleic Acids Res., 27(3):788-794 (1999); and Published PCT Application No. WO 00/26381. Temperature sensitive ligases, include, but are not limited to, T4 DNA ligase, T7 DNA ligase, and *E. coli* ligase. In certain embodiments, thermostable ligases include, but are not limited to, Taq ligase, Tth ligase, Tsc ligase, and Pfu ligase. Certain thermostable ligases may be obtained from thermophilic or hyperthermophilic organisms, including but not limited to, prokaryotic, eucaryotic, or archael organisms. Certain RNA ligases may be employed in certain embodiments. In certain embodiments, the ligase is a RNA dependent DNA ligase, which may be employed with RNA template and DNA ligation probes. An exemplary, but non-limiting example, of a ligase with such RNA dependent DNA ligase activity is T4 DNA ligase. In certain embodiments, the ligation agent is an "activating" or reducing agent.

Chemical ligation agents include, without limitation, activating, condensing, and reducing agents, such as carbodiimide, cyanogen bromide (BrCN), N-cyanoimidazole, imidazole, 1-methylimidazole/carbodiimide/cysta-mine, dithiothreitol (DTT) and ultraviolet light. Autoligation, i.e., spontaneous ligation in the absence of a ligating agent, is also within the scope of certain embodiments of the invention. Detailed protocols for chemical ligation methods and descriptions of appropriate reactive groups can be found, among other places, in Xu et al., Nucleic Acid Res., 27:875-81 (1999); Gryaznov and Letsinger, Nucleic Acid Res. 21:1403-08 (1993); Gryaznov et al., Nucleic Acid Res. 22:2366-69 (1994); Kanaya and Yanagawa, Biochemistry 25:7423-30 (1986); Luebke and Dervan, Nucleic Acids Res. 20:3005-09 (1992); Sievers and von Kiedrowski, Nature 369:221-24 (1994); Liu and Taylor, Nucleic Acids Res. 26:3300-04 (1999); Wang and Kool, Nucleic Acids Res. 22:2326-33 (1994); Purmal et al., Nucleic Acids Res. 20:3713-19 (1992); Ashley and Kushlan, Biochemistry 30:2927-33 (1991); Chu and Orgel, Nucleic Acids Res. 16:3671-91 (1988); Sokolova et al., FEBS Letters 232:153-55 (1988); Naylor and Gilham, Biochemistry 5:2722-28 (1966); and U.S. Pat. No. 5,476,930.

In certain embodiments, at least one polymerase is included. In certain embodiments, at least one thermostable polymerase is included. Exemplary thermostable polymerases, include, but are not limited to, Taq polymerase, Pfx polymerase, Pfu polymerase, Vent™ polymerase, Deep Vent™ polymerase, Pwo polymerase, Tth polymerase, UlTma polymerase and enzymatically active mutants and variants thereof (see The Scientist 12(1):17 (Jan. 5, 1998); and at the article The Scientist 15(17):1 (Sep. 3, 2001)).

Ligation according to the present invention comprises any enzymatic or chemical process wherein an internucleotide linkage is formed between the opposing ends of nucleic acid sequences that are adjacently hybridized to a template. Additionally, the opposing ends of the annealed nucleic acid sequences should be suitable for ligation (suitability for ligation is a function of the ligation method employed). The internucleotide linkage may include, but is not limited to, phosphodiester bond formation. Such bond formation may include, without limitation, those created enzymatically by a DNA or RNA ligase, such as bacteriophage T4 DNA ligase, T4 RNA ligase, T7 DNA ligase, *Thermus thermophilus* (Tth) ligase, *Thermus aquaticus* (Taq) ligase, or *Pyrococcus furiosus* (Pfu) ligase. Other internucleotide linkages include, without limitation, covalent bond formation between appropriate reactive groups such as between an .alpha.-haloacyl group and a phosphothioate group to form a thiophosphorylacetylamino group; and between a phosphorothioate and a tosylate or iodide group to form a 5'-phosphorothioester or pyrophosphate linkages.

In certain embodiments, chemical ligation may, under appropriate conditions, occur spontaneously such as by autoligation. Alternatively, in certain embodiments, "activating" or reducing agents may be used. Examples of activating agents and reducing agents include, without limitation, carbodiimide, cyanogen bromide (BrCN), imidazole, 1-methylimidazole/carbodiimide/cystamine, N-cyanoimidazole, dithiothreitol (DTT) and ultraviolet light. Nonenzymatic ligation according to certain embodiments may utilize specific reactive groups on the respective 3' and 5' ends of the aligned probes.

In certain embodiments, ligation generally comprises at least one cycle of ligation, for example, the sequential procedures of: hybridizing the gene specific regions of a first probe region and a second probe region, that are suitable for ligation, to their respective complementary regions on a nucleic acid sample; ligating the 3' end of the first probe region with the 5' end of the second probe region to form a ligation product; and denaturing the nucleic acid duplex to separate the ligation product from the nucleic acid sample. The cycle may or may not be repeated. For example, without limitation, by thermocycling the ligation reaction to linearly increase the amount of ligation product.

According to certain embodiments, one may use ligation techniques such as gap-filling ligation, including, without limitation, gap-filling OLA and LCR, bridging oligonucleotide ligation, FEN-LCR, and correction ligation. Descriptions of these techniques can be found, among other places, in U.S. Pat. No. 5,185,243, published European Patent Applications EP 320308 and EP 439182, published PCT Patent Application WO 90/01069, published PCT Patent Application WO 02/02823, and U.S. patent application Ser. No. 09/898,323.

In certain embodiments, one may employ poly dIC in a ligation reaction. In certain embodiments, one uses any number between 15 to 80 ng/microliter of poly dIC in a ligation reaction. In certain embodiments, one uses 30 ng/microliter of poly dIC in a ligation reaction.

One may use poly dIC in a ligation reaction with various methods employing ligation probes with addressable portions as discussed herein. In certain embodiments, one may use poly dIC with different types of ligation methods. For example, one may use poly dIC in any of a variety of methods employing ligation reactions. Exemplary methods include, but are not limited to, those discussed in U.S. Pat. No. 6,027,889, PCT Published Patent Application No. WO 01/92579, and U.S. patent application Ser. Nos. 09/584,905 and 10/011,993.

In certain embodiments, one forms a test composition for a subsequent amplification reaction by subjecting a ligation reaction composition to at least one cycle of ligation. In certain embodiments, after ligation, the test composition may be used directly in the subsequent amplification reaction. In certain embodiments, prior to the amplification reaction, the test composition may be subjected to a purification technique that results in a test composition that includes less than all of the components that may have been present after the at least one cycle of ligation. For example, in certain embodiments, one may purify the ligation product.

Purifying the ligation product according to certain embodiments comprises any process that removes at least some unligated probes, nucleic acid samples, enzymes, and/or accessory agents from the ligation reaction composition following at least one cycle of ligation. Such processes include, but are not limited to, molecular weight/size exclusion processes, e.g., gel filtration chromatography or dialysis, sequence-specific hybridization-based pullout methods, affinity capture techniques, precipitation, adsorption, or other nucleic acid purification techniques. The skilled artisan will appreciate that purifying the ligation product prior to amplification in certain embodiments reduces the quantity of primers needed to amplify the ligation product, thus reducing the cost of detecting a target sequence. Also, in certain embodiments, purifying the ligation product prior to amplification may decrease possible side reactions during amplification and may reduce competition from unligated probes during hybridization.

Hybridization-based pullout (HBP) according to certain embodiments of the present invention comprises a process wherein a nucleotide sequence complementary to at least a portion of one probe or oligonucleotide (or their complements), for example, the primer region, is bound or immobilized to a solid or particulate pullout support (see, e.g., U.S. Pat. No. 6,124,092). In certain embodiments, a composition comprising ligation product, target sequences, and unligated probes is exposed to the pullout support. The ligation product, under appropriate conditions, hybridizes with the support-bound sequences. The unbound components of the composition are removed, purifying the ligation products from those ligation reaction composition components that do not contain sequences complementary to the sequence on the pullout support. One subsequently removes the purified ligation products from the support and combines them with at least one primer set to form a first amplification reaction composition. The skilled artisan will appreciate that, in certain embodiments, additional cycles of HBP using different complementary sequences on the pullout support may remove all or substantially all of the unligated probes, further purifying the ligation product.

Amplification according to the present invention encompasses a broad range of techniques for amplifying nucleic acid sequences, either linearly or exponentially. Exemplary amplification techniques include, but are not limited to, PCR or any other method employing a primer extension step, and transcription or any other method of generating at least one RNA transcription product. Other nonlimiting examples of amplification are ligase detection reaction (LDR), and ligase chain reaction (LCR). Amplification methods may comprise thermal-cycling or may be performed isothermally. The term "amplification product" includes products from any number of cycles of amplification reactions, primer extension reactions, and RNA transcription reactions, unless otherwise apparent from the context.

In certain embodiments, amplification methods comprise at least one cycle of amplification, for example, but not limited to, the sequential procedures of: hybridizing primers to primer regions of the ligation product or amplification products from any number of cycles of an amplification reaction; synthesizing a strand of nucleotides in a template-dependent manner using a polymerase; and denaturing the newly-formed nucleic acid duplex to separate the strands. The cycle may or may not be repeated. In certain embodiments, amplification methods comprise at least one cycle of amplification, for example, but not limited to, the sequential procedures of: interaction of a polymerase with a promoter; synthesizing a strand of nucleotides in a template-dependent manner using a polymerase; and denaturing the newly-formed nucleic acid duplex to separate the strands. The cycle may or may not be repeated.

Descriptions of certain amplification techniques can be found, among other places, in H. Ehrlich et al., Science, 252:1643-50 (1991), M. Innis et al., PCR Protocols: A Guide to Methods and Applications, Academic Press, New York, N.Y. (1990), R. Favis et al., Nature Biotechnology 18:561-64 (2000), and H. F. Rabenau et al., Infection 28:97-102 (2000); Sambrook and Russell, Ausbel et al.

Primer extension according to the present invention is an amplification process comprising elongating a primer that is annealed to a template in the 5' to 3' direction using a template-dependent polymerase. According to certain embodiments, with appropriate buffers, salts, pH, temperature, and nucleotide triphosphates, including analogs and derivatives thereof, a template dependent polymerase incorporates nucleotides complementary to the template strand starting at the 3'-end of an annealed primer, to generate a complementary strand. Detailed descriptions of primer extension according to certain embodiments can be found, among other places in Sambrook et al., Sambrook and Russell, and Ausbel et al.

Transcription according to certain embodiments is an amplification process comprising an RNA polymerase interacting with a promoter on a single- or double-stranded template and generating a RNA polymer in a 5' to 3' direction. In certain embodiments, the transcription reaction composition further comprises transcription factors. RNA polymerases, including but not limited to T3, T7, and SP6 polymerases, according to certain embodiments, can interact with double-stranded promoters. Detailed descriptions of transcription according to certain embodiments can be found, among other places in Sambrook et al., Sambrook and Russell, and Ausbel et al.

Certain embodiments of amplification may employ multiplex PCR, in which multiple target sequences are simultaneously amplified (see, e.g., H. Geada et al., Forensic Sci. Int. 108:31-37 (2000) and D. G. Wang et al., Science 280:1077-82 (1998)).

In certain embodiments, one employs asymmetric PCR. In certain embodiments, one may use at least one primer set wherein the melting temperature ($T_m50$) of one of the primers is higher than the $T_m50$ of the other primer. Such embodiments have been called asynchronous PCR (A-PCR). See, e.g., U.S. patent application Ser. No. 09/875,211, filed Jun. 5, 2001. In certain embodiments of A-PCR, in addition to the difference in $T_m50$ of the primers in a primer set, there is also an excess of one primer relative to the other primer in the primer set. In certain embodiments, there is a five to twenty-fold excess of one primer relative to the other primer in the primer set. In certain embodiments of A-PCR, the primer concentration is at least 50 mM.

Methods of optimizing amplification reactions are well known to those skilled in the art. For example, it is well known that PCR may be optimized by altering times and temperatures for annealing, polymerization, and denaturing, as well as changing the buffers, salts, and other reagents in the reaction composition. Optimization may also be affected by the design of the amplification primers used. For example, the length of the primers, as well as the G-C:A-T ratio may alter the efficiency of primer annealing, thus altering the amplification reaction. See James G. Wetmur, "Nucleic Acid Hybrids, Formation and Structure," in Molecular Biology and Biotechnology, pp. 605-8, (Robert A. Meyers ed., 1995).

In certain amplification reactions, one may use dUTP and uracil-N-glucosidase (UNG). Discussion of use of dUTP and UNG may be found, for example, in Kwok et al., "Avoiding false positives with PCR," Nature, 339:237-238 (1989); and Longo et al. "Use of uracil DNA glycosylase to control carryover contamination in polymerase chain reactions," Gene, 93:125-128 (1990).

To detect whether a particular sequence is present, in certain embodiments, a labeled probe is included in the amplification reaction. According to certain embodiments, the labeled probe indicates the presence or absence (or amount) of a specific nucleic acid sequence in the reaction. These include, but are not limited to, 5'-nuclease probes, cleavage RNA probes, structure-specific nuclease probes, and hybridization dependent probes. In certain embodiments, the labeled probe comprises a fluorescing dye connected to a quenching molecule through a link element, e.g., through a specific oligonucleotide. Examples of such systems are described, e.g., in U.S. Pat. Nos. 5,538,848 and 5,723,591.

Other examples of suitable labeled probes according to certain embodiments are i-probes, scorpion probes, eclipse probes, and others. Exemplary, but nonlimiting, probes are discussed, for example, in Whitcombe et al., Nat. Biotechnol., 17(8):804-807 (1999) (includes scorpion probes); Thelwell et al., Nucleic Acids Res., 28(19):3752-3761 (2000) (includes scorpion probes); Afonina et al., Biotechniques, 32(4): (2002) (includes eclipse probes); Li et al., "A new class of homogeneous nucleic acid probes based on specific displacement hybridization," Nucleic Acids Res., 30(2):E5 (2002); Kandimall et al., Bioorg. Med. Chem., 8(8):1911-1916 (2000); Isacsson et al., Mol. Cell. Probes, 14(5):321-328 (2000); French et al, Mol. Cell. Probes, 15(6):363-374 (2001); and Nurmi et al., "A new label technology for the detection of specific polymerase chain reaction products in a closed tube," Nucleic Acids Res., 28(8), E28 (2000).

In certain embodiments, the amount of labeled probe that gives a fluorescent signal in response to an emitted light typically relates to the amount of nucleic acid produced in the amplification reaction. Thus, in certain embodiments, the amount of fluorescent signal is related to the amount of product created in the amplification reaction. In such embodiments, one can therefore measure the amount of amplification product by measuring the intensity of the fluorescent signal from the fluorescent indicator. According to certain embodiments, one can employ an internal standard to quantify the amplification product indicated by the fluorescent signal. See, e.g., U.S. Pat. No. 5,736,333.

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism™ 7700 Sequence Detection System (Applied Biosystems, Foster City, Calif.) and the ABI GeneAmp™ 5700 Sequence Detection System (Applied Biosystems, Foster City, Calif.).

In certain embodiments, each of these functions may be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In certain embodiments, combined thermal cycling and fluorescence detecting devices can be used for precise quantification of nucleic acid samples in samples. In certain embodiments, fluorescent signals can be detected and displayed during and/or after one or more thermal cycles, thus permitting monitoring of amplification products as the reactions occur in "real time." In certain embodiments, one can use the amount of amplification product and number of amplification cycles to calculate how much of the nucleic acid sample was in the sample prior to amplification.

According to certain embodiments, one could simply monitor the amount of amplification product after a predetermined number of cycles sufficient to indicate the presence of the nucleic acid sample in the sample. One skilled in the art can easily determine, for any given sample type, primer sequence, and reaction condition, how many cycles are sufficient to determine the presence of a given target polynucleotide.

According to certain embodiments, the amplification products can be scored as positive or negative as soon as a given number of cycles is complete. In certain embodiments, the results may be transmitted electronically directly to a database and tabulated. Thus, in certain embodiments, large numbers of samples may be processed and analyzed with less time and labor required.

According to certain embodiments, different labeled probes may distinguish between different nucleic acid samples. A non-limiting example of such a probe is a 5'-nuclease fluorescent probe, such as a TaqMan™ probe molecule, wherein a fluorescent molecule is attached to a fluorescence-quenching molecule through an oligonucleotide link element. In certain embodiments, the oligonucleotide link element of the 5'-nuclease fluorescent probe binds to a specific sequence of an addressable portion or its complement. In certain embodiments, different 5'-nuclease fluorescent probes, each fluorescing at different wavelengths, can distinguish between different amplification products within the same amplification reaction.

The present invention is directed to methods, reagents, and kits for detecting the presence or absence of (or quantitating) nucleic acid samples in a biological sample, using ligation and amplification reactions. When a particular nucleic acid sample is present in a sample, a ligation product is formed that includes an addressable portion. Labeled probes are employed that provide a different detectable signal value depending upon whether a complementary sequence is present or absent during an amplification reaction. In certain embodiments, the labeled probes are designed to comprise a sequence that is the same as the sequence of the addressable portion or that is complementary to the sequence of the addressable portion.

In certain embodiments, one or more nucleic acid species are subjected to ligation and amplification reactions, either directly or via an intermediate, such as a cDNA target generated from an mRNA by reverse transcription. In certain embodiments, the initial nucleic acid comprises mRNA and a reverse transcription reaction may be performed to generate at least one cDNA, followed by at least one ligation reaction and at least one amplification reaction. In certain embodiments, DNA ligation probes hybridize to target RNA, and an RNA dependent DNA ligase is employed in a ligation reaction, followed by an amplification reaction. The ligation products and amplification products may be detected (or quantitated) using labeled probes.

In certain embodiments, if no nucleic acid sample had been present in the sample, no ligation product comprising the addressable portion and the 5' and 3' primer regions would have been formed during the ligation reaction. Accordingly, no labeled probe would bind to a ligation product or an amplification product and there would be no cleavage of a labeled probe during the amplification reaction. (Some of the labeled probes may hybridize to unligated ligation probes.) Thus, the absence of a detectable signal during or after the amplification reaction would indicate the absence of nucleic acid sample in the sample. In certain embodiments, ligation products may form even if the appropriate nucleic acid sample is not in the sample, but such ligation occurs to a measurably lesser extent than when the appropriate nucleic acid sample is in the sample. In certain such embodiments, one can set an appropriate threshold difference between detectable signal values to differentiate between samples that include the appropriate nucleic acid sample and samples that do not include the appropriate nucleic acid sample.

In certain embodiments, if no nucleic acid sample had been present in the sample, no ligation product comprising the addressable portion and the 5' and 3' primer regions would have been formed during the ligation reaction. Thus, no amplification product comprising the complement of the addressable portion of such a ligation product would be formed. Accordingly, no labeled probe would bind to a ligation product or an amplification product and there would be no cleavage of a labeled probe during the amplification reaction. Thus, the absence of a detectable signal during or after the amplification reaction would indicate the absence of nucleic acid sample in the sample. In certain embodiments, ligation products may form even if the appropriate nucleic acid sample is not in the sample, but such ligation occurs to a measurably lesser extent than when the appropriate nucleic acid sample is in the sample. In certain such embodiments, one can set an appropriate threshold difference between detectable signal values to differentiate between samples that include the appropriate nucleic acid sample and samples that do not include the appropriate nucleic acid sample.

In certain embodiments, if no nucleic acid sample had been present in the sample, no ligation product comprising the addressable portion and the 5' and 3' primer regions would have been formed during the ligation reaction. Thus, no amplification product comprising the complement of such a ligation product would be formed. Accordingly, no labeled probe would bind to a ligation product or an amplification product and there would be no cleavage of a labeled probe during the amplification reaction. Thus, the absence of a detectable signal during or after the amplification reaction would indicate the absence of nucleic acid sample in the sample. In certain embodiments, ligation products may form even if the appropriate nucleic acid sample is not in the sample, but such ligation occurs to a measurably lesser extent than when the appropriate nucleic acid sample is in the sample. In certain such embodiments, one can set an appropriate threshold difference between detectable signal values to differentiate between samples that include the appropriate nucleic acid sample and samples that do not include the appropriate nucleic acid sample.

Primers

According to certain embodiments, as few as one universal primer or one universal primer set can be used to amplify one or more ligation or amplification products, since the probes may be designed to share primer regions but comprise different addressable portions and/or gene specific regions.

The methods of the instant invention according to certain embodiments may comprise universal primers or universal primer sets that decrease the number of different primers that are added to the reaction composition, reducing the cost and time required. For example, without limitation, in a 100-target-sequence multiplex reaction, typically 100 different primer sets are required using certain conventional methods. According to certain embodiments of the present invention, anywhere from 100 primer sets to as few as one primer set may be employed in the same 100 target multiplex. For example, in certain embodiments, all of the ligation or amplification products to be amplified by a universal primer or universal primer set comprise the same 5' primer region and the same 3' primer region. The skilled artisan will appreciate that, in certain embodiments, more than one universal primer set may be employed in a multiplex reaction, each specific to a different subset of ligation or amplification products in the reaction. In certain embodiments, the amplification reaction composition may comprise at least one universal primer or universal primer set and at least one primer or primer set that hybridizes to only one species of probe, ligation product, or amplification product.

In certain embodiments, because only one or a limited number of primers or primer sets are used for amplification, the methods are more cost-efficient and less time-consuming than conventional methods of detecting or quantitating nucleic acid samples in a sample. In certain embodiments, using a limited number of primers may also reduce variation in amplification efficiency and cross-reactivity of the primers. Additionally, in certain embodiments, quantitative results may be obtained from multiplex reactions for those ligation products or amplification products that are amplified by a universal primer or universal primer set, respectively.

The skilled artisan will appreciate that in certain embodiments, including, but not limited to, detecting multiple alleles, the ligation reaction composition may comprise more than one first probe region or more than one second probe region for each potential allele in a multiallelic target locus. In certain embodiments, those methods employ different probes with different addressable portions for each different allele at each locus. In certain such embodiments, the amplification reaction composition may include a different labeled probe for each different addressable portion. In certain embodiments, each different labeled probe may have a detectably different signal for each different addressable portion.

Many alleles of a large number of genes have been sequenced for research purposes and these sequences are stored in the EMBL databank (for Europe) and in Genbank (USA). On the basis of these sequences, many sequences can be examined for potential single-nucleotide polymorphisms and thereby used to identify different alleles that are susceptible to examination using the methods disclosed herein. Most genes and systems of genes contain regions of sequences which are subject to different degrees of sequence variability (i.e., mutation, polymorphism). Depending on the gene system, such variability may have been extensively studied and is available for further analysis by the methods described herein. Thus, the presence of usable sequences for the methods according to the present invention can be detected by more detailed analysis of Genbank and EMBL submissions, supplemented by self-determined sequences.

By way of example, chromosomal DNA of a subject being tested or screened is obtained from a biological sample. As discussed herein, biological samples can be obtained from a variety of tissues depending on the age and condition of the subject. For example, biological samples may be obtained from peripheral blood using well known techniques. In fetal testing, a sample is preferably obtained by amniocentesis or chorionic villi sampling. Other sources of DNA include semen, buccal cells, and cells found in the feces. Preferably, DNA is extracted from the sample using standard procedures, e.g., phenol:chloroform extraction as described by Maniatis et al., referred to above, and Higuchi (May 1989) PCR Applications, Issue 2 (Perkin Elmer-Cetus Users Bulletin). Biological samples for fetal testing can also be obtained from maternal peripheral blood using fluorescence-activated cell sorting, as described, e.g., by Iverson et al. (1981) Prenatal Diagnosis, 9:31-48.

Diseases readily diagnosed by the methods of the present invention include, but are in no way limited to, Parlinson's disease, Duchenne muscular dystrophy, Niemann-Pick disease, polyposis, neurofibromatosis, polycystic kidney disease, Tay-Sachs disease, xeroderma pigmentosa, ataxia-telangiectasia, Huntington disease, Li-Fraumeni syndrome, beta-thalassemia, sickle cell anemia, hemoglobin C disease, hemophilia, acute intermittent porphyria, cystic fibrosis, diabetes, obesity and cancer, as well as other types of cancer wherein a genetic mutation is involved. Such cancers include, but are in no way limited to, cancers selected from the group consisting of leukemia, lymphoma, melanoma, neuroblastoma, retinoblastoma, rhabdomyosarcoma, Ewing sarcoma, head and neck cancer, skin cancer, brain cancer, esophageal cancer, stomach cancer, lung cancer, breast cancer, colon cancer, ovarian cancer, testicular cancer and prostate cancer.

Methods used to amplify either the ligation product or the nucleic acid sample include methods discussed infra and, for example, rolling circle amplification discussed in U.S. Pat. Nos. 5,198,543 and 5,001,050), phage M2 DNA polymerase (Matsumoto et al., Gene 84:247 (1989)), phage .phi.-PRD1 DNA polymerase (Jung et al., Proc. Natl. Acad. Sci. USA 84:8287 (1987)), VENT™. DNA polymerase (Kong et al., J. Biol. Chem. 268:1965-1975 (1993)), Klenow fragment of DNA polymerase I (Jacobsen et al., Eur. J. Biochem. 45:623-627 (1974)), T5 DNA polymerase (Chatterjee et al., Gene 97:13-19 (1991)), PRD1 DNA polymerase (Zhu and Ito, Biochim. Biophys. Acta. 1219(2):267-276 (1994)), T4 DNA polymerase, *E. coli* DNA polymerase III holoenzyme (Kaboord and Benkovic, Curr. Biol. 5:149-157 (1995)), and T7 DNA polymerase, with .pbi.29 and T7 DNA polymerase being especially preferred. Strand displacement can be facilitated through the use of a strand displacement factor, such as a helicase enzyme. The ability of a polymerase to carry out rolling circle replication can be determined by using the polymerase in a rolling circle replication assay such as those described in Fire and Xu, Proc. Natl. Acad. Sci. USA 92:4641-4645 (1995) and in the examples provided in Lizardi, U.S. Pat. No. 5,854,033, especially Example 1 thereof.

In another embodiment of the invention, the identity of multiple polymorphic sites in a DNA sample can be determined using multiple primers. Multiple polymorphic sites may serve as markers for a genetic disorder or phenotype, and subtypes of the disorder or phenotype may be distinguishable by determining the nucleotide occurring at each of a plurality of known polymorphic sites. Alternatively, the presence of a particular combination of variants in several SNPs may indicate that an individual is suffering from a particular disease or has a predisposition for a particular disease. In addition, a sample from an individual may be analyzed to determine whether the individual is at risk of developing a plurality of diseases or phenotypes, or currently possesses a plurality of diseases or phenotypes. Thus, the identities of the polymorphic bases of a SNP or combination of SNPs, each of which is associated with a different disease or phenotype, are determined in the sample. In one version of this embodiment, the primer for each site has a distinct length, such that the primer and any extension products can be distinguished from other primers annealing to other sites and their extension products.

Methods described herein use, for example, a modification of Oligonucleotide Ligation Assay (OLA) to convert DNA molecules with only single base changes to those which contain a completely unique stretch of DNA (about 20 bases for use as probe detection). In the second part of the assay, real-time quantitative PCR (Q-PCR) is performed using universal primers to sensitively and quantitatively detect the probe containing DNA (and therefore the single base change). Because the strategy involves a ligation step, followed by a Q-PCR amplification step, designated as "LigAmp".

A method to increase the specificity of a methods of the invention is also provided. It is possible to prevent the ligation of the "variant," "mutant" or "nucleic acid different" specific oligonucleotides on the wild-type target, by providing to the reaction an oligonucleotide that straddles the ligation site of the wild-type allele. This oligonucleotide could be composed of DNA, RNA, locked nucleic acid, or peptide nucleic acid, and referred to herein as a "blocking probe." The blocking probe may be from 5-50 nucleotides in length.

Pooled Samples

The methods herein are capable of identifying, for example, uncommon samples. An example of an uncommon sample is a rare blood type. The power of the method is exemplified by the following: 100 blood donor samples are provided and pooled into 10 pools. Ten assays according to the invention are performed to determine which pool contains a rare blood type. Having identified the correct pool, an assay is performed on each of these individual samples to determine the sample containing the rare blood type. This pooling method only requires a total of 20 assays, rather than 100 if each sample were tested individually. Many variations on the pooling method are envisioned. For example, to increase the speed of the assay the samples could be pooled in a 10×10 matrix. The rows and columns are then pooled generating samples R1 to R10 and C1 to C10, respectively. These 20 pools are then tested and the pattern would indicate which sample contains the rare blood type (e.g. R6 and C8 positive).

A rare blood type among 10,000 samples could be readily identified using only 40 assays in the following way. First produce pools of 10 samples, then from these produce pools of 100 samples and from these produce pools of 1000 samples. Test the 10 pools of 1,000 samples to determine which is positive; then test the 10 pools of 100 samples comprising the pool of 1000. Having identified the pool of 100 that is positive, test the 10 pools of 10 comprising that positive pool of 100. And, having identified the positive pool of 10 samples, test each one individually.

Pancreatic Cancer And Chronic Pancreatitis

Pancreatic cancer has a poor prognosis with an overall 5 year-survival of less than 5%, accounting for the fourth largest number of cancer deaths in the United States (Jemal, 2005). This dismal outcome is largely because the majority of cancers are diagnosed at an unoperable advanced stage. Only 10-20% of patients are candidates for surgery at the time of presentation. Patients who are surgical candidates (without clinically evident metastases) and undergo resection with non-metastatic lesions have a better outcome with a 5-year survival of 15-20% (Jemal, 2005). Therefore, early detection will likely be an essential element for improved survival of this otherwise deadly disease. Unfortunately, the early diagnosis of pancreatic cancer is fraught with difficulty. The clinical presentation of pancreatic cancer resembles that of chronic pancreatitis. In addition, current imaging studies including computed tomography, magnetic resonance imaging and positron emission tomography are not sensitive and/or specific enough to distinguish an inflammatory mass from a cancer lesion (Saisho, 2004 #10). Even endoscopic ultrasonography-guided needle aspiration or brushings during endoscopic retrograde cholangiopancreatography sometimes have difficulties discriminating pancreatic cancer from chronic pancreatitis (Mitchell, 1985). Accurate and sensitive techniques are urgently needed to detect pancreatic cancer at an early stage. The need for early detection is especially critical for patients at very high risk such as those with remarkable family histories or chronic panreatitis.

Development of pancreatic cancer involves multiple genetic alterations including mutational activations of oncogenes and loss of tumor suppressor genes. Point mutations of KRAS2 gene at codon 12 have been identified in most pancreatic cancers (Almoguera, 1988; Hruban, 1993; and Hruban, 2000) and can be detected in pancreatic duct juice (Yamada, 1998), as well as plasma (Castells, 1999 and Maire, 2002) and stool (Mulcahy, 1999 and Caldas, 1994). Detection of KRAS2 point mutations from pancreatic duct juice or other body fluids could provide a diagnostic tool for early cancer detection. However, KRAS2 mutations can also be detected in pancreatic duct juice from patients with chronic pancreatitis or pancreatic intraepithelial neoplasias (PanINs), pancreatic cancer precursor lesions (Maire, 2002; Hruban, 2000; van Laethem, 1999; and Queneau, 2001). While qualitative detection of mutant KRAS2 alone is not an accurate predictor of pancreatic cancer, quantitative assays for KRAS2 mutations in biological fluids might be able to distinguish between pancreatic cancer and other conditions.

HIV

Short antiretroviral drug regimens can reduce the risk of HIV-1 mother-to-child transmission (MTCT) in resource-limited settings. In the HIVNET 012 regimen, women receive a single dose (SD) of nevirapine (NVP) in labor and infants receive a SD of NVP shortly after birth. This regimen is simple, safe, inexpensive, and effective for prevention of MTCT (pMTCT) (Guay L A, Musoke P, Fleming T, et al. Lancet 1999; 354:795-802 and Jackson J B, Musoke P, Fleming T, et al. Lancet 2003; 362:859-868). A disadvantage of this regimen is the emergence of NVP resistance (NVPR) after NVP administration. In HIVNET 012, NVPR was detected in 25% of women and 46% of infants 6-8 weeks after delivery (Eshleman S H, Guay L A, Mwatha A, et al. J Acquir Immune Defic Syndr 2004; 35:126-130 and Eshleman S H, Mracna M, Guay L A, et al. AIDS 2001; 15:1951-1957). A recent study suggests that women with prior exposure to SD NVP may have a reduced virologic response to non-nucleoside reverse transcriptase (RT) inhibitor (NNRTI)-containing treatment regimens (Jourdain G, Ngo-Giang-Huong N, Le Coeur S, et al. Intrapartum exposure to nevirapine and subsequent maternal responses to nevirapine-based antiretroviral therapy. N Engl J Med 2004; 351:229-40). It is not known whether prior exposure to SD NVP reduces the efficacy of NVP-containing treatment regimens in HIV-1 infected children, or the efficacy of SD NVP for pMTCT in subsequent pregnancies. NVP-resistant variants selected in women by SD NVP could also potentially be transmitted to infants by breast-feeding, or to others in the community.

Few studies have evaluated persistence of NVPR after SD NVP. In HIVNET 012, samples collected 12-24 months after SD NVP were available for 11 women and 6 infants who had NVPR at 6-8 weeks. No NVPR mutations were detected in those samples. In the HIVNET 023 trial, variants with NVPR mutations faded from detection in almost all women by 6 months postpartum. However, in a South African cohort, 55/155 (35%) of women who had NVPR at 7 weeks still had detectable NVPR at 6 months post-partum (Morris L, Martinson N, Pillay C, et al. Persistence of nevirapine resistance mutations 6 months following single dose nevirapine. In: XV International AIDS Conference. Bangkok, Thailand, 2004). Those studies were performed with population sequencing-based genotyping assays that are relatively insensitive for detection of drug-resistant HIV-1 variants present as mixtures.

Certain Exemplary Kits

In certain embodiments, the invention also provides kits designed to expedite performing certain methods. In certain embodiments, kits serve to expedite the performance of the methods of interest by assembling two or more components used in carrying out the methods. In certain embodiments, kits may contain components in pre-measured unit amounts to minimize the need for measurements by end-users. In certain embodiments, kits may include instructions for performing one or more methods of the invention. In certain embodiments, the kit components are optimized to operate in conjunction with one another.

In certain embodiments, a kit for detecting at least one nucleic acid sample in a sample is provided. In certain embodiments, a kit comprises: a oligonucleotides for each target sequence, the probe set comprising (a) at least one first probe region, comprising a gene specific region and a 5' primer region, wherein the 5' primer region comprises a sequence, and (b) at least one second probe region, comprising a gene specific region and a 3' primer region, wherein the 3' primer region comprises a sequence. The probes in each set are suitable for ligation together when hybridized adjacent to one another on a complementary target sequence. One probe in each probe set further comprises an addressable portion located between the primer region and the gene specific region, wherein the addressable portion comprises a sequence. In certain embodiments, the kit further comprises a labeled probe comprising the sequence of the addressable portion or comprising a sequence complementary to the sequence of the addressable portion.

In certain embodiments, a kit comprises at least one oligonucleotide pair, wherein a pair comprises a first (P1) and a second (P2) oligonucleotide, wherein P1 and P2 bind to a nucleic acid to form a reaction mixture, and wherein P1 comprises a first gene specific region and a first primer binding region and P2 comprises a probe binding region, a second primer binding region and a second gene specific region, wherein there a nucleotide gap between the first and second gene specific regions contains the nucleic acid difference, and instructions for use.

In certain embodiments, kits comprise one or more additional components, including, without limitation, at least one of: at least one polymerase, at least one transcriptase, at least one ligation agent, oligonucleotide triphosphates, nucleotide analogs, reaction buffers, salts, ions, and stabilizers. In certain embodiments, kits comprise one or more reagents for purifying the ligation products, including, without limitation, at least one of dialysis membranes, chromatographic compounds, supports, and oligonucleotides.

Kits could be produced, for example, for the early detection of cancers (if cancers are detected early, patients can undergo definitive curative surgery), cancer minimal residual disease testing (e.g. Determining the whether the cancer has been eliminated or is still present, following surgery or chemotherapy, etc. Such kits could also be used to identify if a cancer is coming back (so called "molecular relapse"); infectious disease minority variant detection: viral (e.g. HIV, HBV, HCV, etc) minority variant detection (conferring anti-viral drug resistance) and other anti-microbial resistance testing where point mutations are the basis of the resistance (e.g. mycobacterial infections); and human genetics applications (including detection of panels of point mutations such as those in cystic fibrosis, detection of pro-coagulation mutations, or cardiovascular risk assessment, or a panel of SNPs for pharmacogenomics of forensic testing. In one format of the assay, one could simply determine whether a patient is wild type or carries a mutation; and known parental point mutations in fetuses from the peripheral blood of known wild-type mothers, without the need for amniocentesis.)

EXAMPLES

This invention is further illustrated by the following non-limiting examples. The contents of all references, patents, and published patent applications cited throughout this application, as well as the Figures and the sequence listing, are incorporated herein by reference.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. U.S. patent application Ser. No. 09/584,905, filed May 30, 2000, Ser. No. 09/724,755, filed Nov. 28, 2000, Ser. No. 10/011,993, filed Dec. 5, 2001, and Patent Cooperation Treaty Application No. PCT/US01/17329, filed May 30, 2001, are hereby expressly incorporated by reference in their entirety for any purpose.

Example 1

Genomic DNA Isolation

Genomic DNA was isolated using the DNeasy Tissue Kit (Qiagen, Valencia, Calif.) (Fukushima, N. Et al. Diagnosing pancreatic cancer using methylation specific PCR analysis of pancreatic juice. *Cancer Biol Ther* 2, 78-83 (2003)).

KRAS2 Sequencing

We PCR amplified the KRAS2 locus using M13-tailed primers (5'-GTAAAACGACGGCCAGG-GAGAGAGGC-CTGCTGAAAA-3' (SEQ ID NO: 1) and 5'-CAGGAAA-CAGCTATGACT-TGGATCATATTCGTCCACA-3' (SEQ ID NO: 2), M13 tails underlined). M13 primers were used for sequencing, the BigDye Terminator 3.1 Cycle Sequencing Kit and an ABI Prism 3100 Genetic Analyzer (Applied Biosystems, Foster City, Calif.).

Population Sequencing of Plasma HIV-1

We sequenced plasma samples diluted at 100,000 copies/ml HIV-1 RNA (using plasma from an individual without HIV-1 infection) with the ViroSeq™ HIV-1 Genotyping System (Celera Diagnostics, Alameda, Calif.). Using this system, HIV-1 RNA was extracted and reverse transcribed. A 40-cycle PCR yields a 1.8 kb PCR product that is purified and sequenced (BigDye®, Applied Biosystems) with seven different primers using an ABI PRISM 3100 Genetic Analyzer.

LigAmp Oligonucleotides and Probes

We purchased oligonucleotides (gel-purified) and M13 primers from Invitrogen, Corp. (Carlsbad, Calif.), and LacZ and 16S rDNA Taqman probes from Integrated DNA Technology (Coralville, Iowa). See Supplementary Table.

KRAS2 and p53 Oligonucleotide Ligation

We performed ligation directly on genomic DNA from cultured cells. For pancreatic duct juice samples, ligation was performed using 60 pg of PCR-amplified KRAS2 DNA (see above). DNA samples were incubated with 1 pmol of each oligonucleotide (either a mutant or wild-type upstream oligonucleotide and a downstream common oligonucleotide) and 4 U Pfu DNA ligase in 1×Pfu Ligase Buffer (Stratagene, La Jolla, Calif.). Samples were denatured at 95° C. for 3 min, and then incubated for 90 two-step cycles of 95° C. for 30 seconds alternating with 65° C. for 4 min. For simultaneous detection of mutant and wild-type KRAS2, both upstream oligonucleotides were included in the reaction; the concentration of the wild-type oligonucleotide was reduced to $10^{-5}$ pmol. For simultaneous detection of KRAS2 and p53 mutations, both upstream and downstream oligonucleotides were included at 1 pmol.

HIV-1 K103N Oligonucleotide Ligation

DNA was amplified from these molecular clones with the ViroSeq system and cloned them using the TOPO TA Cloning Kit (Invitrogen) to generate plasmids containing wild-type and mutant inserts. The plasmids were isolated and sequenced as described. Ligation was performed using either 10 pg of plasmid template or 100 pg of plasma-derived ViroSeq PCR products as described above, except that the upstream oligonucleotide concentration was 2 pmol.

Q-PCR

Q-PCR was performed using a SmartCycler (Cepheid, Sunnyvale, Calif.). Each 25 µl reaction contained 5 pmol forward and 5 pmol reverse M13 primers, 6 µl of the unpurified ligation reaction, 12.5 µl platinum Quantitative PCR SuperMix-UDG (Invitrogen), and 2.5 pmol of lacZ and/or 16S rDNA probes. PCR reactions were pre-incubated at 50° C. for 2 min and 95° C. for 2 min, followed by 50 two-step cycles of 95° C. for 10 seconds alternating with 64° C. for 20 seconds. The cycle threshold was manually set in the middle of the linear range of the amplification curves (log scale).

The LigAmp assay converts single base differences into more distinctive molecules that could be easily detected and quantified. The first step, two oligonucleotides are hybridized to a DNA template and ligated to one another (FIG. 1a). Each of the two oligonucleotides contains a region specific to the target gene (green) and an M13 tail (blue). The M13 tails permit amplification of the ligated product in a subsequent universal Q-PCR detection reaction. The upstream oligonucleotide also contains a region of unique foreign DNA (e.g. lacZ DNA, red) that serves as the binding region for a probe in the Q-PCR reaction. The upstream oligonucleotide was designed to match either the mutant or wild-type sequence at the 3' end. When an upstream mutant oligonucleotide is used (FIG. 1a), the 3' end of the oligonucleotide was designed to perfectly match the mutant template. The same oligonucleotide should mis-pair at the 3' end when hybridized to a wild-type template, preventing ligation (FIG. 1b).

In the second step, the ligated DNA was amplified using M13 primers and detected it in a Q-PCR reaction (FIG. 1c). This step is independent of the specific gene or mutation targeted in the ligation step. Q-PCR amplicons were detected using a universal probe (e.g. lacZ) that contains a fluorophore and quencher. Both the M13 forward primer and the lacZ probe have the same polarity as the upstream ligation oligonucleotide. Therefore, the lacZ probe cannot bind to the ligation oligonucleotide. Binding of the probe requires ligation of the two oligonucleotides (FIG. 1a) followed by polymerization of the complementary (bottom) strand of DNA in the Q-PCR step (FIG. 1c). The Q-PCR probe binds to the bottom strand of the amplified DNA. Extension from the M13 forward primer allows the probe to be cleaved and the fluorophore detected. If no ligation occurs in the first step due to a mispair (FIG. 1b), there is no template for amplification in the Q-PCR step (FIG. 1d).

Figure 1:
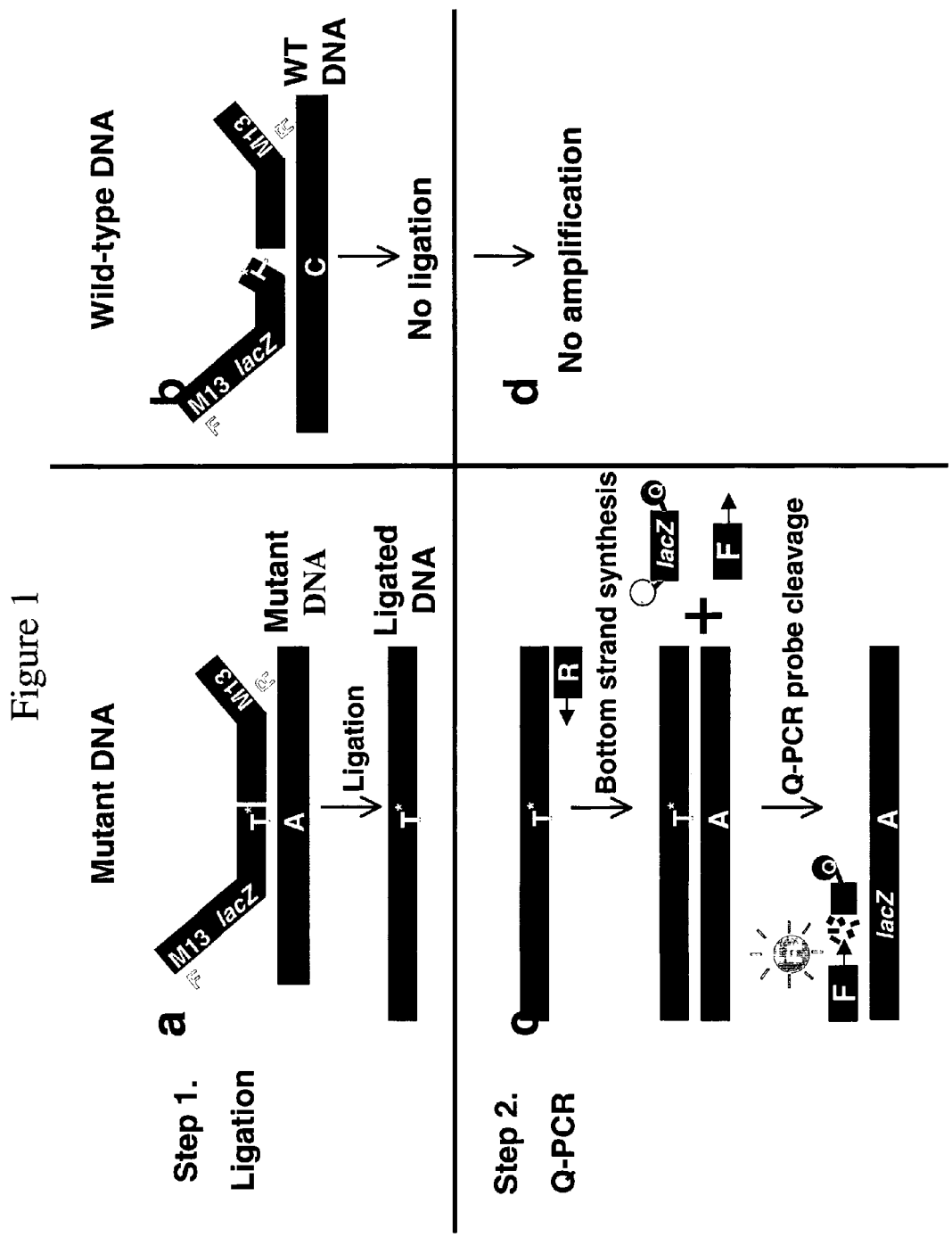
FIG. 1 shows an overview of the LigAmp assay. The LigAmp assay includes two steps: template-dependent ligation of two oligonucleotides (Step 1) and detection and quantification with Q-PCR (Step 2). Details of the LigAmp assay are described in the Results section. F: forward M13 primer, R: reverse M13 primer, FL: fluorophore, Q: quencher. The asterisk indicates the terminal thymidine base on the upstream mutant oligonucleotide.

Since this strategy involves a ligation step followed by an amplification/detection step. LigAmp was used to detect and directly quantify mutant DNA alone (FIG. 1). Alternatively, a pair of mutant and wild-type upstream oligonucleotides were used to simultaneously detect and quantify mutant and wild-type DNA (not shown). In either case, the specificity of LigAmp relies on the differentiating power of a DNA ligase to ligate the upstream and downstream oligonucleotides only when both hybridize to the template with no mismatches at the adjacent terminal nucleotides.

Detection of the KRAS2 Mutation in Cell Line DNA Mixtures

Figure 2:
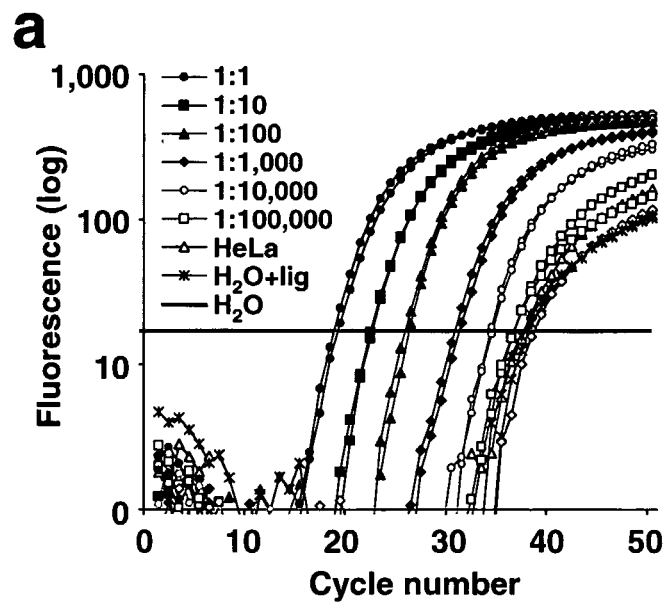
FIG. 2 depicts the detection of genomic DNA containing the KRAS2 mutation. In Q-PCR, amplification occurs at different cycle numbers depending on the initial template concentration. A fluorescence threshold is defined and the cycle at which this threshold is crossed is determined for each sample (horizontal red line, cycle threshold, Ct). (a) Representative Q-PCR amplification curves (in duplicate) of KRAS2 mutant SW480 DNA serially diluted into wild-type (WT) KRAS2 HeLa DNA. The "$H_2O$+lig" sample is a water control that was subjected to both the ligation and Q-PCR steps; the "$H_2O$" sample was only subjected to the Q-PCR step. (b) The mean cycle threshold (Ct) values (six independent assays) were plotted against the dilution of mutant DNA. Error bars: 1 SD. Note that the mean Ct of the 1:10,000 mutant DNA sample plus 3 SD does not overlap with the mean Ct of the HeLa wild-type DNA minus 3 SD. (c) Multiplex detection of mutant and wild-type KRAS2 (in duplicate). KRAS2 mutant SW480 DNA was 10-fold serially diluted into HeLa DNA, and the signals for mutant and wild-type KRAS2 were simultaneously detected in Q-PCR using lacZ and 16S rDNA probes, respectively. The upstream KRAS2 wild-type primer was used at a lower concentration (see Materials and Methods). The wild-type KRAS2 signals for each sample are superimposed (overlapping red curves) with Cts of approximately 34 cycles (black vertical line). The other curves reflect detection of mutant DNA with the mutant probe. (d) Multiplex LigAmp for KRAS2 and p53. Detection of the p53 G818A mutation (CAT, R273H) in SW480 DNA (blue), and the KRAS2 G35A mutation (GAT, G12D) in LS513 DNA (red) using multiplexed ligation oligonucleotides and the lacZ and 16S rDNA probes. Both DNA samples were serially diluted with HeLa cell DNA (wild-type for both mutations).
Figure 2:
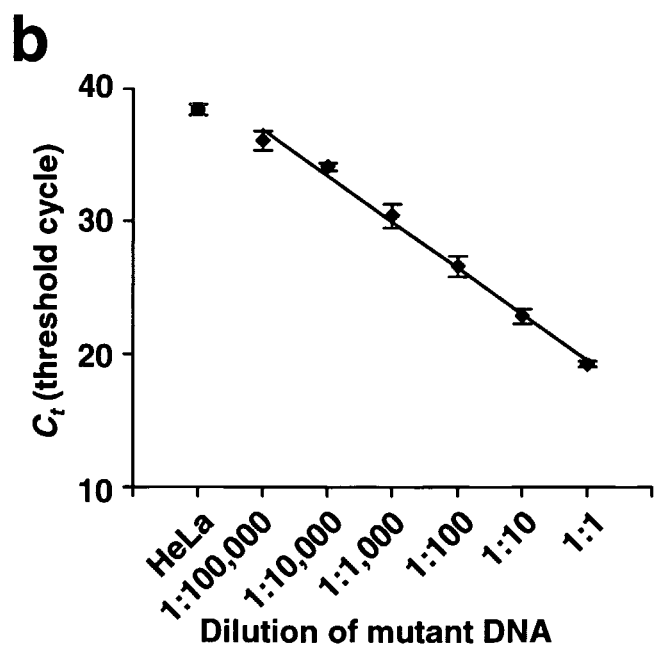
Figure 2:
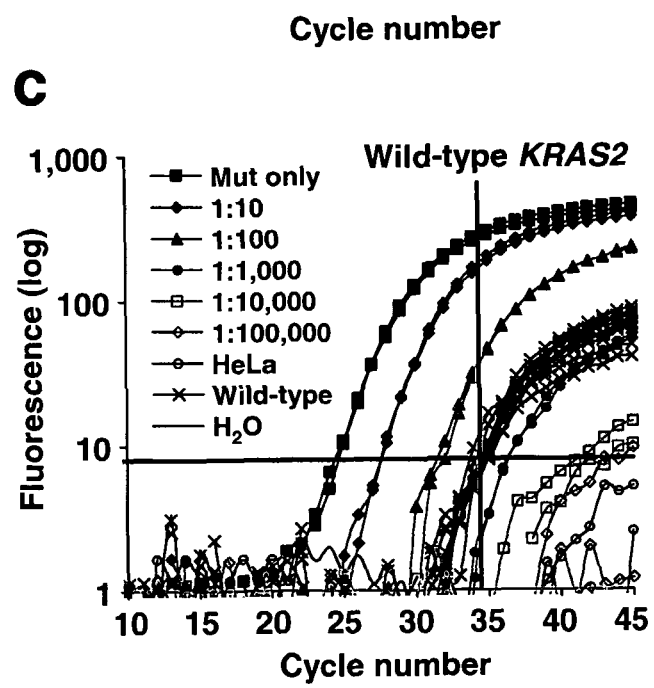
Figure 2:
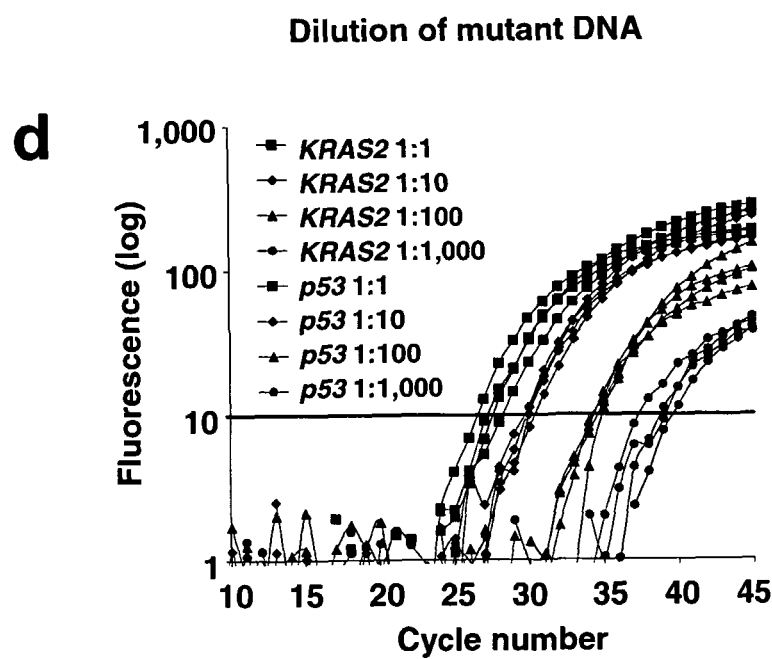

To demonstrate proof-of-principle, DNA from the SW480 colon cancer cell line was serially diluted, which contains a KRAS2 mutation (G35T, GTT, G12V), with HeLa cell line DNA that contains wild-type (GGT) KRAS2 alleles. After ligation of the mutant-specific oligonucleotide to a common oligonucleotide, Q-PCR was performed using M13 primers and a lacZ probe. Mutant KRAS2 DNA was detected as a signal distinct from HeLa DNA at a 1:10,000 dilution (FIG. 2a), and the signal was linear over a wide range of dilutions (FIG. 2b, $r^2$=0.99, least squares analysis). Elimination of ligase from the ligation reaction resulted in no amplification (data not shown).

The LigAmp Reaction can be Multiplexed

Mutant and wild-type KRAS2 DNA was simultaneously detected in a multiplex reaction by including both mutant and wild-type oligonucleotides in one ligation reaction. To maintain a wide linear range of mutant DNA detection, the concentration of the upstream wild-type primer was significantly reduced (see Materials and Methods). Mutant DNA was detected with a lacZ probe, and wild-type DNA with a 16S rDNA probe containing a different fluorophore. When mutant SW480 DNA was serially diluted into wild-type HeLa DNA, the mutant DNA cycle threshold (Ct) varied with input DNA concentration, whereas the wild-type DNA Ct was relatively constant (FIG. 2c). LigAmp was also used to simultaneously detect KRAS2 and p53 mutations in a single ligation reaction (FIG. 2d). The multiplexed reaction detected each mutation in either SW480 DNA or LS513 DNA at dilutions up to 1:1,000. Additional experiments are needed to determine the precise impact of multiplexing on the sensitivity of LigAmp reactions.

Detection of Tumor-Specific KRAS2 Mutations in Pancreatic Juice

Figure 3:
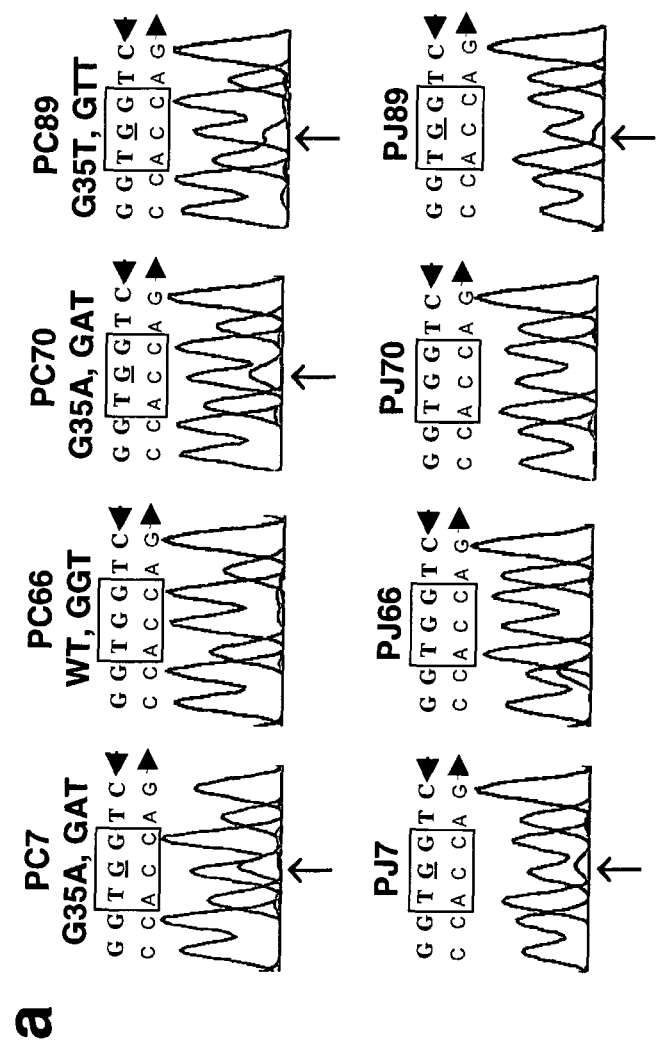
FIG. 3 depicts the detection of mutant KRAS2 sequences in pancreatic duct juice from pancreatic cancer patients by traditional DNA sequencing. (a) KRAS2 DNA was amplified from pancreatic cancer tissue samples (PC, top row) and the corresponding pancreatic duct juice samples obtained from the same patients at the time of surgery (PJ, bottom row), and sequenced as described (see Methods). The electropherograms display antisense sequence. Antisense sequence text (bottom strand, right arrowheads) is in a 5' to 3' orientation and the corresponding sense sequence text (top strand, left arrowheads) is in a 3' to 5' orientation. The three bases for codon 12 are boxed. Peaks representing nucleotide mixtures at codon 12 are indicated below each electropherogram (arrows), and the mutant bases are underlined in the sense sequence. (b-c) LigAmp detection of the G35A (GAT, G12D) and G35T (GTT, G12V) mutations, respectively, in four pancreatic duct juice samples. HeLa DNA was included as a negative control.
Figure 3:
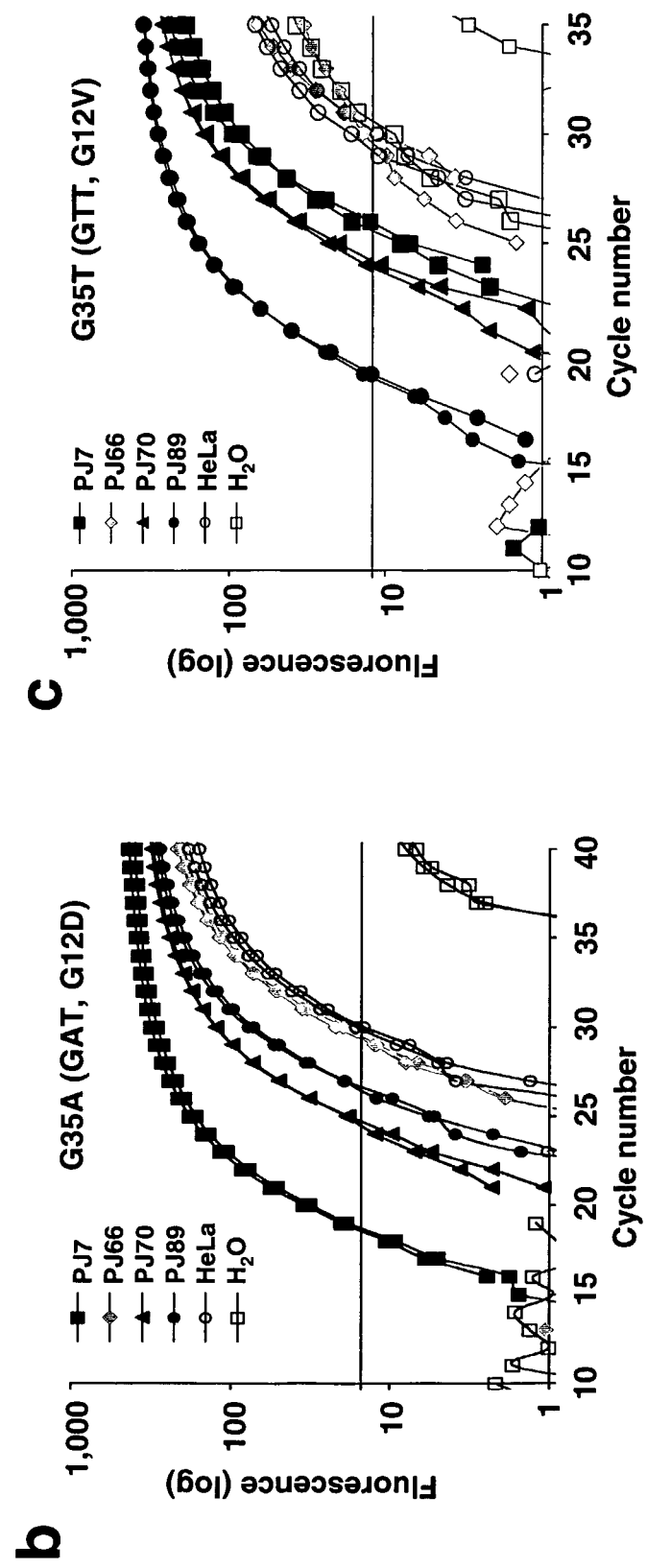

We next tested whether LigAmp could detect KRAS2 mutations in samples from patients with pancreatic cancer. First amplified and sequenced was the hotspot region of the KRAS2 gene from four pancreatic cancer (PC) tissue samples following microdissection. Two samples had the G35A (GAT, G12D) mutation (PC7 and PC70), one had wild-type (GGT) KRAS2 alleles (PC66), and one had the G35T (GTT, G12V) mutation (PC89) (FIG. 3a, top row, arrows). Then sequenced were the pancreatic duct juice (PJ) samples collected from the same patients at the time of surgery (FIG. 3a, bottom row). Two samples (PJ7 and PJ89) had small peaks in the sequencing electropherograms that corresponded to mutations detected in the tumor samples from the same patients (arrows).

LigAmp assays were then performed using KRAS2-amplified DNA from the pancreatic duct juice samples. First, the amount of wild-type DNA was confirmed and was roughly equivalent in the four samples using a wild-type LigAmp reaction (not shown). With oligonucleotides specific for the G35A (GAT) mutation (FIG. 3b), the two tumors known to contain that mutation amplified first (PJ7, blue and PJ70, red). The sample that contained the G35T (GTT) mutation (PJ89, green) amplified between the samples with G35A and the control DNA. Detection of the G35A mutation in this sample could reflect either intra-tumor clonal heterogeneity of KRAS2 mutations (Laghi, L. Et al. Common occurrence of multiple K-RAS mutations in pancreatic cancers with associated precursor lesions and in biliary cancers. Oncogene 21, 4301-6 (2002)), or the presence of high grade PanINs that contributed DNA with the G35A mutation to the pancreatic duct juice. The sample with wild-type alleles (PJ66, gold) overlapped with the control DNA (no G35A detected). With oligonucleotides specific for the G35T (GTT) mutation (FIG. 3c), the pancreatic duct juice from the KRAS2 G35T-bearing tumor (PJ89, green) amplified before the others. The two tumors with G35A mutations (PJ7 and PJ70) were detected at a lower level, and the wild-type tumor (PJ66) overlapped with the control DNA. In both experiments, a low level of non-specific amplification was seen with the control DNA (FIG. 3b,c). The presence of the minor mutant species in the pancreatic duct juice samples (GTT in PJ7, GTT in PJ70, and GAT in PJ89) were independently confirmed using BstN1 restriction enzyme digestion of wild-type alleles (Mitchell, C. E., Belinsky, S. A. & Lechner, J. F. Detection and quantitation of mutant K-ras codon 12 restriction fragments by capillary electrophoresis. Anal Biochem 224, 148-53 (1995)), followed by AS-PCR detection of the GAT and GTT mutations. The presence of the minor mutations in samples PJ70 and PJ89 were further confirmed by cloning the BstN1-refractory PCR products and DNA sequencing (data not shown).

Detection of the K103N Mutation in HIV-1 Plasmids

Figure 4:
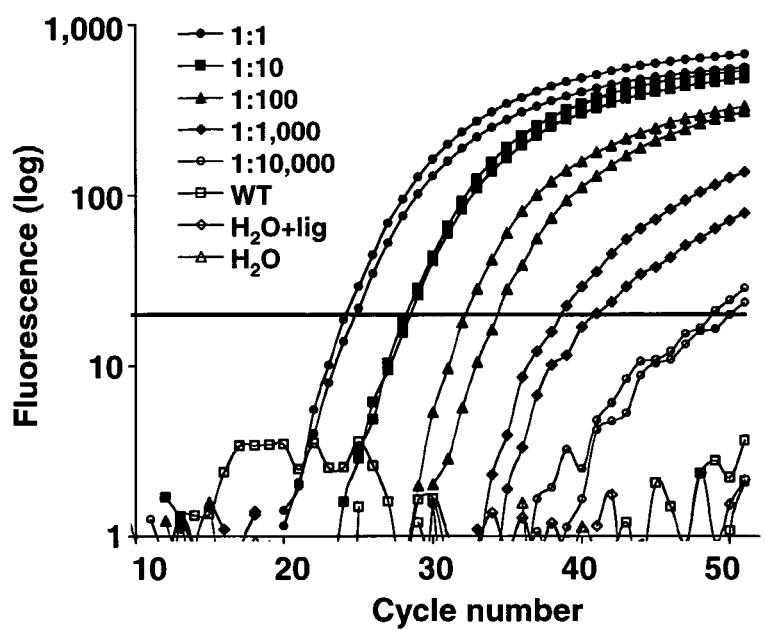
FIG. 4 depicts the detection of the HIV-1 K103N mutation in plasmid mixtures. (a) Representative Q-PCR amplification curves (in duplicate) of K103N mutant plasmid serially diluted with wild-type HIV-1 plasmid. WT=wild-type plasmid alone. Controls ($H_2O$+lig and $H_2O$) are described in the legend for FIG. 2. (b) The mean Ct values (four independent assays) were plotted against the relative concentration of mutant plasmid. Error bars: 1 SD.
Figure 4:
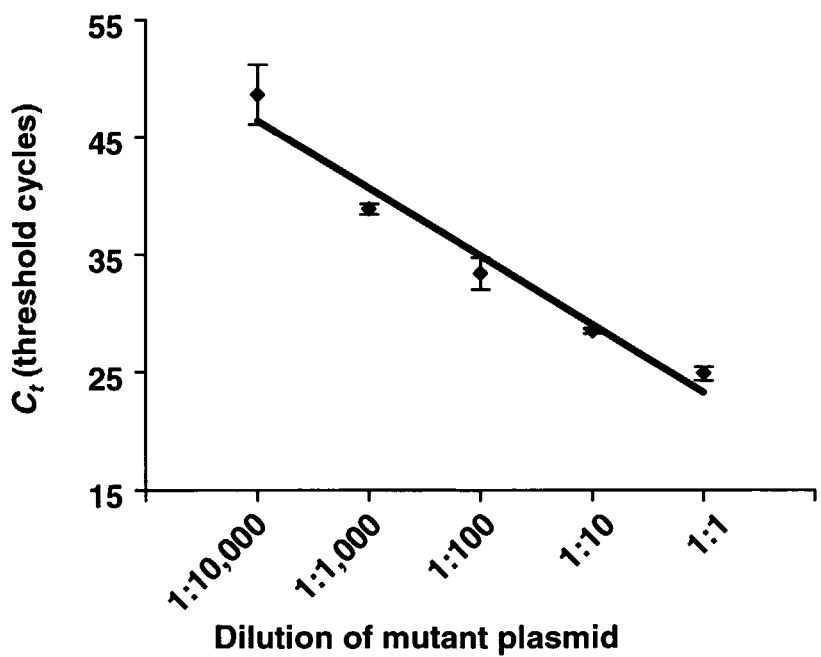

We also used the LigAmp assay to detect the K103N HIV-1 drug resistance mutation. Both the mutant and wild-type upstream oligonucleotides contained an additional base substitution (A→G) at the third base from the 3' terminus of the upstream oligonucleotide (FIG. 5a, the first base of codon 103, underlined G), to enhance specificity of the oligonucleotides for their respective templates. Mixtures of plasmids with wild-type (K=AAA) or mutant (N=AAC) sequences at codon 103 were prepared, and ligation was performed using mutant upstream and common downstream oligonucleotides (FIG. 4). Q-PCR was performed using M13 primers and a lacZ probe. The K103N mutation was detected at a dilution of 1:10,000(0.01%, FIG. 4a); detection was linear over the full range of dilutions tested ($r^2$=0.96, least squares analysis, FIG. 4b). Experiments performed with a wild-type upstream oligonucleotide confirmed the specificity of the assay (not shown).

Detection of the K103N Mutation in Plasma from HIV-1 Infected Individuals

Figure 5:
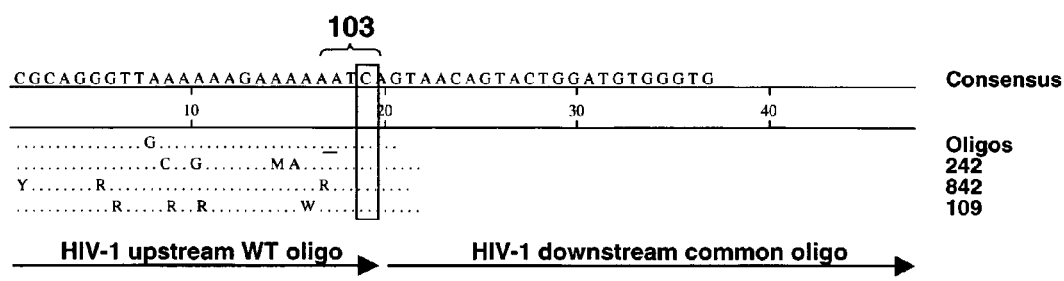
FIG. 5 depicts population sequencing and LigAmp analysis of HIV-1 in plasma samples. (a) Plasma HIV-1 from subjects 242, 842, and 109 were sequenced with the ViroSeq system (population sequencing). Those sequences (SEQ ID NOS 33-36, respectively, in order of appearance) were aligned with sequences of the HIV-1 upstream WT and downstream common oligonucleotides (arrows) using MegAlign (DNAStar, Madison, Wis.). A consensus sequence is shown at the top (SEQ ID NO: 32). Nucleotides at the third position of codon 103 (bracket) are boxed. An A→G substitution at the first base of codon 103 in the upstream wild-type and mutant oligonucleotides (underlined) enhances specificity of the ligation reaction. Dots indicate nucleotides that match the consensus sequence. Nucleotide mixtures are indicated using IUB codes. (b-c, left) Plasma HIV-1 was analyzed using the ViroSeq system. Electropherograms show sequences near codon 103 in HIV-1 reverse transcriptase. Arrowheads indicate the orientation of ViroSeq sequencing primers. The sequence of the HXB2 reference strain ("Ref") is shown above the sequence of each sample. Amino acids encoded by the reference sequence (above) and the sample sequence (below) are shown at the top of each panel. The nucleotide at the third position of codon 103 is boxed. A mixture of nucleotides (A and G=R) is present at this position in the sequence from subject 109 (c); the lower case designation (r) indicates that the nucleotide sequence was manually edited. (b-c, right) Q-PCR amplification curves from subjects 242 and 109, respectively. Curves were generated using either the mutant (Mut, red) or wild-type (WT, blue) upstream oligonucleotide. (d) Plasma from subject 242 (mostly HIV-1 with the K103N mutation) was serially diluted with plasma from subject 109 (mostly wild-type HIV-1). The percentage of plasma from subject 242 in the samples was 100%, 10%, 1%, 0.1%, 0.01% and 0%, all at 50,000 copies/ml HIV-1 RNA. DNA was amplified from the plasma mixtures using the ViroSeq system. LigAmp was performed using the upstream mutant oligonucleotide for detection of K103N. Ct values were plotted against the dilution of sample 242 (red dots and line). The Ct of the sample of plasma from subject 109 only (blue dot, arrow) was similar to the Ct obtained with a 1:1,000 dilution of plasma from subject 242.
Figure 5:
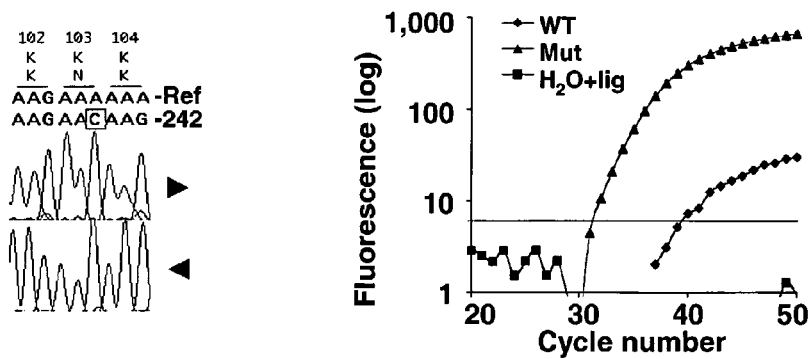
Figure 5:
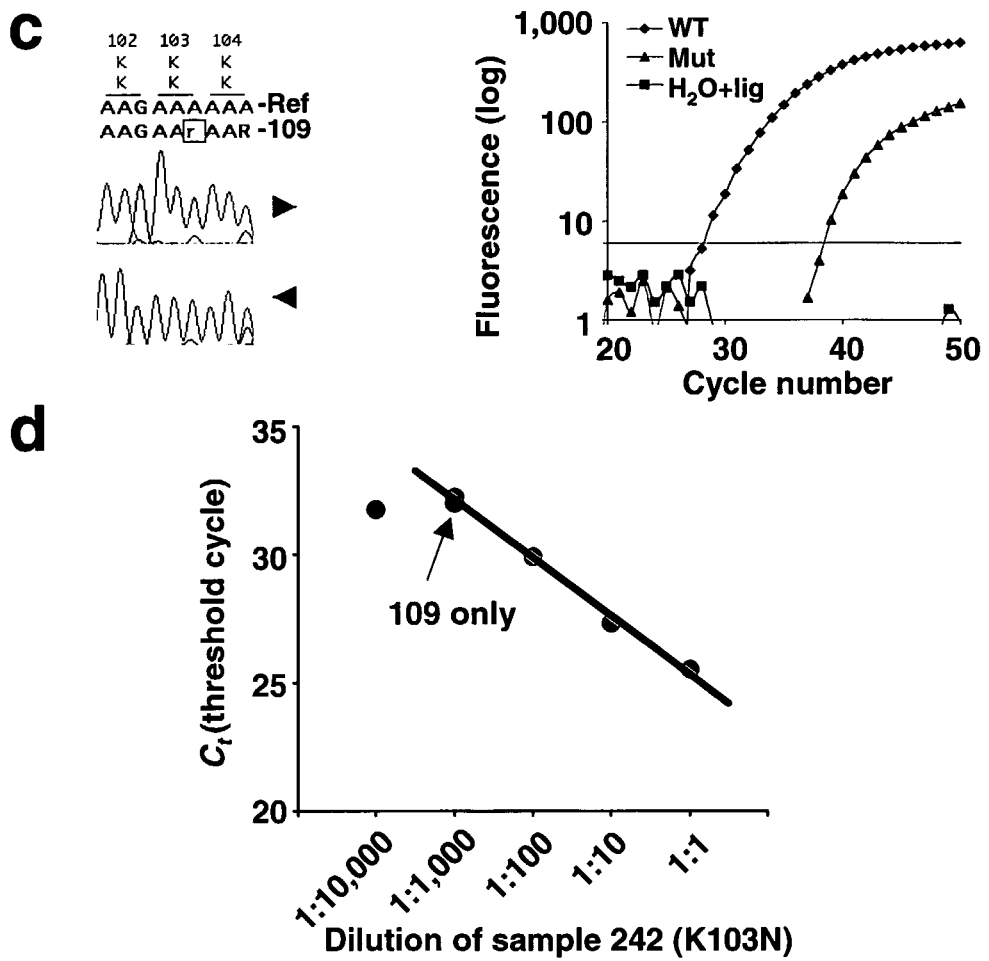

We then used the LigAmp assay to detect K103N in plasma samples from HIV-1 infected individuals. First performed was HIV-1 genotyping (population sequencing) to detect the major population of viruses in each sample. At codon 103, subject 242 had N=AAC (mutant, FIG. 5b), subject 109 had K=AAR=AAA/G (wild-type, FIG. 5c), and subject 842 had K=AAA (wild-type, not shown). The HIV-1 sequences in the samples differed from the sequences of the LigAmp oligonucleotides at 3 or 4 positions (FIG. 5a), reflecting the natural genetic diversity of HIV-1 in infected individuals. Analysis of sample 242 with mutant and wild-type upstream oligonucleotides yielded Cts of 31.6 and 38.9, respectively (FIG. 5b, right). This indicates that viruses with K103N represent the major viral population, and that a low-level of wild-type HIV-1 is also present. Analysis of samples 109 (FIG. 5c, right) and 842 (not shown) yielded lower Cts with the wild-type oligonucleotide than with the mutant oligonucleotide, consistent with the genotyping results. In both samples, Q-PCR achieved threshold using the mutant upstream oligonucleotide, which was not the case when a pure wild-type plasmid was tested (FIG. 4). This suggests that the K103N mutation was present at a low level in both samples. The difference in the Cts obtained with the mutant vs. Wild-type oligonucleotides was 8.3 for subject 842 and 10.3 for subject 109.

Detection of the K103N Mutation in a Plasma Dilution Panel

Additional assays were performed using samples prepared by serially diluting plasma from subject 242 (mostly mutant) with plasma from subject 109 (mostly wild-type). Each sample was independently subjected to HIV-1 RNA extraction, reverse transcription, and PCR amplification prior to analysis. LigAmp detected the K103N mutation in the mixtures at a dilution of 1:1,000 (0.1%, $r^2$=0.998, least squares analysis, FIG. 5d). Similar results were obtained using the 1:1,000 dilution, further 10-fold dilutions, and plasma from subject 109 alone (FIG. 5d), suggesting that plasma from subject 109 contained a minor population of viruses with the K103N mutation (approximately 0.1%).

It was demonstrate that the LigAmp assay can detect single base mutations in the presence of a vast excess of wild-type DNA. A sensitivity of $10^{-3}$ to $10^{-4}$ was easily obtained for detection of point mutations in genomic DNA and HIV cDNA. Several factors could potentially interfere with the sensitivity of LigAmp for analysis of clinical samples. Mutations present at very low levels could be lost through sampling error or "bottlenecking". Some samples might also contain DNA ligase inhibitors (Prieto-Alamo, M. J. & Laval, F. Deficient DNA-ligase activity in the metabolic disease tyrosinemia type I. *Proc Natl Acad Sci USA* 95, 12614-8 (1998) and Ciarrocchi, G., MacPhee, D. G., Deady, L. W. & Tilley, L. Specific inhibition of the eubacterial DNA ligase by arylamino compounds. *Antimicrob Agents Chemother* 43, 2766-72 (1999)). Mutation detection could also be hampered by biased amplification during the sample prep PCR or Q-PCR. For these reasons, the sensitivities obtained using control reagents may be better than those obtained when the system is validated using blinded panels and clinical specimens. The type of template used may also influence the efficiency of the LigAmp assay. Cts are slightly lower when PCR products are used for templates rather than plasmids to generate standard curves, and when PCR products contain dUTP. Samples used to generate standard curves and the test samples, when generated in the same way, increase the sensitivity of the reaction. Accurate quantification of template DNA increases the sensitivity of the analysis; the Q-PCR reaction is quite sensitive to template concentration if a single oligonucleotide (e.g. mutant) is used. When template concentration is carefully controlled, LigAmp results correlate closely with the percentage of mutant DNA (FIGS. 2b and 4b). Use of an internal standard with each reaction may also be helpful.

While the specificity of LigAmp is quite high, it was observed that low-level non-specific amplification of wild-type templates in some experiments (FIGS. 2a and 3b,c). Non-specific signals could arise during ligation, reflecting either low-level ligation of oligonucleotides despite terminal mismatches with the template, or template-independent oligonucleotide ligation (Barringer, K. J., Orgel, L., Wahl, G. & Gingeras, T. R. Blunt-end and single-strand ligations by *Escherichia coli* ligase: influence on an in vitro amplification scheme. *Gene* 89, 117-22 (1990)). Alternatively, non-specific signals could be generated during Q-PCR. Unligated oligonucleotides were not removed prior to Q-PCR, and these might extend on mismatched wild-type templates during Q-PCR by Taq polymerase. M13 reverse primers could then extend from unligated downstream oligonucleotides, producing a complementary strand. Since the extended products are complementary to each other, non-specific amplification might then occur. Experiments are in progress to identify factors contributing to non-specific signals in the assay.

LigAmp requires the use of high-quality oligonucleotides. Synthetic errors in the oligonucleotides could influence sensitivity and specificity of the assay. Gel-purified oligonucleotides were used for ligation, and it is not clear if unpurified oligonucleotides would perform as well. Other factors, such as pipetting error or unequal thermal cycling temperatures during ligation or Q-PCR, could also potentially lead to inaccurate results. LigAmp is easily adapted for detection of any single base difference. LigAmp can also be performed as a multiplex reaction for simultaneous detection of mutant and wild-type DNA, or for simultaneous detection of different mutations. Analysis of mutations in HIV-1 poses unique challenges because of viral genetic diversity. Samples from three subjects using a single oligonucleotide set were tested. None of the subjects had other drug resistance mutations near K103N. However, there were numerous nucleotide differences in the oligonucleotide binding regions. Those differences did not appear to hamper detection of the K103N mutation. Analysis of WT/K103N plasmid pairs from other individuals indicates that nucleotide diversity near K103N can be overcome by extending the length of the oligonucleotides and lowering the ligation temperature (not shown). Different primer sets may be needed for different HIV subtypes. Some HIV-1 variants have other mutations at codon 103 (e.g. K103E, K103R, and K103T). Specific oligonucleotides would be needed to detect each of those unusual mutations. It is difficult to define the limit of sensitivity of LigAmp for HIV-1 mutation detection using clinical samples, since many samples that are genotypically wild-type are felt to harbor minority variants with drug resistance mutations (Havlir, D. V., Eastman, S., Gamst, A. & Richman, D. D. Nevirapine-resistant human immunodeficiency virus: kinetics of replication and estimated prevalence in untreated patients. *J Virol* 70, 7894-9 (1996) and Hirsch, M. S. Et al. Antiretroviral drug resistance testing in adults with HIV infection: implications for clinical management. International AIDS Society—USA Panel. *Jama* 279, 1984-91 (1998)). Using plasmid mixtures, K103N was detected at a level of 0.01%. K103N was also detected at low levels in two patients who had only the wild-type sequence detected with an FDA-cleared genotyping assay. A dilution experiment suggested that K103N was present at approximately 0.1% in one of those patients. LigAmp can be performed using PCR products remaining from routine HIV-1 genotyping. Because PCR products are used at low concentrations, numerous mutations can be analyzed using PCR products remaining after genotyping a single 0.5 ml plasma sample.

LigAmp also has applications in genetics, including prenatal diagnosis (e.g. multiplex detection of common CFTR mutations) (Chiu, R. W. Et al. Prenatal exclusion of beta thalassaemia major by examination of maternal plasma. *Lancet* 360, 998-1000 (2002)). Using LigAmp, it is possible to detect point mutations in fetal cells circulating in maternal peripheral blood, avoiding the need for amniocentesis or chorionic villous sampling procedures (Yukobowich, E. Et al. Risk of fetal loss in twin pregnancies undergoing second trimester amniocentesis (1). *Obstet Gynecol* 98, 231-4 (2001) and Jackson, L. G. Et al. A randomized comparison of transcervical and transabdominal chorionic-villus sampling. The U.S. National Institute of Child Health and Human Development Chorionic-Villus Sampling and Amniocentesis Study Group. *N Engl J Med* 327, 594-8 (1992)).

Example 2

DNA Extraction

Genomic DNA was prepared from Hela (KRAS2 wild-type, GGT), SW480 (GTT) and LS513 (GAT) cell lines and the formalin-fixed, paraffin embedded pancreatic cancer blocks using QiAamp DNeasy Tissue Kit (Qiagen, Valencia, Calif.). All patients in this study were operative candidates (Whipple procedure) and the pancreatic duct juice samples were collected intra-operatively and genomic DNA isolated using the QIAamp DNA Blood Mini Kit (Qiagen).

KRAS2 Sequencing

KRAS2 sequencing was performed on pancreatic cancer DNA by PCR amplifying the KRAS2 locus (including codon 12) using the upstream 5'-GTAAAACGACGGCCAGG-GAGAGAGGCCTGCTGAAAA-3' (SEQ ID NO: 1) and downstream 5'-CAGGAAACAGCTATGACT-TGGAT-CATATTCGTCCACA-3' (SEQ ID NO: 2) M13 tailed (underlined regions) primers. Sequencing was then performed using M13 forward or reverse primers, BigDye 3.1 and a 3100 capillary sequencer (ABI, Applied Biosystems (Foster City, Calif.).

LigAmp Oligonucleotides and Probes

Ligation oligonucleotides for wild-type and mutant KRAS2 and modified M13 forward and reverse primers (Table 1) were purchased from Invitrogen, Corp. (Carlsbad, Calif.). The downstream common oligonucleotides were phosphorylated at the 5' end. The LacZ and 16S rDNA Taqman probes containing different fluorophores and quenchers (Table 1) were purchased from Integrated DNA Technology (Coralville, Iowa).

TABLE 1

| | | Oligonucleotides and probes |
|---|---|---|
| KRAS2 Ligation Oligos (Upstream) | GTT | 5'-A<u>CTGTAAAACGACGGCCAGTGT</u>-*TCCCCTCAAACTGGCAGATGCACG*-C-TTGTGGTAGTTGGAGC[T]GT*-3' |
| | GAT | 5'-A<u>CTGTAAAACGACGGCCAGTGT</u>-*TCCCCTCAAACTGGCAGATGCACG*-C-TTGTGGTAGTTGGAGC[T]GA*-3' |
| | CGT | 5'-A<u>CTGTAAAACGACGGCCAGTGT</u>-*TCCCCTCAAACTGGCAGATGCACG*-AACTTGTGGTAGTTGGAG[T]TC*-3' |
| | GGT (Wild-type) | 5'-A<u>CTGTAAAACGACGGCCAGTGT</u>-*CGTATTACCGCGGCTGCTGGCACC*-TTGTGGTAGTTGGAGCTGG*-3' |
| KRAS2 Common (Downstream) | 12b | 5'-PO$^4$-TGGCGTAGGCAAGAGTGCC-<u>TGGTCATAGCTGTTTCCTGCA</u>-3' |
| | 12a | 5'-PO$^4$-GTGGCGTAGGCAAGAGTGCC-<u>TGGTCATAGCTGTTTCCTGCA</u>-3' |
| M13 primers | Forward | 5'-CTGTAAAACGACGGCCAGTG-3' |
| | Reverse | 5'-TGCAGGAAACAGCTATGACCA-3' |
| TaqMan Probes | lacZ | FAM-5'-TCCCCTCAAACTGGCAGATGCACG-3'-BHQ-1 |
| | 16S rDNA | ROX-5'-CGTATTACCGCGGCTGCTGGCAC-3'-BHQ-2 |

Underlined: M13 primer binding regions. Italics: probe binding regions (lacZ or 16S rDNA). Bold: gene specific region regions. Asterisk: terminal bases with perfect homology to either the wild-type or mutant sequences. FAM: 6-carboxyflurorescein. ROX: 6-carboxy-X-rhodamine. BHQ: black hole quencher. Boxed base: An additional mis-pair in the upstream mutant oligonucleotides was introduced at the third base from the 3' end to improve the specificity of the assay.

TABLE 2

| | | Oligonucleotides and probes |
|---|---|---|
| KRAS2 Ligation Oligos | KRAS2 G35T (GTT) mutant upstream | 5'-A<u>CTGTAAAACGACGGCCAGTGT</u>-*TCCCCTCAAACTGGCAGATGCACG*-C-TTGTGGTAGTTGGAGCTGT*-3' |
| | KRAS2 G35A (GAT) mutant upstream | 5'-A<u>CTGTAAAACGACGGCCAGTGT</u>-*TCCCCTCAAACTGGCAGATGCACG*-C-TTGTGGTAGTTGGAGCTGA*-3' |
| | KRAS2 wild-type (GGT) upstream | 5'-A-<u>CTGTAAAACGACGGCCAGTGT</u>-*CGTATTACCGCGGCTGCTGGCAC*-C-TTGTGGTAGTTGGAGCTGG*-3' |
| | KRAS2 common downstream | 5'-PO$^4$-TGGCGTAGGCAAGAGTGCC-<u>TGGTCATAGC TGTTTCCTGCA</u>-3' |

TABLE 2-continued

Oligonucleotides and probes

| | | |
|---|---|---|
| p53 Ligation Oligos | p53 G818A mutant upstream | 5'-A<u>CTGTAAAACGACGGCCAGTGT</u>-*CGTATTACCGCGGCTGCTGGCAC*-GAACAGCTTTGAGGT[A]CA\*-3' |
| | p53 common downstream | 5'-PO⁴-TGTTTGTGCCTGTCCTGGGAG-*TGGTCATAGCTGTTTCCTGCA*-3' |
| HIV-1 Ligation Oligos | HIV-1 mutant upstream | 5'-A<u>CTGTAAAACGACGGCCAGTGT</u>-*TCCCCTCAAACTGGCAGATGCACG*-CGCAGGGTTAAAAAAG[G]AC\*-3' |
| | HIV-1 wild-type upstream | 5'-A<u>CTGTAAAACGACGGCCAGTGT</u>-*TCCCCTCAAACTGGCAGATGCACG*-CGCAGGGTTAAAAAAG[G]AA\*-3' |
| | HIV-1 common downstream | 5'-PO⁴-AAATCAGTAACAGTAC TGGATGTGGGTG-*TGGTCATAGCTGTTTCCTGCA*-3' |
| Amplification Primers Probes | M13 forward M13 reverse lacZ probe 16S rDNA | 5'-CTGTAAAACGACGGCCAGTG-3' 5'-TGCAGGAAACAGCTATGACCA-3' FAM-5'-TCCCCTCAAACTGGCAGATGCACG-3'-BHQ-1 ROX-5'-CGTATTACCGCGGCTGCTGGCAC-3'-BHQ-2 |

Underlined: M13 primer binding regions. Italics: probe binding regions (lacZ or 16S rDNA). Bold: gene specific region regions. Asterisk: terminal bases with perfect homology to either the wild-type or mutant sequences. FAM: 6-carboxyflurorescein. ROX: 6-carboxy-X-rhodamine. BHQ: black hole quencher. Boxed base: An additional mis-pair in the upstream HIV-1 mutant oligonucleotide was introduced at the third base from the 3' end to improve the specificity of the assay (the usual mutant 3' terminal sequence is GAAC).

LigAmp Assay

A region of KRAS2 including KRAS2 codon 12 (hot spot) was first PCR amplified using 5'-GGAGAGAGGCCTGCT-GAAAA-3' (SEQ ID NO: 18) and 5'-AATGATTCTGAATT-AGCTGTATCGTCA-3' (SEQ ID NO: 19) primers. For CGT KRAS2 mutation, the mutant KRAS2 DNA was amplified from a plasmid containing the mutant KRAS2 sequence. GTT, GAT and wild-type KRAS2 DNA were amplified from SW480, LS513 and Hela cell genomic DNA, respectively. To construct standard quantitative curves for mutant DNA, amplified mutant KRAS2 from the cell lines was serially diluted into wild-type DNA. Wild-type KRAS2 DNA was also serially diluted to quantify amounts of wild-type DNA. Concentrations of standard mutant and wild-type KRAS2 DNA were determined using NanoDrop (NanoDrop Technologies, Wilmington, Del.). Juice amplified KRAS2 DNA were diluted at 1/100prior to LigAmp analysis. Mutant DNA mixtures and diluted DNA were incubated with ligation oligonucleotides and 4 U Pfu DNA ligase in 1×Pfu Ligase Buffer (Stratagene, La Jolla, Calif.). Ligation reactions were first denatured at 95° C. for 3 min, and then incubated for 90 two-step cycles of 95° C. for 30 seconds alternating with 65° C. for 4 min. To simultaneously determine mutant and wild-type KRAS2, both wild-type and mutant upstream oligonucleotides were included in the reaction. The concentrations for mutant upstream and common downstream oligonucleotides were 1 pmol and 0.5 pmol, respectively, while the concentration for the wild-type upstream oligonucleotide was reduced to 1 fmol. This maintained the full range of mutant DNA detection.

Q-PCR was performed using a SmartCycler (Cepheid, Sunnyvale, Calif.). Each 25 µl reaction contained 5 pmol forward and 5 pmol reverse M13 primers, 2 µl of the unpurified ligation reaction, 12.5 µl platinum Quantitative PCR SuperMix-UDG (Invitrogen), and 2.5 pmol of LacZ and 16S rDNA probes. PCR reactions were pre-incubated at 50° C. for 2 min and 95° C. for 2 min, followed by 40 two-step cycles of 95° C. for 10 seconds alternating with 64° C. for 20 seconds. The cycle threshold was manually set in the middle of the linear range of the amplification curves (log scale).

Restriction Digestion Analysis of KRAS2 PCR Products

To eliminate wild-type and enrich for mutant KRAS2, KRAS2 DNA was first amplified using a forward mutant primer that produces a BstN1 restriction enzyme recognition site when the wild-type allele is amplified [Mitchell, 1995 #41] (F: 5'-AATATAAACTTGTGGTAGTTGGACCT-3' (SEQ ID NO: 20), R: 5'-TCAAAGACAAGGCGATATGC T-3' (SEQ ID NO: 21), underlined cytosine introduced to create the BstN1 site). A 30-cycle PCR using AmpliTaq Gold® DNA polymerase (ABI) was performed, yielding a 1031 by PCR product. A second BstN1 site that cuts both the wild-type and mutant KRAS2 is 136 bases upstream of the reverse primer (mutant: 136 and 906 bases; wild-type: 18, 136 and 888 bases).

Following purification using Qiagen PCR purification Kit, the PCR product (5 µl) was digested with BstN1 (20 units, NEBL, New England Biolabs, Beverly, USA) at 65° C. for 2 hours, and analyzed by 2% agarose gel. To confirm co-existence of a minor mutation in the presence of a dominant mutation, a second digestion was employed to eliminate the dominant mutant molecules. For juice samples containing dominant GAT mutation, the BstN1 digested product (1 µl) was then re-amplified for 35 cycles using the same forward primer, which bears a Bcc I restriction site in the present of mutant GAT KRAS2, and a reverse primer (5'-CCCTGA-CATACTCCCAAGGA-3' (SEQ ID NO: 22)) to produce a 304 bp PCR product. This amplified product was digested with 20 unit Bcc I (NEBL) at 37° C. for overnight. For samples with dominant GTT mutation, 1 µl BstN1 digested product was then re-amplified using a forward primer to produce an hpyCH4 III site for mutant GTT KRAS2, and digested (hypCH4 III (NEBL), 37° C. overnight). The BccI and hpyCH4 III digested products were further amplified and subsequently purified using Qiagen PCR purification kit. Hela DNA similarly treated as a negative control.

T-A Cloning and Sequencing

The purified BstN1/BccI and BstN1/hpyCH4 refractory PCR products were cloned into the pCRII-TOPO® cloning vector using the TOPO TA Cloning® Kit, Version N (Invitrogen). Colony PCR was performed on 10-20 white colonies using M13 forward and reverse primers. These PCR products were then subjected to BstN1 digestion. The BstN1-refractory PCR products were sequenced as above using an M13 forward primer.

KRAS2 Mutational Status in Pancreatic Cancers.

A series of 27 pancreatic cancer specimens were identified, and first examined the KRAS2 gene status in them. The hotspot region of KRAS2 gene was amplified following manual microdissection. Direct DNA sequencing detected KRAS2 mutations at codon 12 in 17 of 27 cases. These mutations included GAT ($12/17$, 71%), GTT ($1/17$, 6%), CGT ($4/17$, 23%). The GAT mutation was the most frequent mutation detected in these specimens, consistent with results from other studies (Luttges, 1999; Pellegata, 1994; and Laghi, 2002).

LigAmp Strategy for Sensitive Point Mutation Detection

Figure 6:
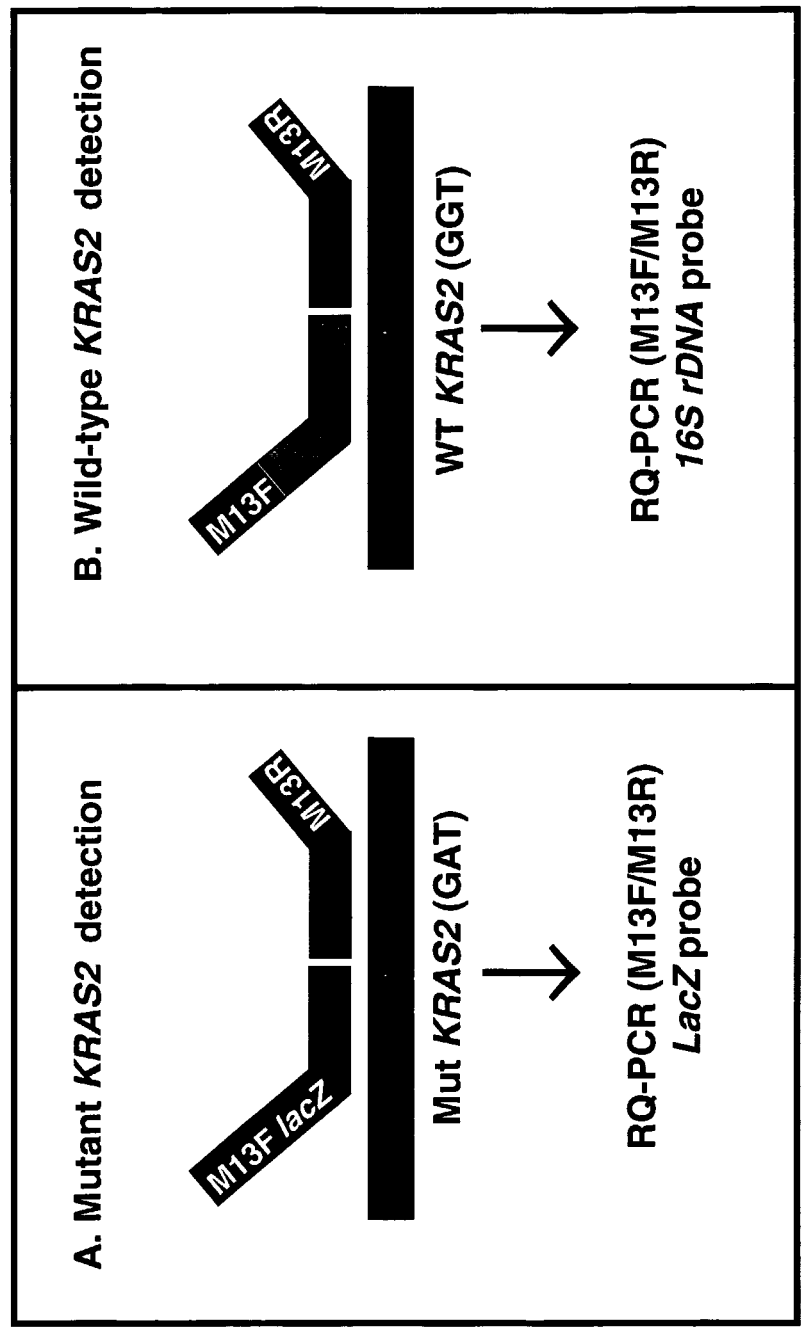
FIG. 6 depicts the strategy for multiplex LigAmp to simultaneously detect mutant and wild-type KRAS2. A: LigAmp detection of mutant KRAS2 (GAT). B: LigAmp detection of wild-type KRAS2 (GGT). In the ligation step, both mutant and wild-type upstream ligation oligonucleotides were included at a ratio of 1000:1. In Q-PCR, lacZ and 16S rDNA probes with different fluorescence's labeled were used to detect mutant and wild-type ligation products, respectively.

To quantify mutant KRAS2 DNA in pancreatic juice, mutant and wild-type KRAS2 DNA levels were simultaneously determined in a multiplex LigAmp reaction including both mutant and wild-type oligonucleotides (Shi, 2004). FIG. 6 demonstrates the LigAmp multiplex strategy to detect mutant and wild-type KRAS2, where each is converted into a unique foreign probe site. The upstream oligonucleotide for mutant KRAS2 contains a region of LacZ DNA and that for wild-type contains a 16S rDNA sequence. Following ligation, both wild-type and mutant ligated products were amplified using M13 forward and reverse primers. The mutant DNA is detected with a LacZ taqman probe and the wild-type DNA with a 16S rDNA probe containing a different fluorophore. To maintain a wide linear range of mutant DNA detection, the concentration of the upstream wild-type oligonucleotide was significantly reduced. At a ratio of 1:1000, at least 0.01% mutant KRAS2 in serially diluted cell mixtures was detected (data not shown). Inclusion of the wild-type oligonucleotide also greatly enhanced specificity of detection, and no amplification signal was observed using pure wild-type Hela DNA.

LigAmp Analysis of Pancreatic Duct Juice from KRAS2 Mutant Cancers

To quantify amount the relative levels of mutant and wild-type KRAS2 DNA in juice samples, LigAmp reactions were performed to simultaneously detect mutant and wild-type KRAS2. Standard quantitative curves were generated for each both wild-type and each mutant KRAS2 using Ct values from and concentrations of these serially diluted pure samples. The amounts of both wild-type and mutant KRAS in pancreatic juice were then obtained from their corresponding standard curves. And the relative percent calculated.

Figure 7A:
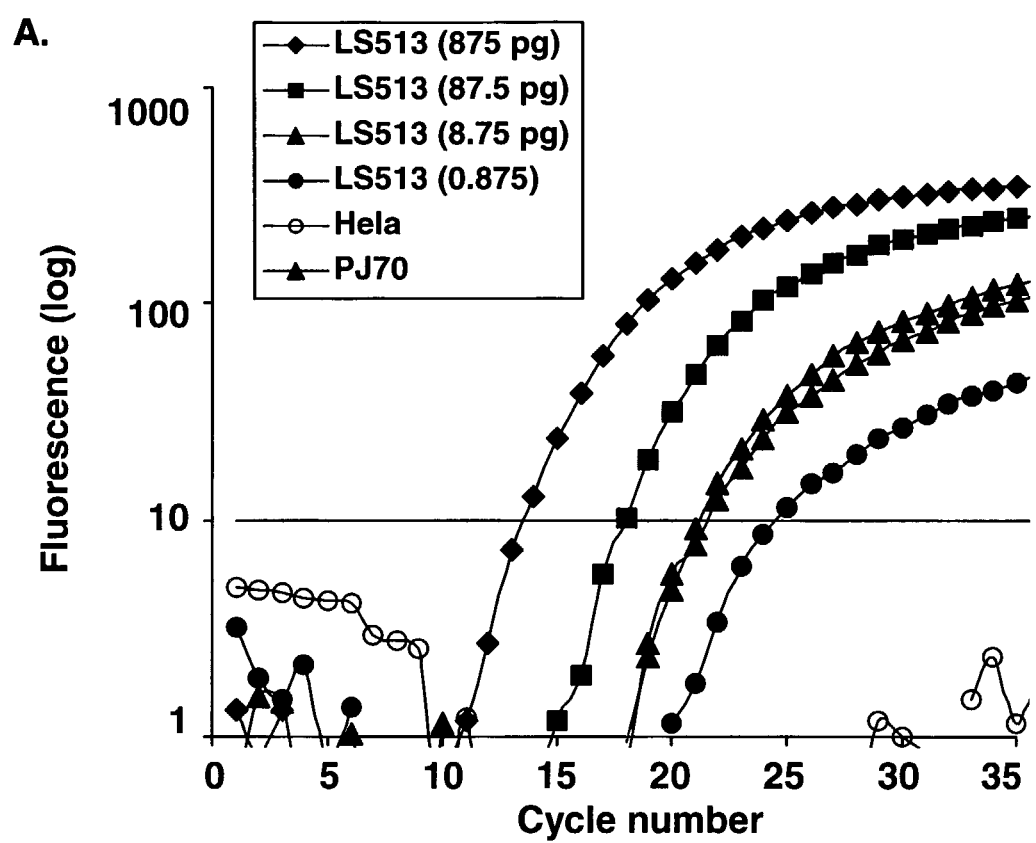
FIG. 7 depicts the . representative LigAmp quantification of mutant KRAS2. A. Representative Q-PCR amplification curves for serially diluted mutant KRAS2 DNA (blue) and a juice sample, PJ70 (red). B. The Ct values from the Q-PCR amplification curves shown in panel A plotted against the concentration of serially diluted mutant KRAS2 (blue). The amount of mutant KRAS2 in PJ70 was obtained from the standard curve (shown as red) based on its Ct value.
Figure 7B:
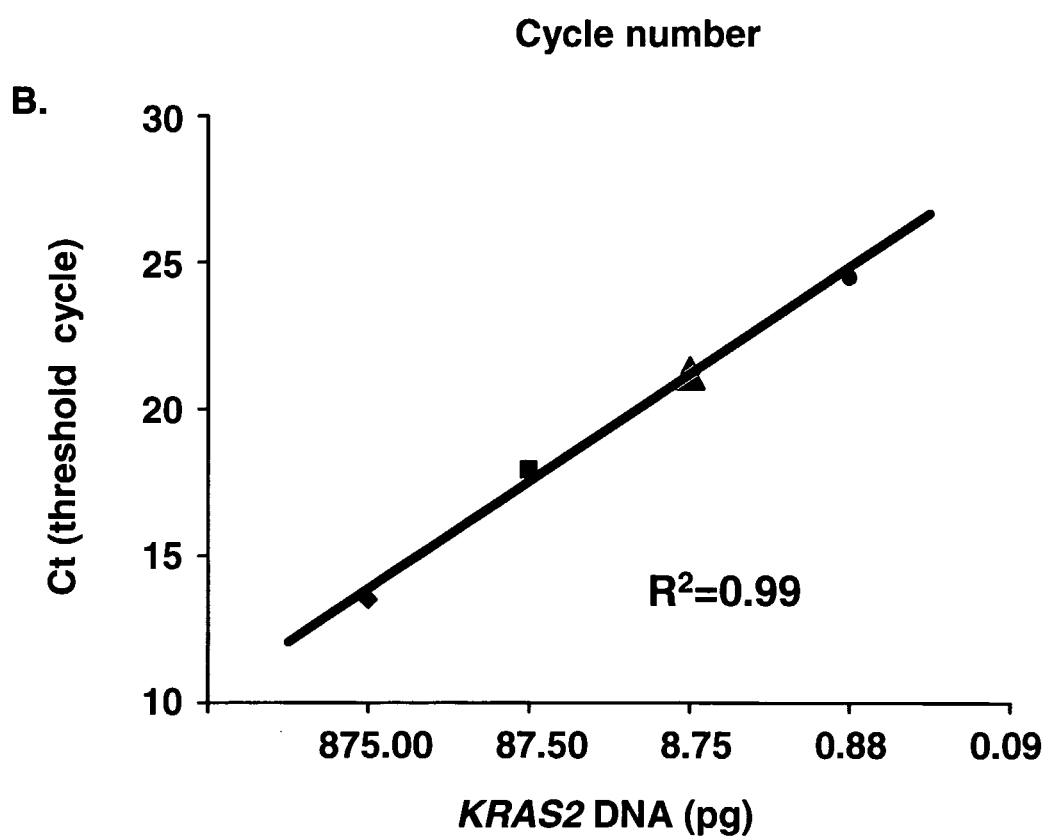

FIG. 7 is an example of quantification of mutant KRAS2 (GAT) in juice sample PJ7. Amplification curves from serially diluted mutant DNA mixtures and the juice DNA are shown in FIG. 7A. Based on the standard curve (FIG. 7B) from Ct values of amplification curves shown in FIG. 7A, it was estimated that PJ70 contained about 9 pg/µl GAT KRAS2, and wild-type DNA concentration for PJ70 was 900 pg/µl (data not shown). Thus, the relative amount of GAT KRAS2 DNA was approximately 1%.

Figure 8:
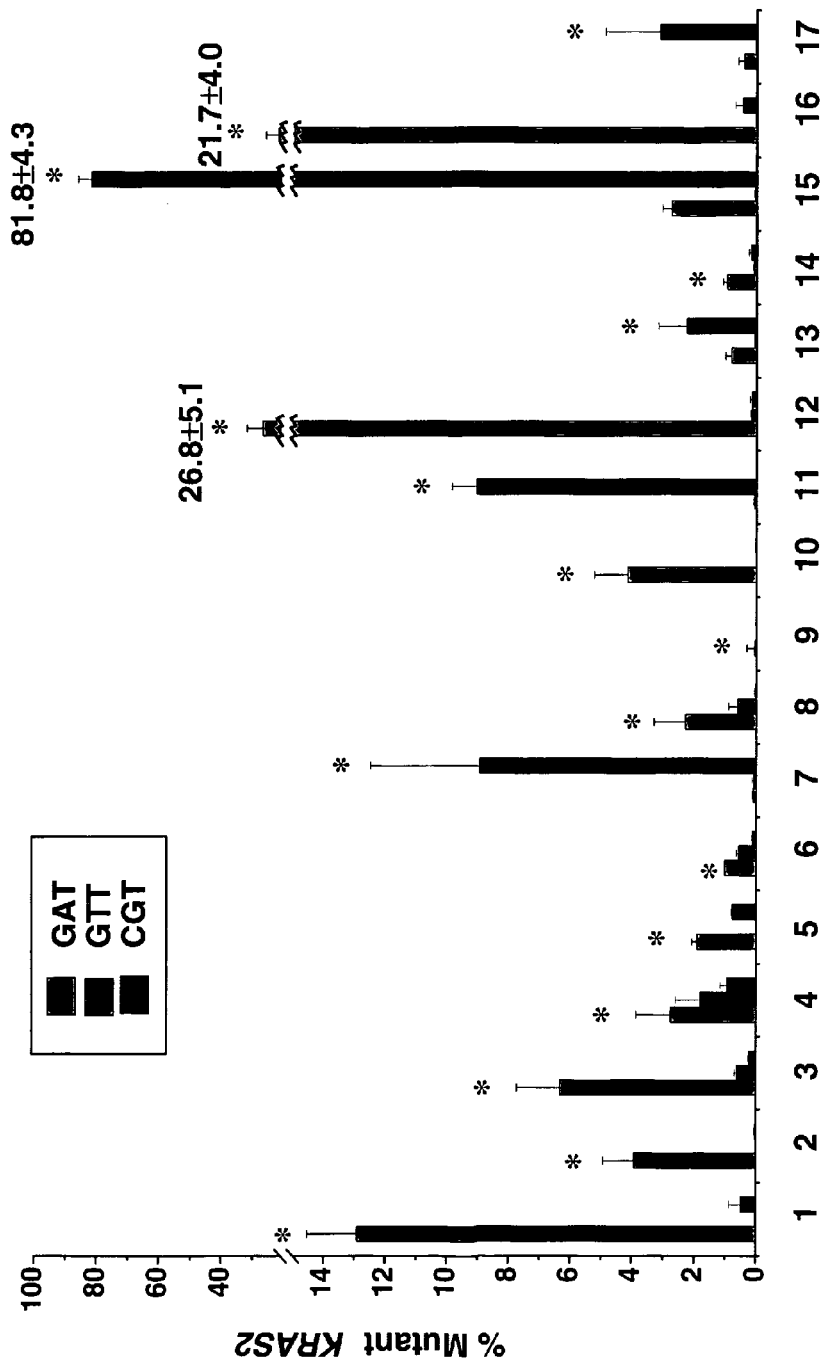
FIG. 8 depicts the percentage of mutant KRAS2 relative to wild-type KRAS2 detected in pancreatic juice from pancreatic cancer patients with known KRAS2 mutations in cancers. % mutant KRAS2=mutant KRAS2/(mutant KRAS2+wild-type KRAS2). LigAmp analysis of GAT, GTT and CGT KRAS2 mutations was shown as red, green and blue bars, respectively. Asterisk indicates the specific KRAS2 mutation detected in corresponding cancers. The percentages of KRAS2 mutations in three samples having the highest levels are shown above their corresponding bars. N=3-5 ligAmp experiments.

We first analyzed KRAS2 mutations in pancreatic juice samples from 17 pancreatic cancer patients with mutant GAT, GTT and CGT KRAS2 in their primary cancers. With ligation oligonucleotides specific for these mutations, multiple KRAS2 mutations were detected in the juice collected from most of these patients (FIG. 8). Presence of multiple KRAS2 mutations in these samples could reflect either intra-tumor clonal heterogeneity of KRAS2 mutations [Laghi, 2002 #33], or the presence of high grade PanINs that contributed mutant DNA to the pancreatic duct juice. In three of these samples, it was further confirmed their existence by T-A cloning restrict digestion enzyme-refractory PCR products and DNA sequencing. For example, in PJ70, LigAmp detected all these mutations. The GAT mutation in PJ70 was dominant, which corresponded its primary cancer. To independently document the presence of two additional minor mutations (GTT, 0.57% and CGT, 0.12%) in this sample, the amplified juice KRAS2 was sequentially digested with BstNI and BccI to eliminate both wild-type KRAS and major mutant KRAS2 (GAT), respectively. The BstNI and BccI-refractory PCR product was then cloned into T-A cloning vector and sequenced. DNA sequences from these clones confirmed the presence of GTT and CGT mutations in PJ70 (data not shown). In PJ89, dominant mutant KRAS2 is GTT. It was also detected one minor mutation (GAT, 0.1%) in this sample, which was further confirmed by cloning and sequencing of the BstNI and hpyCHIII refractory PCR product.

FIG. 8 shows LigAmp quantification of mutant KRAS2 including GAT, GTT, and CGT in pancreatic juice from pancreatic cancer patients with mutant KRAS2 sequences in their primary cancers. Consistent with KRAS2 mutation pattern in the primary cancers, GAT mutant KRAS2 was the most frequent mutation detected in the pancreatic juice. In each case, the dominant KRAS2 mutation detected in juice sample was consistent with that in primary cancer. In these duct juice samples, the amount of mutant KRAS2 DNA relative to the wild-type KRAS2 varied considerably, ranging from less than 1% to more then 80% (median 3.4%). More than 0.5% KRAS2 mutant DNA was detect in all but one juice sample (94.1%). In that case (FIG. 8, case 9), DNA sequencing identified a GAT mutation in its corresponding primary cancer tissue. However, LigAmp only detected only 0.05% GAT KRAS2 in the juice, and the CGT mutation was also present, but at an even lower level.

Pancreatic Duct Juice Analysis from Wild-Type KRAS2 Cancers and Chronic Pancreatitis.

Figure 9:
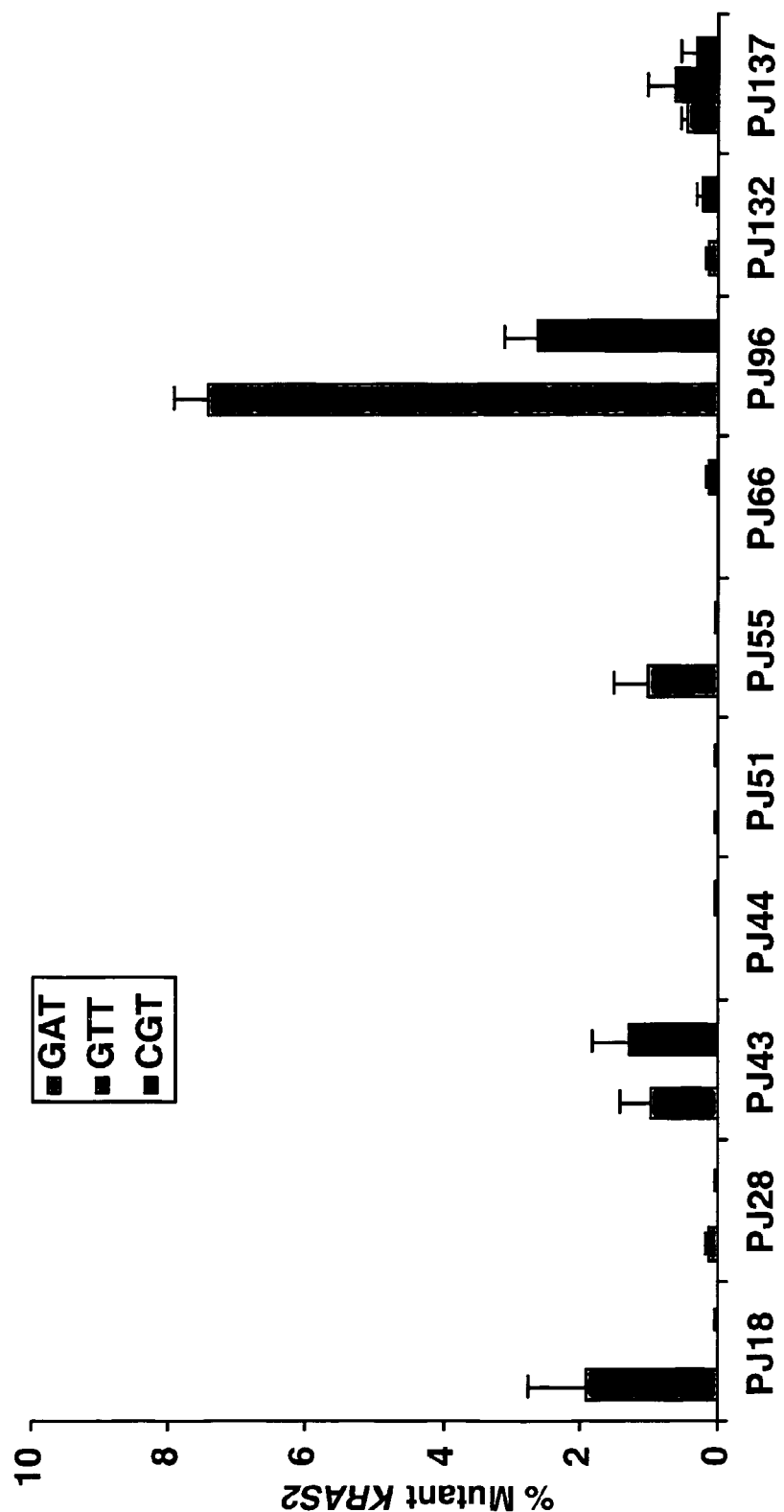
FIG. 9 depicts the percentage of mutant KRAS2 relative to wild-type KRAS2 detected in pancreatic juice from pancreatic cancer patients with wild-type KRAS2 detect in primary cancers. LigAmp analysis of GAT, GTT and CGT KRAS2 mutations was shown as red, green and blue bars, respectively. N=3-5 ligAmp experiments.

In addition, it was determined KRAS2 mutations in pancreatic juice from 10 pancreatic cancer patients whose cancers showed only wild-type KRAS2 sequence. LigAmp analysis demonstrates that 5 of these samples contained more than 0.5% mutant KRAS2 (FIG. 9). The inconsistency in KRAS2 status between primary cancers and their corresponding juice is probably caused by inability to identify KRAS2 mutation in the primary cancers because of intra-tumor clonal heterogeneity or high-grade PanIns. Sequencing of BstN1 digested PCR products also failed to demonstrate these mutations, so it is believed that this result is not due to insensitivity of DNA sequencing. When this data is combined with the mutation positive cancers, a total of 27 juice samples were analyzed and 21 cases (78%) contain more than 0.5% mutant KRAS2 in their juice samples.

Figure 10:
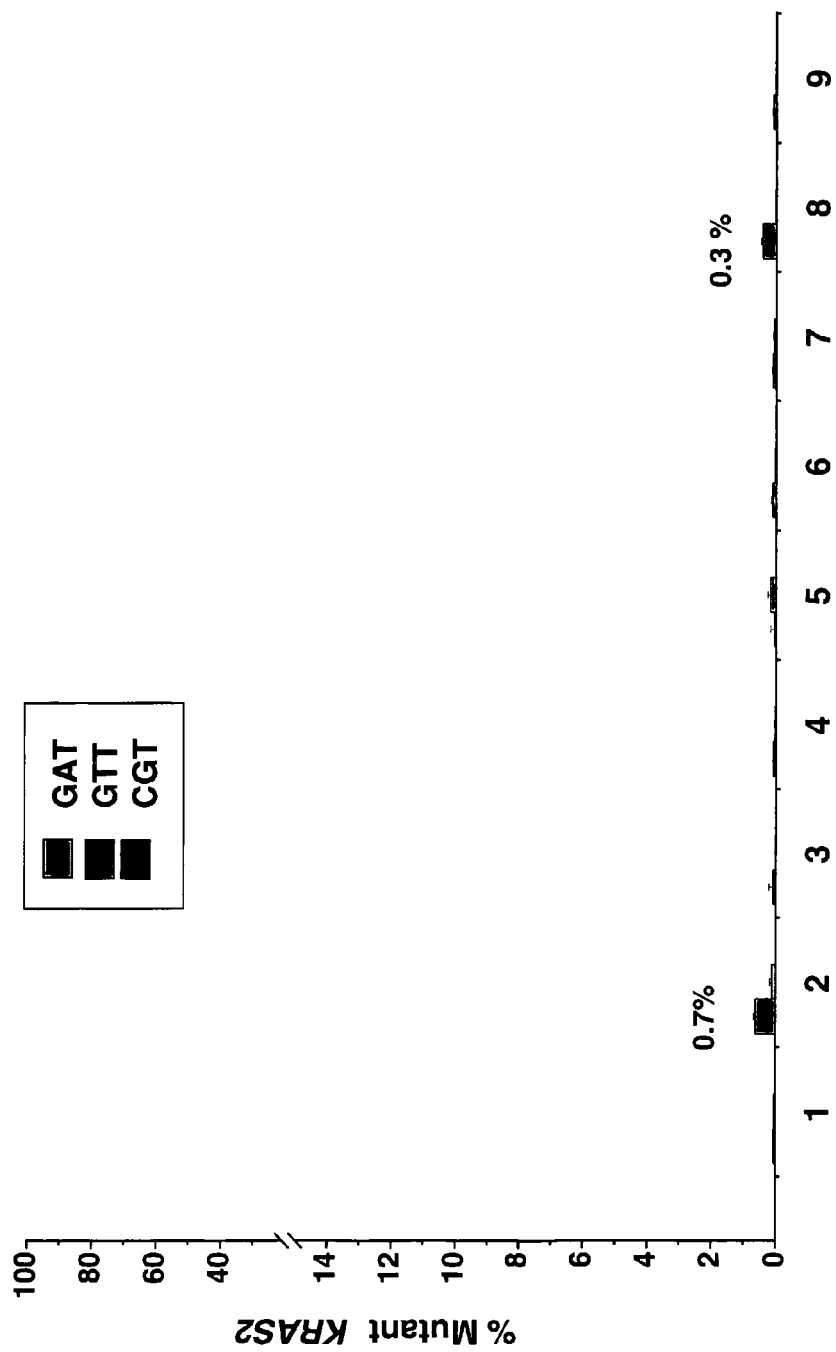
FIG. 10 depicts the percentage of mutant KRAS2 relative to wild-type KRAS2 detected in pancreatic juice from chronic pancreatitis patients. LigAmp analysis of GAT, GTT and CGT KRAS2 mutations was shown as red, green and blue bars, respectively. The percentages of KRAS2 mutations in two samples having the highest levels are shown above in the corresponding bar. N=3-5 ligAmp experiments.

KRAS2 mutations in the juice from 9 chronic pancreatitis patients were also analyzed using LigAmp. Histological examination of surgical specimens demonstrated chronic inflammation with PanINs I to II in the pancreas of most patients. As expected, LigAmp analysis detected KRAS2 mutations in the juice from these patients, but at much lower levels compared to that from pancreatic cancer patients (FIG. 10). The highest mutant KRAS2 relative to wild-type KRAS2 was 0.7%. The median level of mutant KRAS2 was 0.03. The majority of juice samples contained less than 0.1% mutant KRAS2. Only 1 out of 9 cases (12.2%) had more than 0.5% mutant KRAS2. In addition, multiple KRAS2 mutations were also observed in some samples.

Receiver Operatic Characteristic (ROC) Curve Analysis.

Figure 11:
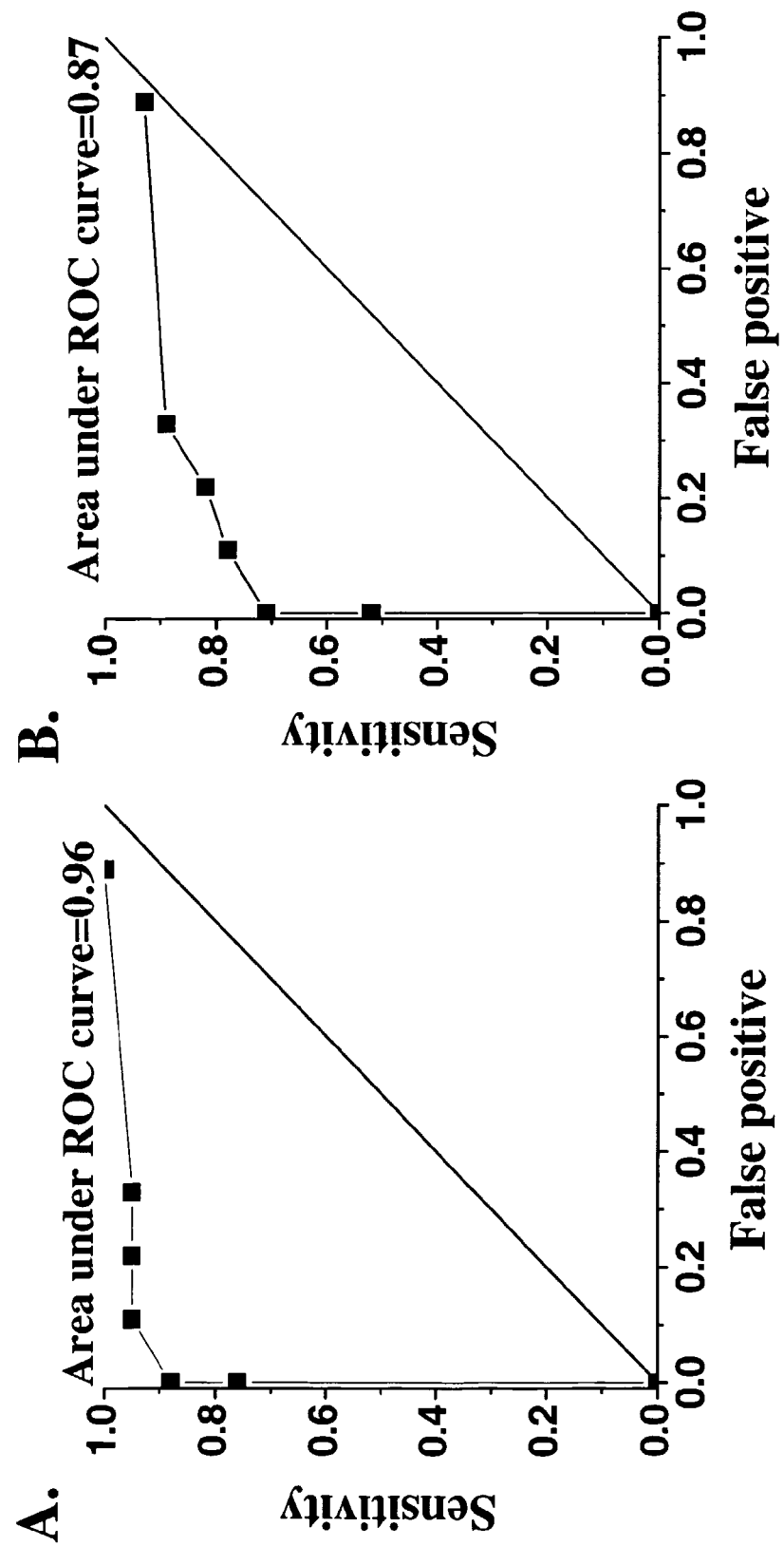
FIG. 11 depicts ROC curve analyses of LigAmp assay for early detection of pancreatic cancer by quantification of KRAS2 mutations in pancreatic juice. The sensitivities were obtained from LigAmp analysis of KRAS2 mutation in pancreatic duct juice of pancreatic cancer patients (shown in FIGS. 8 & 9) using different cutoff values. The specificities were obtained from LigAmp analysis of KRAS2 mutations in pancreatic duct juice of chronic pancreatitis patients (shown in FIG. 10) using the same set of cutoff values. False positive=1-specificity. A. A ROC curve for the subset of pancreatic cancers with KRAS2 mutations. B. A ROC curve for all cancers with or without KRAS2 mutations.

ROC curves were used to evaluate the potential use of LigAmp detection of KRAS2 mutations as a tool for the early detection of pancreatic cancer. Using different cutoff threshold values, sensitivity and specificity of the assay were calculated based on the data from pancreatic cancer and chronic pancreatitis patients, respectively. For example, when 0.5% of mutant KRAS2 is used as a cutoff value for diagnosis of pancreatic cancer, LigAmp analysis for KRAS2 mutations in pancreatic juice has a sensitivity of 94% (16 of 17 cases positive), a specificity of 89% (8 out of 9 pancreatitis cases negative). Using a threshold of 0.5%, the KRAS2 mutation frequency in pancreatic cancer was significantly higher than that in chronic pancreatitis ($P<0.001$, chi-squared). Based on sensitivities and specificities at different cutoff thresholds, a ROC curve was constructed for the subset with mutant KRAS2 pancreatic cancer shown in FIG. 8. The area under the ROC curve is 0.96 (FIG. 11A), where a perfect test has an area under the curve of 1.0. When a ROC curve was constructed for all the cancers, irrespective of their KRAS2 mutation status, an area of 0.87 was obtained (FIG. 11B).

KRAS2 mutations were analyzed in the pancreatic duct juice from 27 pancreatic cancer and 9 chronic pancreatitis patients. Multiple KRAS2 mutations in the juice from these patients were detected. In the subset of pancreatic cancers with KRAS2 mutations, the dominant KRAS2 mutation detected in the juice corresponded to that present in primary cancers, as expected. It was also found that the pancreatic juice from cancer patients contained high levels of mutant KRAS2 compared to that from chronic pancreatitis patients. This most likely reflects high grade PanIns that are the precursor lesion for pancreatic cancer [Takaori, 2004 #36]. In about 94% of cancer patients with mutant KRAS2 in their primary cancers, >0.5% KRAS2 mutations in their juice samples were detected, while only 11% juice samples from patients with chronic pancreatitis contained >0.5% KRAS2 mutations. At a 1% cutoff the sensitivity is 88% and specificity is 100%, while at a 2% cutoff, the sensitivity is 76% and the specificity is 100%. ROC curve analysis demonstrated that LigAmp quantitative analysis of KRAS2 mutation in pancreatic juice was an excellent assay for detection of pancreatic cancer.

While analyzing KRAS2 status in primary cancers, in only 17 of 27 cases harbored mutant KRAS2 by DNA sequencing. This could be due to the known relatively poor limit of detection of DNA sequencing (estimated at 10-20%), possibly in combination with low neoplastic cellurity in these specimens [Logsdon, 2003 #34][Crnogorac-Jurcevic, 2002 #35]. In this regard, pancreatic adenocarcinomas are generally rich in wild-type KRAS2 containing stroma and inflammatory cells. Laser capture microdisection can be used to eliminate the influence of the stroma [Crnogorac-Jurcevic, 2002 #35], hereby increasing the sensitivity of KRAS2 sequencing. The result (FIG. 9) shows the presence of KRAS2 mutations in juice from some patients with wild-type KRAS2 sequence in their primary cancers. This suggests that the direct DNA sequencing of cancers in the current study may have underestimated the frequency of KRAS2 mutations. If those with high-level mutant KRAS2 (>0.5%) in juice to be were considered KRAS2 mutant cancers and those with very low or even undetectable mutant DNA in juice to be wild-type KRAS2 cancers, then the prevalence of KRAS2 mutations is about 82.5% in this population of pancreatic cancers.

Mutation in KRAS2 is an early event in pancreatic cancer development [Takaori, 2004 #36][Hruban, 2000 #12]. Mutations have been detected in very small incidental carcinomas that were only found at autopsy. KRAS2 could be a molecular marker for detecting pancreatic cancer at an early stage, however KRAS2 mutations are also qualitatively present in hyperplastic ductal changes in pancreas with chronic pancreatitis [Hruban, 2000 #12]. In addition, mutant KRAS2 was detected in pancreatic and duodenal juice from patients with chronic pancreatitis [Maire, 2002 #15][van Laethem, 1999 #18][Queneau, 2001 #37]. This makes it difficult to believe that simple qualitative detection of mutant KRAS2 could be a reliable tool for early diagnosis of pancreatic cancer. However, during cancer progression, cancer cell proliferation and invasion as well as luminal necrosis could result in accumulation of cancer DNA in the pancreatic duct juice, which may lead to a larger amount of mutant KRAS2 present in the juice in cancer patients than that in pancreatitis patients. Indeed, it is confirmed by our current result demonstrating that much higher levels of KRAS2 mutations were present in the juice in pancreatic cancer patients. The relative amounts of mutant KRAS2 reached up to more than 80% in the cancer patients, whereas in chronic pancreatitis, the highest level of mutant DNA in juice was only 0.7%. Therefore, in this limited study, quantification of mutant KRAS2 in juice can largely distinguish pancreatic cancer from chronic pancreatitis.

It was also demonstrated that multiple KRAS2 mutations existed in juice from some pancreatic cancer patients. Interesting, some samples showed only the mutation that was present in the corresponding cancer (e.g. samples 2 and 10, FIG. 8), while others showed much more comparable levels of the all of the different KRAS2 mutations (e.g. sample 4, FIG. 8). The precursor lesion, PanIN, often coexists with neoplastic pancreas [Laghi, 2002 #33] [Luttges, 1999 #31]. Up to 75% of these lesions also carry KRAS2 mutations, which can be shed into the pancreatic duct juice. The specific KRAS2 mutations in these lesions may be different from that in primary cancers, which may explain why multiple KRAS2 mutations are detected in pancreatic duct juice. In addition, distinct KRAS2 mutations were found to coexist in microareas of a single tumor, suggesting genetic heterogeneity within the tumor sub-populations [Laghi, 2002 #33].

Chronic pancreatitis is an independent risk factor for the development of pancreatic cancer. The incidences of pancreatic cancer 10 and 20 years after diagnosis of chronic pancreatitis are 1.8% and 4.0%, respectively [Lowenfels, 1993 #27]. Screening for malignancy in chronic pancreatitis patients is a great challenge. However, several studies have identified subsets of chronic pancreatitis patients with an even greater increased risk for pancreatic cancer, which might provide some useful information for screening. Of chronic pancreatitis, those caused by alcohol consumption are weakly related to pancreatic cancer, whereas these with KRAS2 mutation carry an increased risk for pancreatic cancer [van Laethem, 1999 #18][Berthelemy, 1995 #28][Arvanitakis, 2004 #29]. Hereditary pancreatitis, an autosomal dominant disease, is highly associated with pancreatic cancer, especially for patients who smoke [Lowenfels, 2001 #26][Meckler, 2001]. Using a sensitive and specific assay to screen these patients will be of benefit for early detection of pancreatic cancer. Based the present result showing much higher levels of KRAS2 mutations in the juice from pancreatic cancer patients than that from chronic pancreatitis patients, it is reasonable to suggest that LigAmp quantitative analysis of KRAS2 mutations might predict and/or detect development of malignant lesions from these benign conditions by dynamically monitoring KRAS2 mutation levels in the pancreatic juice.

Quantification of KRAS2 mutations in pancreatic juice using LigAmp is able to differentiate pancreatic cancer from chronic pancreatitis in this limited study. LigAmp may be a useful tool for early detection of pancreatic cancer. Periodic endoscopy with pancreatic duct juice collection may be justified in especially high risk individuals such as those with a strong family history or chronic pancreatitis. General population screening will require detection in a less invasive sample such as peripheral blood.

Example 3

Bile Duct Cancer Early Detection-Bile and Serum Analysis

LigAmp of KRAS2 mutation on bile and serum collected from patients with biliary cancer. Many patients with biliary tract carcinoma were diagnosed at an advanced stage, resulting a poor prognosis. Early detection of biliary cancer might improve the survival rate. Analysis of cancer-related genes present in bile or serum may provide a tool for early diagnosis. The genetic alterations such KRAS2 and p53 mutations were observed in sporadic biliary tract cancer.

Figure 12:
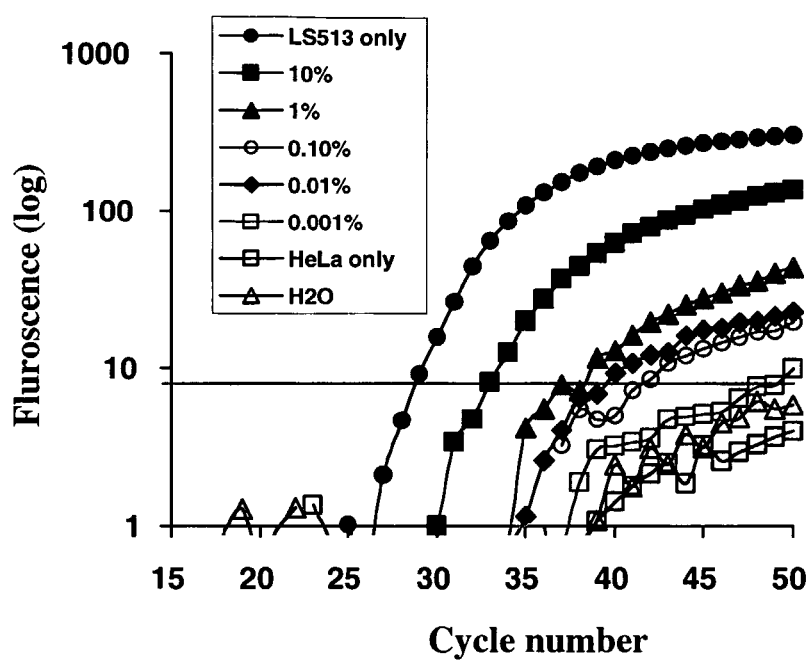
FIG. 12 depicts the results of the LigAmp assay on genomic DNA extracted from cell mixtures. LigAmp is able to detect one mutant molecule in the present of 10,000 wild-type DNA copies using DNA mixtures. The sensitivity of LigAmp using genomic DNA isolated from previously made mixtures of mutant and wild-type cells was determined. KRAS2 mutant LS513 cells were serially diluted into wild-type HeLa cells. Genomic DNA was then isolated from the mixes. The percentage of the mutant cells in the cell mixtures ranged from 100% to 0.001%. One microgram of genomic DNA extracted from each cell mixture was used for LigAmp. As shown in the Figure, using DNA isolated from cell mixture, the assay is able to detect one mutant cell in the presence of 10,000 to 100,000 normal cells.
Figure 13:
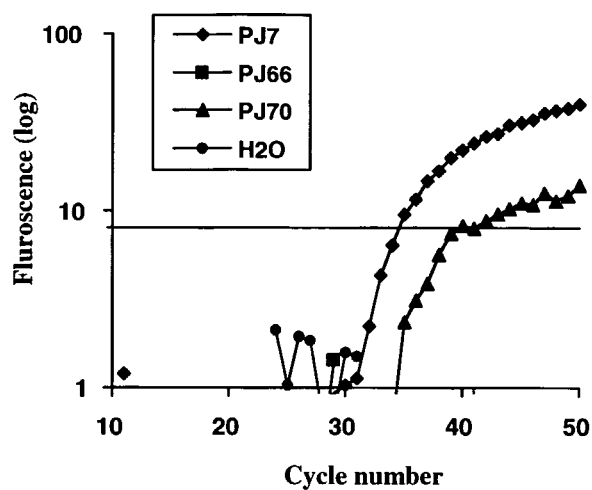
FIG. 13 depicts the results of LigAmp on whole genome amplified (WGA) DNA. Clinical samples such as serum, plasma and other body fluids often contain only small amounts of DNA, which makes it difficult to detect mutant DNA directly using DNA isolated from these samples. Moreover, PCR amplification is commonly used to exponentially produce many copies of a DNA target sequence, but restricts one to a single gene or at most a handful of genes of interest. PCR based whole genome amplification is notoriously biased (unbiased amplification of different genes is difficult to obtain). LigAmp was performed on whole genome amplified DNA. One nanogram of DNA from pancreatic cancer patient's pancreas juice samples PJ7 (GAT), PJ66 (GGT) and PJ70 (GAT) were subjected to whole genomic amplification. Two hundred nanograms of amplified products were then used as template for LigAmp detection of GAT mutant. Data shows that LigAmp was capable of detecting the KRAS2 mutation in whole genomic amplified DNA in PJ7 and PJ70.
Figure 14:
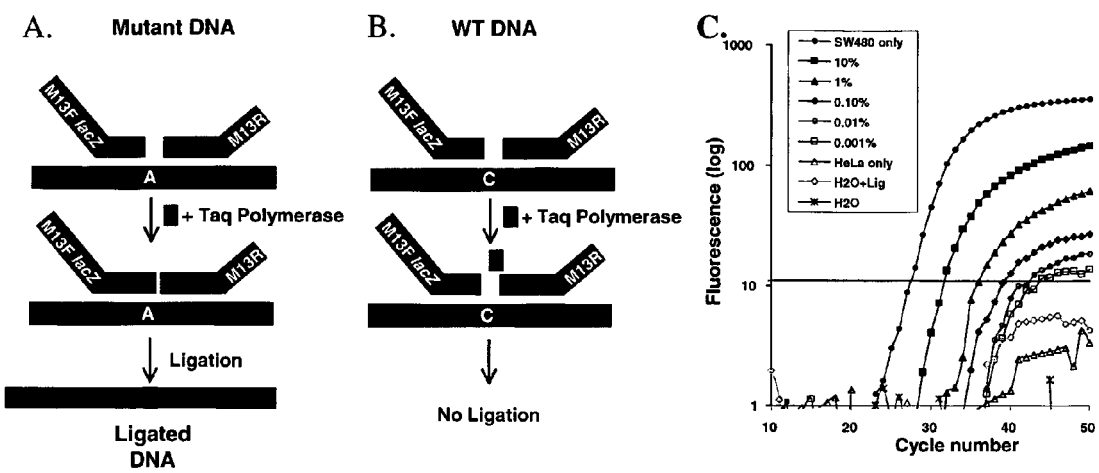
FIG. 14 graphically depicts the GAP LigAmp assay and depicts results of GAP LigAmp. LigAmp assay is a very sensitive point mutation detection strategy, able to detect one mutant DNA molecule in the presence of 10,000 wild-type copies. However, in initial work, the amplification signal derived from 1:100,000 DNA mixtures overlapped with that from wild-type DNA only. The specificity of the assay is mainly determined by fidelity of the DNA ligase used in ligation step. Although a thermostable DNA Ligase (pfu DNA ligase) was used to enhance the specificity, misligation still occurs.

DNA isolated from cancer tissues, bile and serum were first subjected to PCR amplification. Five hundred picogram PCR DNA was used as template for LigAmp. LigAmp on DNA from the biliary cancer tissues demonstrated that majority of cancer (more than 90%) harbored GAT mutation. Mutation of KRAS2 (GAT) was detected in 81% (13/16) of bile from patient with biliary cancer, while 21% (6/28) of bile from control group. These six control patients with KRAS2 mutation carried diseases associated with chronic inflammation. In the serum DNA from biliary cancer patients, 54.5% (6/11) were detected to contain KRAS2 (GAT) mutant DNA. These data shows that LigAmp on bile and serum can be used an early diagnosis tool. See FIG. 12.

Example 4

Sensitive and accurate detection of small number of tumor cells in the presence of a vast excess of normal cells is a problem common to many cancer research and clinical applications, but it is difficult since the mutant DNA often differs from the wildtype DNA by only a single base. The aim of present study is to develop a novel strategy that converts a single base substitution to a distinct molecule so that it can be detected in a sensitive and linear fashion. This strategy (designated LigAmp) employs two unique oligonucleotides that contain regions specific to the target gene and M13 tails. In addition, the upstream oligonucleotide also contains a region of completely foreign DNA. These two oligonucleotides should be ligated at the mutation site only when a perfectly matched target is present. Ligated products are then amplified by real-time quantitative PCR using M13 primers and the foreign DNA region as a probe. To test this strategy, K-ras mutant SW480 genomic DNA was 10 fold serially diluted into wildtype K-ras Hela DNA. It was demonstrated that the ability to detect one mutant DNA molecule in the presence of a background of 10,000-100,000 wildtype molecules. See FIGS. 12-19 and 30.

Example 5

Sensitive detection of small number of tumor cells in a vast excess of normal cells is a problem common to many cancer research and potential clinical applications. The mutant DNA often differs from the wild-type DNA by only a single base. A novel strategy was developed that converts a single base substitution into a completely foreign molecule. This strategy (LigAmp) employs two unique oligonucleotides that contain regions specific to the target gene and M13 tails. In addition, the upstream oligonucleotide contains a region of completely foreign DNA. These two oligonucleotides should be ligated at the mutation site only when a perfectly matched target is present. After conversion, ligated products are amplified by real-time quantitative PCR using M13 primers and a probe to the foreign DNA region on a Cepheid SmartCycler. To test this strategy, KRAS2 mutant genomic DNA was 10-fold serially diluted into wildtype DNA. The ability to detect one mutant DNA molecule in the presence of a background of 10,000 wild-type molecules was demonstrated. LigAmp can be multiplexed, detecting different mutations, or both mutant and wild-type DNA, simultaneously. In a model of early detection, KRAS2 mutations were detected in pancreatic duct juice from patients with pancreatic cancer. The relative amounts of KRAS2 mutant to wild-type DNA were obtained by absolute quantification. LigAmp permits sensitive and linear detection of point mutation containing DNA. See FIGS. 12-19 and 30.

Example 6

Biliary cancer is a lethal disease, and early detection efforts are needed to ameliorate the dismal prognosis. Mutations of the KRAS gene, specifically at codon 12, are one of the most common genetic aberrations in this cancer. An ultra-sensitive technology LigAmp—has been described (Shi et al, Nature Methods, 2004) for the detection of single base pair mutations in clinical samples. LigAmp has a sensitivity of detecting a mutant population with a sensitivity of 1:10,000 wild-type cells. LigAmp was utilized to detect KRASG12D mutations in patients with a variety of neoplastic and non-neoplastic biliary diseases. In LigAmp, a mutation specific 5 oligonucleotide and a generic 3 oligonucleotide (both tagged with M13 tails) are ligated using Pfu ligase, followed by amplification using M13 primers. The 5 oligonucleotide also has an upstream unrelated bacterial gene sequence (e.g., lacZ), and a specific flurophor-labeled probe to the latter can be utilized to generate cycle threshold (Ct) values for the mutant DNA of interest in the sample. Serially diluted positive control and negative control cell lines in each run provide relative quantification of mutant KRAS levels. Oligonucleotides specific to the KRASG12D mutation were designed. DNA was extracted from 119 samples, including 10 biliary cancer xenografts, 54 archival biliary cancers, 44 bile samples, and 11 serum samples. Of the 44 bile samples, 16 were from patients with biliary cancers, and 28 from a variety of non-neoplastic pancreato-biliary disorders; all 11 serum samples were from patients with biliary cancer.

KRASG12D mutations were detected in 10/10 (100%) biliary xenografts and 52/54 (96%) archival cancers. 13/16 (81%) neoplastic bile samples and only 6/28 (21%) non-neoplastic bile samples harbored mutant KRAS DNA (P=0.0003); the latter included chronic pancreatitis and primary sclerosing cholangitis, both conditions where this mutation has been reported. KRASG12D mutations were also detected in 6/11 (55%) serum samples from biliary cancer patients.

KRASG12D mutations are present in the majority of biliary cancers, and are detectable in bile and serum using LigAmp. This technology has the potential for early detection of biliary cancer as well as for disease monitoring post-therapy. See FIG. 14.

Example 7

LigAmp analysis of GAT KRAS2 mutations in biliary tract cancers is shown in FIG. 20. A. Representative amplification curves for mutant DNA mixtures and three cancer samples (blue lines). Mutant DNA mixtures were made by serial dilution of mutant GAT KRAS2 into the wild type DNA. B. Amplification curves for primary tumors including 23 intra-hepatic and extrahepatic cholangiocarcimas (blue lines) and 31 gallbladder carcinomas (red lines). PCR amplified DNA (600 pg) was used for LigAmp. One sample from a gallbladder cancer patient overlapped with the wild type signal. No amplification curves were obtained from three additional gallbladder cancer patient samples.

LigAmp analysis of GAT KRAS2 mutations in bile from biliary tract cancer patients (n=16) is shown in FIG. 21. Amplification curves were obtained in 13 of 16 bile samples.

Detection of the GAT KRAS2 mutation in serum from biliary tract cancer patients is shown in FIG. 22. A. The relative amount of the mutant to wild-type KRAS2 DNA in serum detected by LigAmp. Error bars are 1 standard deviation from 3 independent LigAmp assays. B. DNA sequence of the cloned BstN1 refractory PCR product from sample 166, confirming the existence of a low level GAT mutation.

Table 3 summarizes the frequency of KRAS2 mutations in biliary tract primary tumors. This data demonstrates the usefulness of the methods of the invention to detect the cancers in bile and in serum.

TABLE 3

Frequency of KRAS2 mutations in biliary tract cancer (primary tumors)

|  | KRAS2 WT | KRAS2 Mutant | Total | % KRAS2 mutant |
|---|---|---|---|---|
| Biliary Cancer Xenograft | 0 | 10 | 10 | 100.0 |
| Cholangiocarcinoma | 0 | 23 | 23 | 100.0 |
| Gall bladder Cancer | 4 | 27 | 31 | 87.1 |
| Total | 4 | 60 | 64 | 94 |

Table 4 summarizes the Chi-square analysis of KRAS 2 mutations in bile.

TABLE 4

Chi-square analysis of KRAS2 mutation in bile

|  | KRAS2 mutation | | |
|---|---|---|---|
| Diseases | + | − | Total |
| Biliary cancer | 13 | 3 | 16 |
| Benign disease | 6 | 22 | 28 |
| Total | 19 | 25 | 44 | p < 0.001

Example 8

Informed consent was obtained from all subjects. Guidelines of the US Dept. of Health and Human Services and the authors' institutions were followed in the conduct of this research. Women were antiretroviral drug naive and did not receive any other antiretroviral therapy, consistent with the standard of care in Uganda at the time the trial was performed. Samples were analyzed from nine women and five infants who had long-term follow-up samples available for analysis. Those study subjects were selected for follow-up in a previous study, after they were found to have NVPR in samples collected 6-8 weeks after delivery (Eshleman S H, Mracna M, Guay L A, et al. Selection and fading of resistance mutations in women and infants receiving nevirapine to prevent HIV-1 vertical transmission (HIVNET 012). AIDS 2001; 15:1951-1957). Samples collected prior to NVP dosing from 40 additional women in HIVNET 012 were also analyzed.

HIV Genotyping and HIV Subtyping

HIV-1 genotyping was performed with the ViroSeq HIV-1 Genotyping System and HIV-1 subtyping was performed by phylogenetic analysis of pol region sequences (Eshleman S H, Guay L A, Mwatha A, et al. Characterization of nevirapine (NVP) resistance mutations in women with subtype A vs. D HIV-1 6-8 weeks after single dose NVP (HIVNET 012). J Acquir Immune Defic Syndr 2004; 35:126-130). Some samples were genotyped in previous studies (Eshleman S H, Mracna M, Guay L A, et al. Selection and fading of resistance mutations in women and infants receiving nevirapine to prevent HIV-1 vertical transmission (HIVNET 012). AIDS 2001; 15:1951-1957 and Eshleman S H, Guay L A, Mwatha A, et al. Comparison of nevirapine (NVP) resistance in Ugandan women 7 days vs. 6-8 weeks after single dose NVP prophylaxis: HIVNET 012. AIDS Res Hum Retroviruses 2004; 20:595-599).

Detection of the K103N Mutation Using the LigAmp Assay

The LigAmp assay involves mutation-specific ligation of two oligonucleotides to a DNA template, followed by real-time PCR detection of the ligated product (Shi C, Eshleman S H, Jones D, et al. LigAmp: Sensitive detection of single nucleotide differences. Nature Methods 2004; 1:141-147). LigAmp was optimized for detection of K103N in subtypes A and D (FIGS. 23 and 24). The conditions used for analysis are described on-line (web site to be listed here). The limit of detection for K103N in both subtypes was 0.08% (mean result obtained for wild type DNA+3 SD). An assay cut-off was set at 0.1% mutant. For analysis of plasma samples, PCR products generated with ViroSeq were used as template DNA and analyzed in triplicate. To permit analysis of the same samples with the TyHRT assay, PCR products were generated without dUTP. A standard curve was included in each experiment and was used to quantify the % K103N in each sample (FIGS. 24c and 24d).

Detection of NVPR Mutations Using the Yeast TyHRT Assay

The TyHRT assay was used to screen libraries of HIV-1 RT-containing clones for RT activity and NVP susceptibility (Curcio M J, Garfinkel D J. Single-step selection for Ty1 element retrotransposition. Proc Natl Acad Sci USA 1991; 88:936-40 and Nissley D V, Boyer P L, Garfinkel D J, Hughes S H and Strathern J N. Hybrid Ty1/HIV-1 elements used to detect inhibitors and monitor the activity of HIV-1 reverse transcriptase. Proc Natl Acad Sci USA 1998; 95:13905-10). Plasmids from NVP-resistant clones were sequenced to identify NVPR mutations. A general description of the assay and the conditions used for analysis are provided on-line (web site to be listed here).

Detection of NVPR Mutations Using the ViroSeq Assay

Plasma samples were analyzed using a population sequencing-based assay (ViroSeq, FIGS. 25a and 26a). The women and infants selected for this study all had NVPR mutations detected 6-8 weeks after NVP administration.

Samples collected from women prior to NVP and at delivery were wild type (no NVPR mutations detected, FIG. 25a).

Genotyping results were obtained for five women 7 days (1 week) after NVP. None of the women had K103N. Two women had other NVPR mutations (one had Y181C, one had Y181C+G190A). At the 6-8 week visit, 8/9 women had K103N and 4/9 had other NVPR mutations (three had K103N+Y181C, one had V108I). Samples collected 12-24 months after NVP from all nine women were wild type.

Samples collected at birth from all five infants were wild type (FIG. 26a). At 6-8 weeks, 2/5 infants had K103N and 4/5 had other NVPR mutations (two had Y181C, one had K103N+Y181C, one had Y181C+Y188C). Samples collected 14-16 weeks after NVP were available for 4/5 infants. One infant had K103N and one had Y181C. K103N was not detected in the infants at one year of age. G190A was detected in one infant at 12 months of age, but was not detected in samples collected from that infant at earlier study visits.

Detection and Quantification of the K103N Mutation Using the LigAmp Assay

The LigAmp assay was used to detect and quantify HIV-1 K103N-containing variants (FIGS. 25b and 26b). The K103N mutation was selected for analysis, since K103N was the most common NVPR mutation detected by ViroSeq in women in HIVNET 012 6-8 weeks after NVP exposure and in a South African cohort 6 months after NVP exposure.

Samples from all nine women collected prior to NVP exposure and at delivery had levels of K103N below the assay cutoff (<0.1%; FIG. 25b). Samples from 40 other women in HIVNET 012 were also analyzed. The % K103N was below the assay cutoff in 36 (90%) of the 40 samples. In the remaining four samples, K103N was detected at 0.11%, 0.12%, 0.21%, and 0.31% (not shown). In 8/9 women selected for follow-up, selection K103N was detected at the 6-8 week visit. The mean % K103N among the eight women was 13.9%. In six women, K103N faded below 0.1% by 12-24 months after delivery. However, in three women, K103N was detected above 0.1% 14 months after NVP dosing (at 0.8%, 1.3%, 3.5%, FIG. 25b, arrows).

The % K103N was below the assay cutoff in 4/5 infants at birth (FIG. 26b). In one infant, K103N was detected at a level just above 0.1%. At 6-8 weeks, K103N was detected above 0.1% in 4/5 infants, and the % K103N remained elevated in one infant at 14-16 weeks of age (I-545). In that infant, K103N was still detected a year after SD NVP exposure (at 1.5%, FIG. 26b, arrow).

Comparison of Results from the LigAmp and TyHRT Assays

The samples described above were also analyzed using the yeast-based TyHRT assay to confirm persistence of the K103N mutation in the long-term follow-up samples (FIGS. 25c and 26c). The TyHRT assay is a genetic assay that allows one to screen libraries of HIV-1 RT-containing clones for RT activity and NVP susceptibility.

Results from the LigAmp assay (% K103N) and the TyHRT assay (% NVPR) were consistent. Seventeen of 20 samples that had K103N detected in the LigAmp assay, also had NVPR detected in the TyHRT assay, and K103N was detected among the NVPR clones. In the three remaining samples, the % K103N detected in the LigAmp assay was <1%. Failure to detect NVPR in those samples in the TyHRT assay may reflect the lower sensitivity of that assay for mutation detection (approximately 0.5% mutant). A few samples that did not have K103N detected in the LigAmp assay demonstrated NVPR in the TyHRT assay. In those samples, clones isolated in the TyHRT assay did not have K103N with the following exception of rare clones from one mother-infant pair (1/210 clones from the pre-NVP sample from M-750 and 1/190 clones from the 14-week sample from I-750). In both cases, K103N was encoded by AAT, which was not probed in the LigAmp assay. K103N was detected in four long-term follow-up samples in the LigAmp assay (at 0.8%, 1.3%, 3.5% and 1.5% (M-474, M-750, M-830 and I-545 respectively, FIGS. 25b and 26b, arrows). The % NVPR detected in the TyHRT assay for those samples was 3.4%, 0.6%, 11%, and 0.3%, respectively. Even though relatively few NVP-resistant clones were isolated from those samples, K103N was detected in all four samples. In contrast, long-term follow-up samples that did not have K103N detected in the LigAmp assay also did not have K103N detected in the TyHRT assay. Of note, the one 12-month infant sample that had G190A detected by ViroSeq also had G190A detected in the TyHRT assay. Interestingly, two samples had NVPR detected by the TyHRT assay, but did not have NVPR mutations detected among the NVP-resistant clones (the 7-day sample from M-554 and the delivery sample from M-847). In both cases, substitutions were noted at codon 236 (P236L and P236A, respectively). In subtype B, P236L is associated with resistance to delavirdine, but causes hypersusceptibility (rather than resistance) to NVP.

It was found that K103N-containing variants can persist above pre-NVP levels in some women and infants a year or more after SD NVP. This finding is consistent with studies showing that K103N confers a relatively small fitness cost in vitro [17-19], and with studies showing persistence of K103N for years in some patients who are infected with resistant strains [20]. Preliminary reports using mutation-specific real-time PCR assays also show long-term persistence of NVPR mutations in women with subtype C [21,22]. This study included only women and infants who had NVPR detected by ViroSeq 6-8 weeks after SD NVP. This approach is likely to bias the results in favor of detection of NVPR in long-term follow-up samples.

The LigAmp assay was particularly useful for quantification of K103N-containing variants in this study. The assay has a broad linear range and can quantify variants at a level of 0.1%. The assay can be performed without patient-specific primers and can be performed using PCR products remaining from routine genotyping. The assay is relatively simple to perform and uses very low concentrations of template. The TyHRT assay also offers unique advantages for analysis of HIV-1 drug resistance mutations. That assay provides phenotypic selection of drug resistant variants, which can be further characterized by DNA sequencing. That approach may be particularly useful for analysis of low-level drug-resistant variants in non-B subtypes, where the genetic correlates of antiretroviral drug resistance are not well-defined.

Further studies are needed to determine whether persistence of NVPR mutations at low levels after SD NVP compromises efficacy of NNRTI-containing regimens for HIV-1 treatment or pMTCT in subsequent pregnancies. Emergence of NVPR in women and infants receiving regimens for pMTCT can usually be prevented by providing pregnant women with potent combination antiretroviral therapy. However, in resource-poor countries with limited access to antiretroviral drugs, simpler regimens are more likely to be used for pMTCT. Some studies have evaluated NVPR in women who received SD NVP for pMTCT in combination with other antiretroviral drugs. Unfortunately, NVPR often emerges despite the addition of other drugs to the pMTCT regimen [6,8,23,24]. Further studies are needed to evaluate the clinical significance of NVPR in this setting, and the persistence of low levels of NVPR in women and infants after SD NVP exposure. Sensitive resistance assays, such as LigAmp, may be useful for evaluation of the persistence of resistant variants.

Methods for Detection of K103N in HIV-1 Subtypes A and D Using the LigAmp Assay

Ligation was performed using 100 pg of plasmid-derived or plasma-derived PCR products. DNA concentrations were determined using a NanoDrop spectrophotometer (ND-1000, NanoDrop Technologies, Wilmington, Del.). Gel-purified ligation
oligonucleotides (Table 5) were purchased from Invitrogen, Corp. (Carlsbad, Calif.). PCR products were incubated with 1 pmol of the upstream oligonucleotide, 2 pmol of the downstream oligonucleotide and 4 U Pfu DNA ligase in 1×Pfu Ligase Buffer (Stratagene, La Jolla, Calif.). Samples were denatured at 95° C. for 1 minute, followed by 99 two-step cycles alternating 95° C. for 30 seconds with 50° C. for 4 minutes. A negative control (no DNA template) was included with each set of ligation reactions, and was carried through the real-time detection step. Real-time PCR was performed using a SmartCycler (Cepheid, Sunnyvale, Calif.). Each 25 µl reaction contained 5 pmol M13 forward primer and 5 pmol M13 reverse primer (Invitrogen, Table 5), 5 µl of the unpurified ligation reaction, 12.5 µl platinum Quantitative PCR SuperMix-UDG (Invitrogen), and 5 pmol of the LacZ probe (Integrated DNA Technology, Coralville, Iowa, Table 5). Reactions were pre-incubated at 50° C. for 2 min and 95° C. for 2 min, followed by 45 two-step cycles of 95° C. for 10 seconds alternating with 64° C. for 25 seconds. The cycle threshold was manually set in the middle of the linear range of the amplification curve for each experiment (log scale).

Methods Used for Analysis of Non-Nucleoside Reverse Transcriptase (NNRTI) Resistance Mutations Using the Yeast TyHRT Assay.

In the TyHRT system, amplified HIV-1 pol region DNA from test samples is co-transformed into yeast with a plasmid containing a TyHRT element with a deletion in the RT region. HIV-1 RT DNA is introduced into the TyHRT element by homologous recombination. Each isolate carries a unique RT domain and the library of isolates is representative of the RT domains present in the original viral sample. The TyHRT elements carry the reverse transcription indicator gene, his3AI. Expression and reverse transcription of the TyHRT element by the recombed HIV-1 RT results in conversion of the his3AI gene into a functional HIS3 gene [16]. RT activity is detected as the ability to give rise to cells that are able to grow on media lacking histidine. Selection in the presence of NNRTIs measures the NNRTI susceptibility of individual RT clones. Analysis of the RT activity and NNRTI susceptibility [17] of the isolates present in large libraries makes it possible to detect NNRTI-resistant RT variants that are present at low frequency.

Reverse transcription was carried out in yeast strain DG1251 (MATa ura3-167 trp1-hisG spt3-101 his3D200). The plasmid pH☐RT1 has the BsrGI-PvuII fragment of the HIV-1 RT coding removed resulting in deletion of HIV-1 RT amino acids 37-250. BsrGI/PvuII linearized, gel-purified pH☐RT1 (100-200 ng) and HIV-1 RT domain PCR product (200-500 ng) were co-transformed into DG1251 using a lithium acetate protocol [18]. Transformants were selected on SC-URA (synthetic complete media missing uracil)+glucose plates [19]. Transformants were arrayed in small (100/plate) or large (25/plate) patches on SC-URA+glucose plates using sterile toothpicks. Following incubation overnight at 30° C. arrayed patches were replica plated with velveteen to SC-URA+galactose plates with or without inhibitor and grown 2 days at 30° C. to induce expression of the hybrid retroelements which are under the control of the GAL1 promoter [20]. The plates were then replica plated to SC-HIS (SC missing histidine)+/−inhibitor and grown for 3-4 days at 30° C. to select reverse transcription events. NVP was dissolved in dimethylsulfoxide (DMSO) and used at 80-160 ☐M at a final DMSO concentration of 1%.

For DNA sequencing, HIV-1 RT domains in TyHRT elements were obtained by growing isolates overnight in 10 ml SC-URA at 30° C. and preparing DNA with a glass bead/ phenol extraction method. DNA was suspended in 50 µl water and 0.5-1.0 µl was used in a 50 µl PCR reaction to amplify the RT domain. Amplification was carried out for 35 cycles (94° C. for 1 min, 60° C. for 1 min, 72° C. for 2 min) using primers A-35 (5'GAACCTCCGAGATCGAAGA3' (SEQ ID NO: 23)) and I1097 (5'GCACTGCCTCTGTTAATTGT3' (SEQ ID NO: 24)) resulting in a PCR product that includes the HIV-1 RT coding region for amino acids 1-367. PCR products were purified with the Qiaquick 96 PCR Purification Kit (Qiagen Sciences, Germantown, Md.) and sequenced with internal primers B275 (5'AGACTTCTGGGAAGTTCAAT3' (SEQ ID NO: 25)), 220F (5'TGGAGAAAATTAGTA-GATTT3' (SEQ ID NO: 26)) and J801 (5'ATCCCTGGG-TAAATCTGACT3' (SEQ ID NO: 27)).

TABLE 5

Oligonucleotides and primers used in the LigAmp assay*

| | | Ligation Oligonucleotides |
|---|---|---|
| ST | Position | Oligonucleotide sequence |
| A | Upstream | 5' ACTGTAAAACGACGGCCAGTGT*TCCCCTCAAACTGGCAGAT GCACGAGGAATACCACATGCAGCAGGTCTAAAAAAGGAC-3' |
| | Downstream | 5' AAATCAGTAACAGTACTAGATGTGGGGTGGTCATAGCTG TTTCCTGCA3' |
| D | Upstream | 5' ACTGTAAAACGACGGCCAGTGT*TCCCCTCAAACTGGCAGAT GCACGAGGAATACCACATCCTGCAGGGCTAAAAAAGGAC3' |
| | Downstream | 5' AAATCAGTAACAGTACTGGATGTGGGTGTGGTCATAGCTG TTTCCTGCA3' |

| | Real-Time PCR Primers and Probe |
|---|---|
| M13 forward primer | 5'-CTGTAAAACGACGGCCAGTG-3' |
| M13 reverse primer | 5'-TGCAGGAAACAGCTATGACCA-3' |
| LacZ probe | FAM-5'-TCCCCTCAAACTGGCAGATGCACG-3'-BHQ-1 |

*The sequences of ligation oligonucleotides designed for detection of the K103N mutation (AAA→AAC) for subtypes (ST) A and D are shown. Upstream and downstream ligation oligonucleotides include M13 tails (underlined). Upstream oligonucleotides also include a LacZ probe binding site (italics), and an intentional mismatch at the third position from the 3' end introduced to enhance the specificity of the LigAmp assay (G, bold). The sequences of primers and probes used in the real-time PCR detection step of the ligAmp assay are shown. The TaqMan probe includes a fluorophore (FAM) and a quencher (BHQ).

Table 6. Analysis of Samples Using the ViroSeq and Ty-HRT Assays

Tables 6A and 6B supplement information presented in FIGS. 25 and 26 in the manuscript. Each table shows results from the ViroSeq assay. NVPR mutations detected in the assay are indicated. The symbol (−) indicates that no NVPR mutations were detected. Detailed results from the TyHRT assay are shown for each sample, including: the number of transformed clones (yeast colonies) isolated with active HIV-1 RT (# clones), the number of clones with phenotypic NVPR (# NVPR), the number of clones with NVPR that were sequenced (# Seq), and the NVPR mutations identified in the sequenced clones (NVPR mutations). The number of clones with each mutation or combination of mutations is shown (e.g. 8-Y18C: eight clones with Y181C, 1-Y181C+G190A: one clone with both Y181C and G190A). In addition to the NVPR mutations shown, amino acid polymorphisms were detected in some clones at other positions which may influence NVP susceptibility (e.g. L100F, I132M, I135T/V, V179I, V189I, M230I). Table 6A provides data from samples from women (M) collected prior to NVP dosing (Pre), at delivery (Del), and at 7 days (7 d), 6-8 weeks (6 w) and 12, 14, or 24 months (12 m, 14 m, or 24 m) after delivery. Table 6B provides data from samples from infants (I) collected at birth (B), and at 6-8 weeks (6 w), 14-16 weeks (14 w) and 12 months (12 m) of age.

TABLE 6A

Analysis of maternal samples using the ViroSeq and TyHRT assays.

|  |  | ViroSeq | TyHRT Assay | | | |
|---|---|---|---|---|---|---|
|  |  |  | # clones | # NVPR | # Seq | NVPR mutations |
| M-470 | Pre | — | 270 | 0 | 0 | |
|  | Del | — | 244 | 0 | 0 | |
|  | 7 d | NR | 175 | 16 | 12 | 12-Y181C |
|  | 6 w | K103N | 190 | 40 | 10 | 7-K103N, 1-Y181C |
|  | 24 m | — | 174 | 0 | 0 | |
| M-474 | Pre | — | 133 | 0 | 0 | |
|  | Del | — | 267 | 5 | 5 | 1-G190E |
|  | 7 d | — | 196 | 21 | 9 | 2-M230L, 4-Y181C, 3-Y188C |
|  | 6 w | K103N | 198 | 44 | 7 | 4-K103N, 1-Y181C, 1-G190A |
|  | 24 m | — | 203 | 7 | 4 | 2-K103N |
| M-554 | Pre | — | 221 | 2 | 2 | 2-Y188H |
|  | Del | — | 204 | 0 | 0 | |
|  | 7 d | — | 164 | 2 | 2 | |
|  | 6 w | K103N, Y181C | 28 | 15 | 9 | 4-K103N, 1-K103N + Y181C, 4-V106A |
|  | 24 m | — | 56 | 0 | 0 | |
| M-660 | Pre | — | 75 | 1 | 1 | 1-Y181C |
|  | Del | — | 97 | 0 | 0 | |
|  | 7 d | NR | 42 | 4 | 2 | 2-Y181C |
|  | 6 w | K103N, Y181C | 112 | 64 | 9 | 1-K103N, 4-Y181C, 4-G190A |
|  | 24 m | — | 79 | 0 | 0 | |
| M-750 | Pre | — | 210 | 1 | 1 | 1-K103N |
|  | Del | — | 281 | 3 | 2 | 1-M230L, 1-V106A |
|  | 7 d | — | 263 | 3 | 2 | 2-Y188C |
|  | 6 w | K103N | 227 | 47 | 14 | 4-K103N, 3-V106A, 4-G190A, 1-Y181C, 1-K103N + Y188C, 1-V106A + G190A |
|  | 14 m | — | 310 | 2 | 2 | 1-K103N, 1-G190A |
| M-755 | Pre | — | 34 | 0 | 0 | |
|  | Del | — | 57 | 0 | 0 | |
|  | 7 d | NR | 81 | 2 | 2 | 2-V106A |
|  | 6 w | V108I | 30 | 0 | 0 | |
|  | 24 m | — | 22 | 0 | 0 | |
| M-790 | Pre | — | 381 | 0 | 0 | |
|  | Del | — | 283 | 0 | 0 | |
|  | 7 d | Y181C | 232 | 99 | 13 | 4-K103N, 5-Y181C, 1-K103N + Y181C, 1-Y188C, 1-G190A |
|  | 6 w | K103N | 219 | 68 | 6 | 6-K103N |
|  | 14 m | — | 292 | 3 | 2 | 1-Y188H |
| M-830 | Pre | — | 288 | 0 | 0 | |
|  | Del | — | 297 | 0 | 0 | |
|  | 7 d | NA | | | | |
|  | 6 w | K103N, Y181C | 313 | 105 | 11 | 8-K103N, 2-K103N + Y181C, 1-G190A |
|  | 14 m | — | 290 | 33 | 7 | 6-K103N |
| M-847 | Pre | — | 281 | 1 | 1 | Y181C |
|  | Del | — | 328 | 1 | 1 | |
|  | 7 d | Y181C, G190A | 299 | 82 | 8 | 4-G190A, 2-Y181C, 1-Y181C + V106A, 1-K103N |
|  | 6 w | K103N | 355 | 64 | 6 | 3-K103N, 2-G190A, 1-Y181C |
|  | 12 m | — | 308 | 2 | 2 | 2-V106A |

TABLE 6B

Analysis of infant samples using the ViroSeq and TyHRT assays.

|  |  | ViroSeq | TyHRT Assay | | | |
|---|---|---|---|---|---|---|
|  |  |  | # clones | # NVPR | # Seq | NVPR mutations |
| I-466 | B | — | 313 | 0 | 0 | |
|  | 6 w | Y181C | 360 | 61 | 9 | 8-Y181C |
|  | 14 w | — | 301 | 3 | 3 | 3-Y181C |
|  | 12 m | — | 248 | 0 | 0 | |

TABLE 6B-continued

Analysis of infant samples using the ViroSeq and TyHRT assays.

| | | ViroSeq | TyHRT Assay | | | |
|---|---|---|---|---|---|---|
| | | | # clones | # NVPR | # Seq | NVPR mutations |
| I-545 | B | — | 14 | 0 | 0 | |
| | 6 w | K103N | 249 | 107 | 9 | 8-K103N, 1-Y181C |
| | 14 w | K103N | 201 | 201 | 9 | 9-K103N |
| | 12 m | — | 311 | 1 | 1 | 1-K103N |
| I-750 | B | — | 287 | 2 | 2 | 1-Y188H, 1-V106A |
| | 6 w | K103N, Y181C | 210 | 17 | 6 | 3-K103N, 1-Y181C + G190A, 1-Y181C, 1-K103N + Y181C + Y188C |
| | 14 w | — | 190 | 5 | 6 | 2-Y181C, 1-K103N, 1-V106A, 1-V108I |
| | 12 m | G190A | 248 | 27 | 4 | 4-G190A |
| I-788 | B | — | 374 | 0 | 0 | |
| | 6 w | Y181C, Y188C | 271 | 142 | 6 | 3-Y181C, 3-Y188C |
| | 14 w | NA | | | | |
| | 12 m | — | 271 | 1 | 1 | Y181C |
| I-827 | B | — | 405 | 1 | 0 | |
| | 6 w | Y181C | 238 | 96 | 5 | 3-Y181C, 1-Y188C, 1-Y181C + G190E |
| | 14 w | Y181C | 95 | 15 | 4 | 4-Y181C |
| | 12 m | — | 146 | 1 | 1 | 1-Y188C |

Example 9

Oligonucleotides and probes: The K-ras and HIV-1 oligonucleotides (gel-purified), and M13 forward and reverse primers (Table 2) were purchased from Invitrogen, Corp. (Carlsbad, Calif.). The downstream common oligonucleotides were phosphorylated at the 5' end using T4 polynucleotide kinase (New England Biolabs, Beverly, Mass.). The lacZ and 16S rRNA Taqman probes containing different fluorophores and quenchers (Table 2) were purchased from Integrated DNA Technology (Corralville, Iowa)

Mutant K-ras oligonucleotide ligation: Wild-type (HeLa cells) and K-ras mutant (SW480 cells) genomic DNA was extracted using the DNeasy Tissue Kit (Qiagen, Valencia, Calif.). Ten-fold serial dilutions of the mutant DNA (1.2 µg to 12 pg) were made in 1.2 µg wild-type DNA. For ligation, 1 pmol of the K-ras upstream mutant or wild-type oligonucleotide and 1 pmol of the K-ras common oligonucleotide were incubated with the DNA in ligase buffer containing 20 mM Tris-HCl (pH 7.5), 20 mM KCl, 10 mM MgC12, 0.1% Igepal, 0.01 mM rATP, 1 mM DTT, and 4 U pfu DNA ligase (Stratagene, La Jolta, Calif.). The ligation conditions included denaturation at 95° C. for 3 min, followed by 90 cycles of 95° C. for 30 seconds and 65° C. for 4 min. Ligation reactions for wild-type and mutant alleles were performed in separate tubes, and used directly for Q-PCR without purification.

HIV-1 oligonucleotide ligation: Plasmids containing infectious molecular clones of HIV-1 DNA with and without the K103N drug resistance mutation were generously provided by Dr. John Mellors (Univ. of Pittsburgh). Pol region DNA was amplified from the plasmids using the ViroSeq™ HIV-1 Genotyping System (ViroSeq, Celera Diagnostics, Alameda, Calif.) and was subcloned into the pCRII-TOPO® cloning vector using the TOPO TA Cloning® Kit, Version N (Invitrogen). The wild-type and mutant plasmids were isolated using a commercial kit (QIAwell Ultra Plasmid Kit (Qiagen) and sequenced using the ViroSeq system. Ten-fold serial dilutions of the mutant plasmid were prepared by mixing the mutant plasmid with the wild-type plasmid. Plasmid mixtures were prepared at a final concentration of 2 pg/µl. Ligation was performed using 10 pg of plasmid mix and the conditions listed above, except that 2 pmol upstream oligonucleotide and 8 units of the ligase were used.

Q-PCR: Q-PCR amplification of ligated products was performed using a SmartCycler (Cepheid, Sunnyvale, Calif.). Each reaction (25 µl) contained 5 pmol forward and 5 pmol reverse M13 primers, 6 µl of the unpurified ligation reaction, 12.5 µl platinum Quantitative PCR SuperMix-UDG (Invitrogen), and 2.5 pmol of either the lacZ or 16S rRNA probe. PCR reactions included pre-incubation at 50° C. for 2 min and 95° C. for 2 min, followed by 50 cycles of 95° C. for 10 seconds and 64° C. for 20 seconds. Following Q-PCR detection, PCR products were electrophoresed on a 4-12% acrylamide gel (Novex® TBE gel, Invitrogen) and stained with ethidium bromide.

Q-PCR has a remarkably wide dynamic linear range, but has been difficult to apply to point mutation detection because probes that differ by a single nucleotide often cross-hybridize to both the wild-type and mutant templates. The strategy employs two unique oligonucleotides. Each of these contains a region specific to the target gene and an M13 tail, which facilitates subsequent PCR amplification of the ligated product with universal M13 amplification primers. The 3' end of the upstream wild-type and mutant oligonucleotides perfectly match the corresponding sequences in the appropriate target molecule (if present). The upstream oligonucleotide also contains a region of unique foreign DNA that serves as the binding region for a universal probe in a subsequent detection reaction. The analysis can be performed as a single reaction to detect and directly quantify only the mutant DNA, or as a pair of reactions where both mutant and wild-type DNA are detected separately for relative quantification. In either case, the strategy relies on the differentiating power of a DNA ligase to ligate the oligonucleotides only when they are both fully hybridized to the template DNA (no mismatch is present at the adjacent terminal nucleotides). Q-PCR with universal M13 primers is used to amplify the ligated product. The resulting amplicons are then detected using a universal probe. Both the M13 forward primer and the lacZ probe have the same polarity as the upstream ligation oligonucleotide (Table 2). Therefore, the lacZ probe cannot bind to the ligation oligonucleotide. Binding of the probe first requires successful ligation of the two oligonucleotides and polymerization of the complementary (bottom) strand of DNA by Taq polymerase. Subsequent extension of Taq polymerase from the M13 primer towards the bound LacZ probe allows the probe to be cleaved, and the fluorophore to be released and detected. " "A colon cancer cell line was used, SW480, which contains a K-ras mutation (GGT to GTT, Gly12Val), and performed 10-fold serial dilutions of this mutant DNA into HeLa cell line DNA, which contains wild-type K-ras genes. After ligation of either the mutant or wild-type specific oligonucleotide to the common oligonucleotide, Q-PCR was performed using the universal M13 primers and lacZ probe. It was then determined the cycle number at which threshold was achieved. The mutant K-ras DNA can be easily detected as a signal distinct from pure wild-type DNA even when present at a level of only 1:10,000 (4-5 cycles difference in Ct). At a concentration of 1:100,000, the signal is still distinct from that of wild-type alone (p<0.01, paired student t-test), though the difference was only 1-2 cycles. Detection of the K-ras mutant DNA was linear over the full range of dilutions (FIG. 2b, $r^2$=0.99). When the same amplified products shown in FIG. 2a were separated by polyacrylamide gel electrophoresis (PAGE, FIG. 2c), the intensity of the ethidium bromide-stained PCR product (106 bp) correlated well with the level of input mutant DNA, and correlated inversely with the Q-PCR cycle threshold, as expected.

As a second model system, it was tested whether LigAmp could be used to detect minority variants within a population of HIV-1 viruses. Mixtures of plasmids with wild-type (K=AAA) or mutant (N=AAC) codons at amino acid 103 in HIV-1 reverse transcriptase were prepared. The K103N mutation is associated with resistance to the non-nucleoside reverse transcriptase inhibitor (NNRTI) class of antiretroviral drugs used to treat HIV-1 infection. After preparing 10-fold serial dilutions of the mutant plasmid, ligation was performed with a mutant upstream and common downstream HIV-1 oligonucleotide (Table 2), and Q-PCR using the same M13 primers and lacZ probe (FIG. 4). The Ct was determined as described above. Using this approach, the K103N mutation were detected in the plasmid mixtures at a level of 1:10,000 (0.01%). The wild-type plasmid was not detected.

It was demonstrated that LigAmp, which converts nearly identical molecules into distinctive ones, is a highly sensitive and specific technique that can quantitatively detect low levels of DNA containing a single base mutation in the presence of a vast excess of wild-type DNA. A sensitivity of $10^{-4}$ to $10^{-5}$ was easily achieved and was reproducible. Based on previous estimates that each human cell contains approximately 6 pg genomic DNA. The present assay can detect as few as 2-20 molecules of mutant K-ras in the presence of vast excess of normal genomic DNA. A low level non-specific signal was observed using wild-type DNA as template, but was clearly distinct from the $10^{-4}$ to $10^{-5}$ dilution of the mutant DNA. This non-specific signal is generated during the ligation step, since this signal is not seen without the addition of ligated products. It presumably arises either because non-specific ligation still occurs across mispairs at a very low frequency, or because template-independent ligation occurs. The Q-PCR second step employs a probe that hybridizes to a foreign DNA sequence (e.g. lacZ) introduced into the ligated product. This minimizes the potential for detection of the wild-type sequence, making this method more specific than traditional Q-PCR based assays.

Most HIV-1 genotyping assays used to identify drug resistance mutations are designed to detect only the major viral population, and have relatively low sensitivity for minority variants. A recent blinded, multi-center study compared the sensitivity of different methods to detect minority variants of HIV-1 with the K103N drug resistance mutation that were present at different levels in laboratory-prepared viral stocks. Two allele-specific Q-PCR (AS-Q-PCR) assays and a yeast hybrid assay specific for HIV-1 reverse transcriptase could detect the mutation at <1%. One AS-Q-PCR assay detected the mutation as low as 0.1%. Other assays that were less sensitive included an RT-PCR assay witch allele-specific hybridization, two oligonucleotide ligation assays, single genome RT/PCR and sequencing, and RT/PCR with pyrosequencing, and RT/PCR with direct sequencing of the bulk population using two FDA-cleared HIV-1 genotyping assays. The interest in developing ultra-sensitive methods for detection of HIV-1 minority variants is growing, following the report of a study that suggests that the presence of such variants can influence treatment response. Using plasmid mixtures, LigAmp was able to detect the K103N mutation in mixtures at a level of $10^{-4}$ (0.01%).

LigAmp also has potential utility in the prenatal diagnosis setting, as it is often desirable to determine whether a known paternal point mutation has been transmitted to a fetus. Using LigAmp, it may be possible to detect such mutations in small numbers of fetal cells present in a wild-type mother's peripheral blood, thereby avoiding amniocentesis or chorionic villous sampling procedures that carry an approximate 0.5% risk of fetal loss.

TABLE 7

Oligonucleotides and probes
Table 1. Oligonucleotides and probes

| K-ras Ligation Oligos | Mutant K-ras upstream | 5'-A<u>CTGTAAAACGACGGCCAGTGT</u>-*TCCCCTCAAACTGGCAGATGCACG*-C-TTGTGGTAGTTGGAGCTGT\*-3' |
|---|---|---|
| | WT K-ras upstream | 5'-A-<u>CTGTAAAACGACGGCCAGTGT</u>-*CGTATTACCGCGGCTGCTGGCAC*-C-TTGTGGTAGTTGGAGCTGG\*-3' |
| | K-ras common downstream | 5'-PO$^4$-TGGCGTAGGCAAGAGTGCC-<u>TGGTCATAGCTGTTTCCTGCA</u>-3' |
| HIV-1 Ligation Oligos | Mutant HIV-1 upstream | 5'-A<u>CTGTAAAACGACGGCCAGTGT</u>-*TCCCCTCAAACTGGCAGATGCACG*-CGCAGGGTTAAAAAAG[G]AC\*-3' |

TABLE 7-continued

Oligonucleotides and probes
Table 1. Oligonucleotides and probes

| | | |
|---|---|---|
| | HIV-1 common downstream | 5'-PO$^4$-AAATCAGTAACAGTAC TGGATGTGGGTG-<u>TGGTCATAGCTGTTTC CTGCA</u>-3' |
| Amplification Primers | M13 forward | 5'-<u>CTGTAAAACGACGGCCAGTG</u>-3' |
| | M13 reverse | 5'-<u>TGCAGGAAACAGCTATGACCA</u>-3' |
| Probes | lacZ probe | FAM-5'-TCCCCTCAAACTGGCAGATGCACG-3'-BHQ-1 |
| | 16S rDNA | ROX-5'-CGTATTACCGCGGCTGCTGGCAC-3'-BHQ-2 |

Underlined: M13 Primer Binding Regions.
Italics: probe binding regions. Bold: K-ras-specific or HIV-1-specific regions. Asterisk: terminal bases with perfect homology to either the wild-type or mutant K-ras or HIV-1 sequences. FAM: 6-carboxyflurorescein. ROX: 6-carboxy-X-rhodamine. BHQ: black hole quencher. Boxed base: An additional mis-pair in the upstream HIV-1 mutant oligonucleotide at the third base from the 3' end was introduced to improve the specificity of the assay (the usual mutant 3' terminal sequence is GAAC).

Example 10

LigAmp may also be performed on both strands of DNA simultaneously. This further increases the specificity of the reaction because signal is only generated if the mutation is detected on both strands. The method may be performed as follows: 1) LigAmp oligonucleotides directed towards both strands of DNA. 2) Prevention of a ligase chain reaction (LCR). 3) Detection of ligated products during realtime PCR that requires both ligated products.

Oligonucleotides are placed on both strands of DNA containing the mutation, and both sets of oligonucleotides are complementary to one another. If a single ligation event occurs on either strand, this would serve as a substrate and initiate an LCR reaction using all four oligonucleotides. This can be prevented in a variety of ways, including a ligation reaction that does not use a thermostable polymerase and is not cycled. Alternatively, one can maintain use of the thermostable ligase and cycling and use pseudocomplementary or AEGIS bases (Hutter D, Benner S A. Expanding the genetic alphabet: non-epimerizing nucleoside with the pyDDA hydrogen-bonding pattern. J Org Chem. 2003 Dec. 12; 68(25):9839-42) which are included in the oligonucleotides at least at the terminal bases at the ligation site. These retain the ability to bind and ligate to the target mutant DNA, while preventing ligation to each other (FIG. 27, A). Alternatively, this can also be accomplished by using probes that contain regions (loops) of non-complementary bases imbedded within the oligonucleotides (FIG. 27, B). These oligonucleotides contain stabilizing regions that are complementary to the target and which serve to anchor the oligonucleotide to the target, followed by the non-homologous loop region which prevents the oligonucleotides targeting the opposite strand from binding, followed by a toe (consisting of only a few bases) that are sufficient to anneal and permit ligation since the oligonucleotide is anchored to the target using the anchor region. The toe region is insufficiently long so that the oligonucleotide targeting the opposite strand is capable of binding. Alternatively, one could place 2 oligonucleotides were both have homology to both strands so that 2 separate ligation events would need to occur to produce a closed circle, which would then be subsequently amplified (FIG. 27, C).

Detection of ligated products during realtime PCR that requires both ligated products can also be accomplished in a variety of ways. In one simple modification, each pair of oligonucleotides contains only 1 of the 2 M13 sites required to undergo amplification (FIG. 27, D). Alternatively, each of the ligation pairs of oligonucleotides could contain their own probe site and software could be modified so that detection is only reported if both probes undergo cleavage. Alternatively, both fluorchromes could contain additional moeities (e.g. biotin, digoxigenin) that could be used in a subsequent reaction to draw both cleaved fluorchromes probes to a single target (e.g. using avidin) such that they would be sufficiently close so that they could undergo a fluorescence resonance transfer (FRET) reaction. Similarly, one could design a single molecule that has 2 binding sites, one for biotin and one for digoxigenin so that only 1 fluorochrome from each reaction could be bound and that they would be bound with the appropriate spacing.

The disclosures of each and every patent, patent application and publication cited herein are hereby incorporated herein by reference in their entirety.

While the invention has been disclosed with reference to specific embodiments, it is apparent that other embodiments and variations of the invention may be devised by others skilled in the art without departing from the true spirit and scope of the invention. The appended claims are intended to be construed to include all such embodiments and equivalent variations.

What is claimed is:

1. A method for detecting the presence of pancreatic cancer or chronic pancreatitis in a human subject, the method comprising:

obtaining a sample of pancreatic juice from the subject, the sample comprising nucleic acids from the subject;

creating a reaction mixture by hybridizing the nucleic acids to a plurality of oligonucleotide pairs to detect both wild type KRAS2 and mutant KRAS2 sequences in the nucleic acid to form a reaction mixture, wherein each oligonucleotide pair:

comprises a first oligonucleotide and a second oligonucleotide, wherein each first oligonucleotide comprises a first gene specific region and a first primer region, each second oligonucleotide comprises a second gene specific region and a second primer region, and either the first oligonucleotide or the second oligonucleotide comprises a detection region; and in oligonucleotide pairs to detect mutant KRAS2 sequence either the first oligonucleotide or the second oligonucleotide comprises a nucleotide in the gene specific region that detects one of a G35A, a G35T, or a G34C nucleotide substitution in the KRAS2 sequence; and in each oligonucleotide pair the first oligonucleotide and the second oligonucleotide are suitable for ligation to one another;

subjecting the reaction mixture to a ligation reaction to form ligation products from said oligonucleotide pairs to detect both wild type KRAS2 and mutant KRAS2 sequences;

amplifying said ligation products to form wild type KRAS2 and mutant KRAS2 amplification products;

detecting the quantity of the wild type KRAS2 and mutant KRAS2 amplification products;

calculating a mutation level, wherein said mutation level is equal to quantity of mutant KRAS2/(quantity of mutant KRAS2+quantity of wild-type KRAS2); and detecting a mutation level that is less than 0.5% and correlating the mutation level that is less than 0.5% with the presence of chronic pancreatitis in the subject; or detecting a mutation level that is greater than 0.5% and less than 80% and correlating the mutation level that is greater than 0.5% and less than 80% with the presence of pancreatic cancer in the subject.

2. The method of claim 1, wherein a mutation level that is less than 0.5% is detected.

3. The method of claim 1, wherein a mutation level that is greater than 0.5% and less than 80% is detected.

4. The method of claim 1, further comprising monitoring KRAS mutation levels.

5. The method of claim 1, wherein the sensitivity is at least 76%.

6. The method of claim 1, wherein the sensitivity is at least 88%.

7. The method of claim 1, wherein the sensitivity is 94%.

8. The method of claim 1, wherein a first oligonucleotide or a second oligonucleotide comprises a foreign DNA region between the gene specific region and the primer region.

9. The method of claim 8, wherein the foreign DNA region is used as a probe.

10. The method of claim 1, wherein amplification comprises a method selected from the group consisting of the amplifying is by quantitative polymerase chain reaction (PCR), real time PCR, and real time quantitative PCR.

11. The method of claim 10, wherein the amplifying comprises a multiplex PCR reaction.

* * * * *

UNITED STATES PATENT AND TRADEMARK OFFICE
CERTIFICATE OF CORRECTION

PATENT NO. : 8,679,788 B2
APPLICATION NO. : 10/590541
DATED : March 25, 2014
INVENTOR(S) : Eshleman et al.

It is certified that error appears in the above-identified patent and that said Letters Patent is hereby corrected as shown below:

In the Specification

Column 1, lines 13-16, please replace the second paragraph to read as follows:

GOVERNMENT SUPPORT

This invention was made with government support under grant numbers CA081439, AI046745, AI048054, AI038858, HD042965, AI035172, CO012400, awarded by the National Institutes of Health. The government has certain rights in the invention.

Signed and Sealed this
Third Day of June, 2014

Michelle K. Lee
*Deputy Director of the United States Patent and Trademark Office*